United States Patent
Charrier et al.

(10) Patent No.: US 8,846,686 B2
(45) Date of Patent: Sep. 30, 2014

(54) COMPOUNDS USEFUL AS INHIBITORS OF ATR KINASE

(71) Applicant: Vertex Pharmaceuticals Incorporated, Cambridge, MA (US)

(72) Inventors: Jean-Damien Charrier, Wantage (GB); Pierre-Henri Storck, Abingdon (GB); John Studley, Witney (GB); Francoise Yvonne Theodora Marie Pierard, Abingdon (GB); Steven John Durrant, Abingdon (GB); Benjamin Joseph Littler, Carlsbad, CA (US); Paul Angell, Carlsbad, CA (US); Robert Michael Hughes, San Diego, CA (US); David Andrew Siesel, San Diego, CA (US); Armando Urbina, San Diego, CA (US); Carl Zwicker, Brighton, MA (US); Nicholas LoConte, Winthrop, MA (US); Timothy E. Barder, Arlington, MA (US)

(73) Assignee: Vertex Pharmaceuticals Incorporated, Boston, MA (US)

(*) Notice: Subject to any disclaimer, the term of this patent is extended or adjusted under 35 U.S.C. 154(b) by 0 days.

(21) Appl. No.: 13/631,732

(22) Filed: Sep. 28, 2012

(65) Prior Publication Data

US 2013/0089625 A1    Apr. 11, 2013

Related U.S. Application Data

(60) Provisional application No. 61/541,861, filed on Sep. 30, 2011, provisional application No. 61/554,174, filed on Nov. 1, 2011, provisional application No. 61/620,698, filed on Apr. 5, 2012.

(51) Int. Cl.
| | | |
|---|---|---|
| A61K 31/4965 | (2006.01) | |
| A61K 38/00 | (2006.01) | |
| A61P 35/00 | (2006.01) | |
| C12P 15/00 | (2006.01) | |
| G01N 33/53 | (2006.01) | |
| A61K 31/7068 | (2006.01) | |
| A61K 33/24 | (2006.01) | |
| A61K 31/497 | (2006.01) | |
| A61N 5/10 | (2006.01) | |
| A61K 45/06 | (2006.01) | |
| C07D 413/14 | (2006.01) | |
| A61K 31/4745 | (2006.01) | |

(52) U.S. Cl.
CPC .......... *C07D 413/14* (2013.01); *A61K 31/7068* (2013.01); *A61K 33/24* (2013.01); *A61K 31/497* (2013.01); *A61N 5/10* (2013.01); *A61K 45/06* (2013.01); *A61K 31/4745* (2013.01)
USPC ................... 514/255.05; 514/19.2; 514/19.3; 435/127; 435/7.71

(58) Field of Classification Search
None
See application file for complete search history.

(56) References Cited

U.S. PATENT DOCUMENTS

| | | | |
|---|---|---|---|
| 4,309,430 | A | 1/1982 | Bock et al. |
| 5,143,824 | A | 9/1992 | Yamakawa et al. |
| 6,660,753 | B2 | 12/2003 | Van Wagenen et al. |
| 6,858,600 | B2 | 2/2005 | Hamilton et al. |
| 6,992,087 | B2 | 1/2006 | Verhoest et al. |
| 7,041,672 | B2 | 5/2006 | Verhoest et al. |
| 7,199,123 | B2 | 4/2007 | Munchhof |
| 7,452,993 | B2 | 11/2008 | Arnold et al. |
| 7,622,583 | B2 | 11/2009 | Ungashe et al. |
| 7,626,021 | B2 | 12/2009 | Arnold et al. |
| 7,704,995 | B2 | 4/2010 | Buhr et al. |
| 7,829,558 | B2 | 11/2010 | Arnold et al. |
| 7,872,031 | B2 | 1/2011 | Lauffer et al. |
| 7,902,197 | B2 | 3/2011 | Elworthy et al. |
| 7,932,254 | B2 | 4/2011 | DuBois et al. |
| 7,939,531 | B2 | 5/2011 | Bamberg et al. |
| 8,063,032 | B2 | 11/2011 | Chytil et al. |
| 8,410,112 | B2 | 4/2013 | Charrier et al. |
| 2003/0008882 | A1 | 1/2003 | Hamilton et al. |
| 2003/0055085 | A1 | 3/2003 | Wagenen et al. |
| 2004/0034037 | A1 | 2/2004 | Harbeson et al. |
| 2004/0180905 | A1 | 9/2004 | Munchhof |
| 2006/0211709 | A1 | 9/2006 | Buhr et al. |
| 2007/0037794 | A1 | 2/2007 | Ungashe et al. |
| 2007/0254868 | A1 | 11/2007 | Lauffer et al. |
| 2007/0270420 | A1 | 11/2007 | Harbeson et al. |
| 2007/0287711 | A1 | 12/2007 | Arnold et al. |
| 2009/0005381 | A1 | 1/2009 | Brown et al. |
| 2009/0215724 | A1 | 8/2009 | DuBois et al. |
| 2009/0215750 | A1 | 8/2009 | Bamberg et al. |
| 2009/0215785 | A1 | 8/2009 | DuBois et al. |
| 2009/0215788 | A1 | 8/2009 | Elworthy et al. |
| 2009/0306087 | A1 | 12/2009 | Ibrahim et al. |
| 2010/0036118 | A1 | 2/2010 | Arnold et al. |
| 2010/0168138 | A1 | 7/2010 | DeGoey et al. |
| 2010/0204214 | A1 | 8/2010 | Chytil et al. |
| 2010/0222318 | A1 | 9/2010 | Charrier et al. |
| 2010/0233091 | A1 | 9/2010 | Neumann et al. |
| 2011/0015231 | A1 | 1/2011 | Al-Abed et al. |
| 2011/0288067 | A1 | 11/2011 | Hendricks et al. |
| 2011/0288097 | A1 | 11/2011 | Hendricks et al. |
| 2012/0027874 | A1 | 2/2012 | Charrier et al. |
| 2012/0035407 | A1 | 2/2012 | Charrier et al. |
| 2012/0035408 | A1 | 2/2012 | Charrier et al. |
| 2012/0040020 | A1 | 2/2012 | Charrier et al. |
| 2012/0046295 | A1 | 2/2012 | Charrier et al. |
| 2012/0065247 | A1 | 3/2012 | Thompson et al. |
| 2012/0115874 | A1 | 5/2012 | Wang et al. |
| 2012/0122884 | A1 | 5/2012 | Charrier et al. |
| 2012/0177748 | A1 | 7/2012 | Charrier et al. |
| 2012/0178756 | A1 | 7/2012 | Charrier et al. |
| 2013/0017273 | A1 | 1/2013 | Everitt et al. |
| 2013/0018035 | A1 | 1/2013 | MacCormick et al. |
| 2013/0034616 | A1 | 2/2013 | Storck et al. |
| 2013/0089624 | A1 | 4/2013 | Charrier et al. |
| 2013/0089625 | A1 | 4/2013 | Charrier et al. |
| 2013/0089625 | A1 | 4/2013 | Pollard et al. |
| 2013/0095193 | A1 | 4/2013 | Charrier et al. |
| 2013/0096139 | A1 | 4/2013 | Charrier et al. |
| 2013/0115310 | A1 | 5/2013 | Charrier et al. |
| 2013/0115311 | A1 | 5/2013 | Charrier et al. |
| 2013/0115312 | A1* | 5/2013 | Charrier et al. ............... 424/649 |
| 2013/0115313 | A1 | 5/2013 | Charrier et al. |
| 2013/0115314 | A1* | 5/2013 | Charrier et al. ............... 424/649 |
| 2013/0172273 | A1 | 7/2013 | Aizpurua Iparraguirre et al. |
| 2013/0184292 | A1 | 7/2013 | Charrier et al. |

FOREIGN PATENT DOCUMENTS

| | | | |
|---|---|---|---|
| EP | 313724 | A2 | 5/1989 |
| EP | 1217000 | A1 | 6/2002 |
| EP | 2157090 | A1 | 2/2010 |
| WO | 9743267 | A1 | 11/1997 |
| WO | 9842701 | A1 | 10/1998 |
| WO | 0004014 | A1 | 1/2000 |
| WO | 0144206 | A1 | 6/2001 |
| WO | 0209648 | A2 | 2/2002 |
| WO | 03004472 | A1 | 1/2003 |
| WO | 03004475 | A1 | 1/2003 |
| WO | 03045924 | A1 | 6/2003 |
| WO | 03076422 | A1 | 9/2003 |
| WO | 03080610 | A1 | 10/2003 |
| WO | 03087057 | A1 | 10/2003 |
| WO | 03092686 | A1 | 11/2003 |
| WO | 03093297 | A2 | 11/2003 |
| WO | 03101968 | A1 | 12/2003 |
| WO | 2004000318 | A2 | 12/2003 |
| WO | 2004033431 | A2 | 4/2004 |
| WO | 2004055005 | A1 | 7/2004 |
| WO | 2004055006 | A1 | 7/2004 |
| WO | 2004084813 | A2 | 10/2004 |
| WO | 2004084824 | A2 | 10/2004 |
| WO | 2004085409 | A2 | 10/2004 |
| WO | 2004103279 | A2 | 12/2004 |
| WO | 2005028475 | A2 | 3/2005 |
| WO | 2005079802 | A1 | 9/2005 |
| WO | 2005123672 | A2 | 12/2005 |
| WO | 2006015124 | A2 | 2/2006 |
| WO | 2006053342 | A2 | 5/2006 |
| WO | 2006058074 | A1 | 6/2006 |
| WO | 2006067462 | A1 | 6/2006 |
| WO | 2006071548 | A2 | 7/2006 |
| WO | 2006075152 | A1 | 7/2006 |
| WO | 2006088837 | A2 | 8/2006 |
| WO | 2006114180 | A1 | 11/2006 |
| WO | 2006120573 | A2 | 11/2006 |
| WO | 2007015632 | A1 | 2/2007 |
| WO | 2007058850 | A2 | 5/2007 |
| WO | 2007063012 | A1 | 6/2007 |
| WO | 2007066805 | A1 | 6/2007 |
| WO | 2007076360 | A1 | 7/2007 |
| WO | 2007096151 | A2 | 8/2007 |
| WO | 2007096764 | A2 | 8/2007 |
| WO | 2007096765 | A1 | 8/2007 |
| WO | 2007102770 | A1 | 9/2007 |
| WO | 2007111904 | A2 | 10/2007 |
| WO | 2007126964 | A2 | 11/2007 |
| WO | 2007147874 | A1 | 12/2007 |
| WO | 2008037477 | A1 | 4/2008 |
| WO | 2008038010 | A1 | 4/2008 |
| WO | 2008040651 | A1 | 4/2008 |
| WO | 2008060907 | A2 | 5/2008 |
| WO | 2008071456 | A2 | 6/2008 |
| WO | 2008074997 | A1 | 6/2008 |
| WO | 2008079291 | A2 | 7/2008 |
| WO | 2008079903 | A1 | 7/2008 |
| WO | 2008079906 | A1 | 7/2008 |
| WO | 2008103277 | A2 | 8/2008 |
| WO | 2008106692 | A1 | 9/2008 |
| WO | 2008122375 | A2 | 10/2008 |
| WO | 2008124850 | A1 | 10/2008 |
| WO | 2008141065 | A1 | 11/2008 |
| WO | 2008144463 | A1 | 11/2008 |
| WO | 2008144464 | A1 | 11/2008 |
| WO | 2008157191 | A2 | 12/2008 |
| WO | 2009007390 | A2 | 1/2009 |
| WO | 2009012482 | A2 | 1/2009 |
| WO | 2009014637 | A2 | 1/2009 |
| WO | 2009016460 | A2 | 2/2009 |
| WO | 2009024825 | A1 | 2/2009 |
| WO | 2009037247 | A1 | 3/2009 |
| WO | 2009053737 | A2 | 4/2009 |
| WO | 2009106885 | A1 | 9/2009 |
| WO | 2010015803 | A1 | 2/2010 |
| WO | 2010048131 | A1 | 4/2010 |
| WO | 2010054398 | A1 | 5/2010 |
| WO | 2010063634 | A1 | 6/2010 |
| WO | 2010068483 | A2 | 6/2010 |
| WO | 2010071837 | A1 | 6/2010 |
| WO | 2011008830 | A1 | 1/2011 |
| WO | 2011117145 | A2 | 9/2011 |
| WO | 2011124998 | A1 | 10/2011 |
| WO | 2011130689 | A1 | 10/2011 |
| WO | 2011143399 | A1 | 11/2011 |
| WO | 2011143419 | A1 | 11/2011 |
| WO | 2011143422 | A1 | 11/2011 |
| WO | 2011143423 | A2 | 11/2011 |
| WO | 2011143425 | A2 | 11/2011 |
| WO | 2011143426 | A1 | 11/2011 |
| WO | 2011144584 | A1 | 11/2011 |
| WO | 2011144585 | A1 | 11/2011 |
| WO | 2012158785 | A1 | 11/2012 |
| WO | 2013049726 | A2 | 4/2013 |

OTHER PUBLICATIONS

Non-Final Office Action dated Aug. 8, 2013 in U.S. Appl. No. 13/631,727.

Non-Final Office Action dated Aug. 8, 2013 in U.S. Appl. No. 13/631,732.

Katritzky, A.R., et al., "Efficient synthesis of 3,5-functionalized isoxazoles and isoxazolines via 1,3-dipolar cycloaddition reactions of 1-propargyl- and 1-allylbenzotriazoles", J. Heterocyclic Chem., 37(6), (2000), pp. 1505-1510.

Kumpaty, H.J., et al., "Synthesis of N-Methyl Secondary Amines", Synth. Commun., 33(8), (2003), pp. 1411-1416.

March, J., March's Advanced Organic Chemistry, 2007, John Wiley and Sons, Chapter 16.

Wuts, P.G.M., Greene's Protective Groups in Organic Synthesis, 4th Edition, 2006, John Wiley and Sons, Chapter 4.

Wuts, P.G.M., Greene's Protective Groups in Organic Synthesis, 4th Edition, 2006, John Wiley and Sons, Chapter 7.

Abdel-Magid, A., "Inhibitors of ATR Kinase for Treatment on Cancer", ACS Medicinal Chemistry Letters, 4(8), (2013), pp. 688-689.

Ammar, Y.A., et al., "3-Ethoxycarbonylmethylenequinoxalin-2-one in Heterocyclic Synthesis. Part 1: Synthesis of New Substituted and Condensed Quinoxalines", Afinidad (2005), 62, pp. 151-160.

Charrier, J.D., et al, "Discovery of Potent and Selective Inhibitors of Ataxia Telangiesctasia Mutated and Rad3 Related (ATR) Protein Kinase as Potential Anticancer Agents" J. Med. Chem. (Mar. 17, 2011), 54(7), pp. 2320-2330 (DOI: 10.1021/jm101488z).

Charrier, J.D., et al., "Discovery of Potent and Selective Inhibitors of ATR (Ataxia Telangiectasia Mutated and Rad3 Related) as Potential Anticancer Agents", Supplementary Information, Apr. 14, 2011.

Charrier, J.D., "Discovery of potent and selective inhibitors of Ataxia Telangiectasia mutated and Rad3 related (ATR) protein kinase as potential anticancer agents", Presentation, ACS Denver 2011, Aug. 28, 2011.

Clark, B.A.J., et al., "Mass Spectrometry of Pyrroloä2, 3-Büpyrazines and Pyrazinoä2,3-Büindole", Organic Mass Spectrometry, 12(7), (1997), pp. 421-423.

Curtin, N.J., "Inhibiting the DNA damage response as a therapeutic manoeuvre in cancer", British Journal of Pharmacology, (2013), pp. 1-52.

El-Emary, T.I., "Synthesis and Biological Activity of Some New Pyrazolo[3,4-b]pyrazines", J. Chin. Chem. Soc. (2006), 53, pp. 391-401.

Fernandes, P.S., et al., "Synthesis and Biological Activity of Heterocyclic Derivatives derived from Ethyl-2-hydroxy-quinoxaline-3-carboxylate", J. Indian Chem. Soc. (1986), 63, pp. 427-429.

Finlay, M.R. et al. "Modulation of DNA repair by pharmacological inhibitors of the PIKK protein kinase family", Bioorg. Med. Chem. Letters, 22(17) (2012), pp. 5352-5359.

Fokas, E., et al., "Targeting ATR in vivo using the novel inhibitor VE-822 results in selective sensitization of pancreatic tumors to radiation", Cell Death and Disease, 3 (2012), pp. 1-5 (DOI: 10.1038/cddis.2012.181).

Fokas, E., et al., "Targeting ATR in DNA damage response and cancer therapeutics", Cancer Treatment Reviews (2013), (DOI: 10.1016/j.ctrv.2013.03.002).

Gentili, F., et al., "Alpha2-Adrenoreceptors Profile Modulation. 4. From Antagonist to Agonist Behavior", J. Med. Chem., 51(14), Jun. 25, 2008), pp. 4289-4299.
Hall-Jackson, C.A., et al., "ATR is a caffeine-sensitive, DNA-activated protein kinase with a substrate specificity distinct from DNA-PK", Oncogene, 18(48) (1999), pp. 6707-6713.
Hickson, I., et al., "Identification and Characterization of a Novel and Specific Inhibitor of the Ataxia-Telangiectasia Mutated Kinase ATM", Cancer Research (2004), 64, pp. 9152-9159.
Hilton, S., et al., "Identification and characterisation of 2-aminopyridine inhibitors of checkpoint kinase 2", Bioorg. Med. Chem., (2010) 18, pp. 707-718.
Jiang, B., et al., "Synthesis and cytotoxicity evaluation of novel indolylpyrimidiens and indolylpyrazines as potential antitummor agents", Bioorganic & Medicinal Chemistry, 9 (2001), pp. 1149-1154.
Kim, S.T., et al., "Substrate Specificities and Identification of Putative Substrates of ATM Kinase Family Members", J. Biol. Chem. (1999) 274, pp. 37538-37543.
Klicnar, J., et al., "Studien in der Chinoxalinreihe III. Syntheses, Reaktionen und ir-spektren einiger 3-hydroxy-2-carboxymethylchinoxalin-derivative", Collection Czechoslav. Chem. Commun. (1965), 30, pp. 3092-3101.
Kurasawa, Y., et al., "Revised Structure for the Product from the Reaction of 3-Hydrazinocarbonylmethylene-2-oxo-1,2,3,4-tetrahydroquinoxaline with Nitrous Acid", Chem. Pharm. Bull. (1984), 32(10), pp. 4140-4143.
Luo, H., et al., "Molecular dynamics-based self-organizing molecular field analysis on 3-amino-6-arypyrazines as the ataxia telangiectasia mutated and Rad3 related (ATR) protein kinase inhibitors", Medicinal Chemistry Research, (2013), pp. 1-12.
McKenna, G., et al., "Evaluation of the first potent and highly selective inhibitor of ATR kinase: an approach to selectively sensitize cancer cells to ionizing radiation and hypoxia", Abstract, Mar. 31, 2012.
McKenna, G., et al., "Evaluation of the first potent and highly selective inhibitor of ATR inhibitor, VE-821: an approach to selectively sensitize cancer cells to ionizing radiation and hypoxia", Poster, Mar. 31, 2012.
Middleton, F., et al., "ATR as a Therapeutic Target", Advances in DNA Repair in Cancer, Northern Institute for Cancer Research, Newcastle University (2013), pp. 211-228.
Nakamura, H., et al., "Bimodal chemiluminescence of 8-chlorostyryl-6-phenylethynylimidazopyrazinone: Large bathochromic shift caused by a styryl group at 8-position", Tetrahedron Letters, 39, (1998), pp. 301-304.
Pires, I.M., et al., "Targeting radiation-resisitant hypoxic tumour cells thorugh ATR inhibition", British Journal of Cancer, Jun. 19, 2012, pp. 1-9.
Pollard, J., "Inhibition of the DNA Damage Response Kinase, ATR, as a Promising Anti-Cancer Approach", Presentation, Mar. 8, 2012.
Qi, et al., "Chemi- and bio-luminescence of coelenterazine analogs with phenyl homologs at the C-2 position", Journal of the Chemical Society, Perkin Transactions 1: Organic and Bio-Organic Chemistry,13, (1992), pp. 1607-1611.
Reaper, P.M., et al., "Selective Killing of ATM- or p53-deficient cancer cells through inhibition of ATR", Supplementary Information, Nature Chemical Biology, Apr. 13, 2011, DOI: 10.1038/NCHEMBIO.573.
Reaper, P.M., et al., "Selective Killing of ATM- or p53-deficient cancer cells through inhibition of ATR", Presentation, Nov. 21, 2011.
Reaper, P.M., et al., "Selective Killing of ATM- or p53-deficient cancer cells through inhibition of ATR", Presentation, Nov. 29, 2011.
Reaper, P.M., et al., "Evaluation of a potent and highly selective inhibitor of ATR kinase: an approach to selectively sensitize cancer cells to genotoxic drugs", Abstract, Mar. 31, 2012.
Reaper, P.M., et al., "Evaluation of a Potent and Highly Selective Inhibitor of ATR Kinase: An Approach to Selectively Sensitize Cancer Cells to Genotoxic Drugs", Poster, Mar. 31, 2012.
Sarkaria, J.N., et al., "Inhibition of ATM and ATR Kinase Activities by the Radiosensitizing Agent, Caffeine", Cancer Research (1999) 59, pp. 4375-4382.
Sugimoto, T., et al., "Imidazopteridines. I. Synthesis of Imidazo[1,2-c]pteridine and Its Alkyl Derivatives", Bull. Chem. Soc. Japan (1977) 50(10), pp. 2744-2747.

Ward, I.M., et al., "Histone H2AX Is Phosphorylated in an ATR-dependent Manner in Response to Replicational Stress", J. Biol. Chem. (2001), 51, pp. 47759-47762.

* cited by examiner

*Primary Examiner* — Jeffrey S. Lundgren
*Assistant Examiner* — Tori M Strong
(74) *Attorney, Agent, or Firm* — Jennifer G. Che

(57) ABSTRACT

The present invention relates to compounds useful as inhibitors of ATR protein kinase. The invention also relates to pharmaceutically acceptable compositions comprising the compounds of this invention; methods of treating of various diseases, disorders, and conditions using the compounds of this invention; processes for preparing the compounds of this invention; intermediates for the preparation of the compounds of this invention; solid forms of the compounds of this invention; and methods of using the compounds in in vitro applications, such as the study of kinases in biological and pathological phenomena; the study of intracellular signal transduction pathways mediated by such kinases; and the comparative evaluation of new kinase inhibitors.

The compounds of this invention have formula I-1:

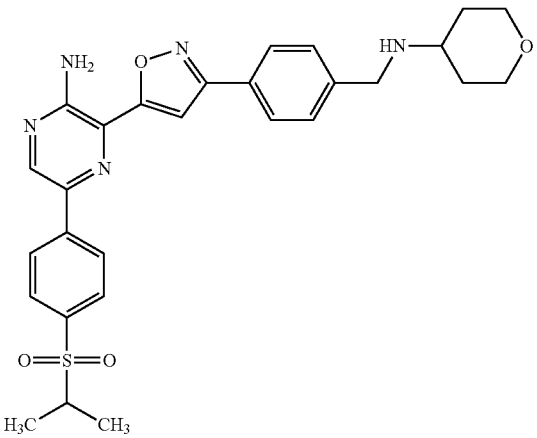

wherein the variables are as defined herein.

Additionally, the compounds of this invention have formula II:

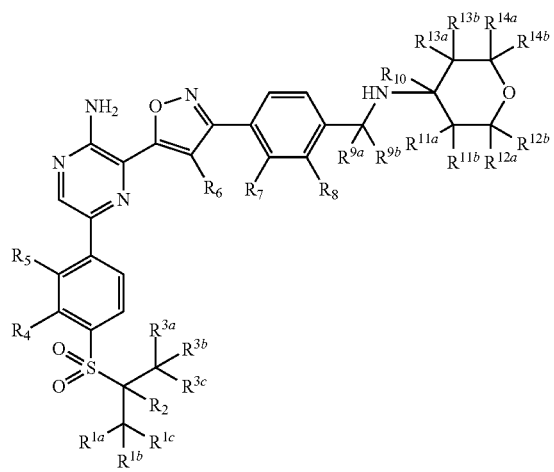

or a pharmaceutically acceptable salt thereof, wherein the variables are as defined herein.

47 Claims, 9 Drawing Sheets

FIGURE 1A: Compound I-1 free base XRPD
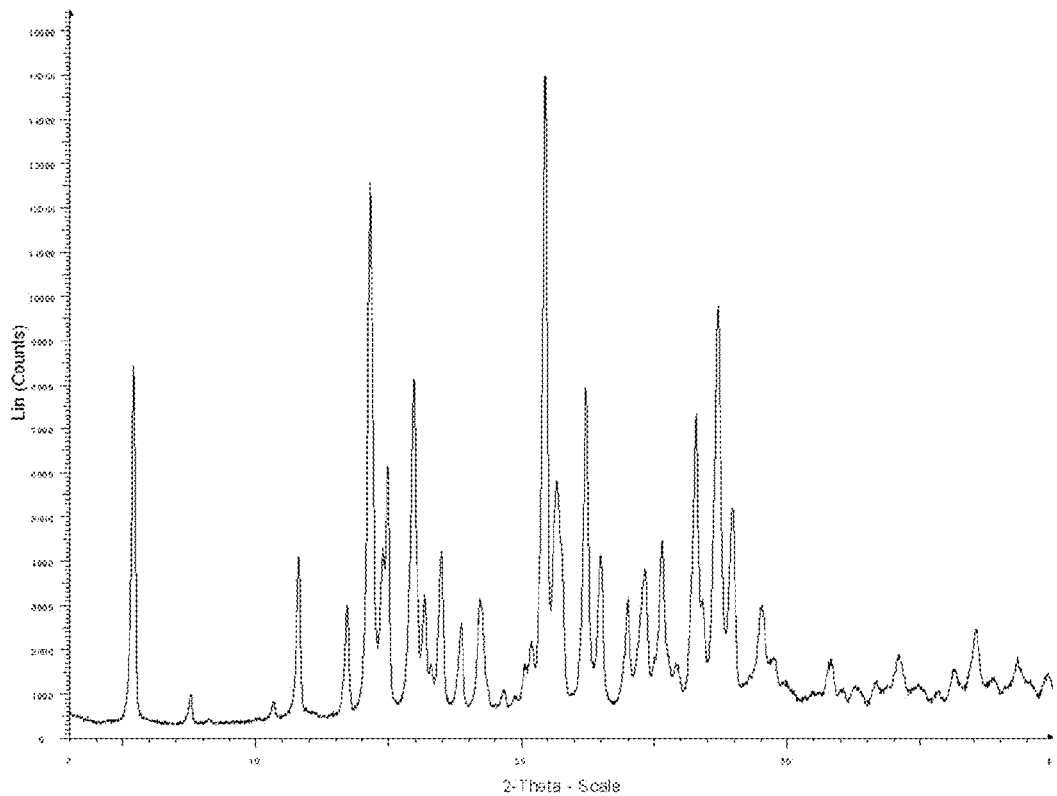
FIGURE 2A: Compound I-1 TGA
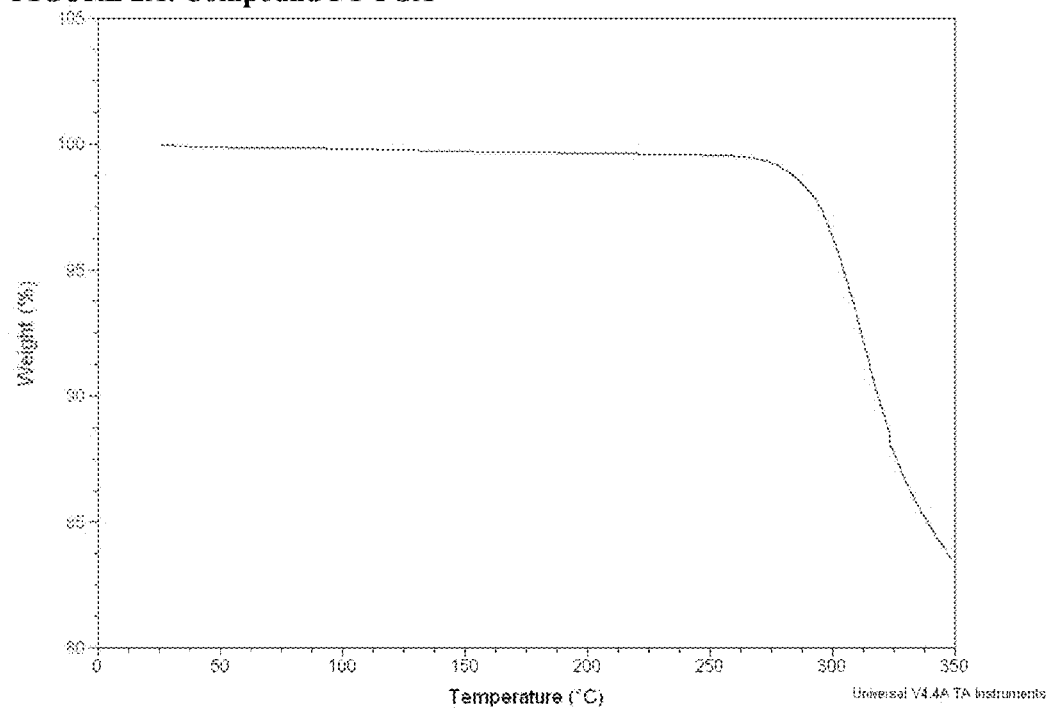

FIGURE 3A: Compound I-1 DSC
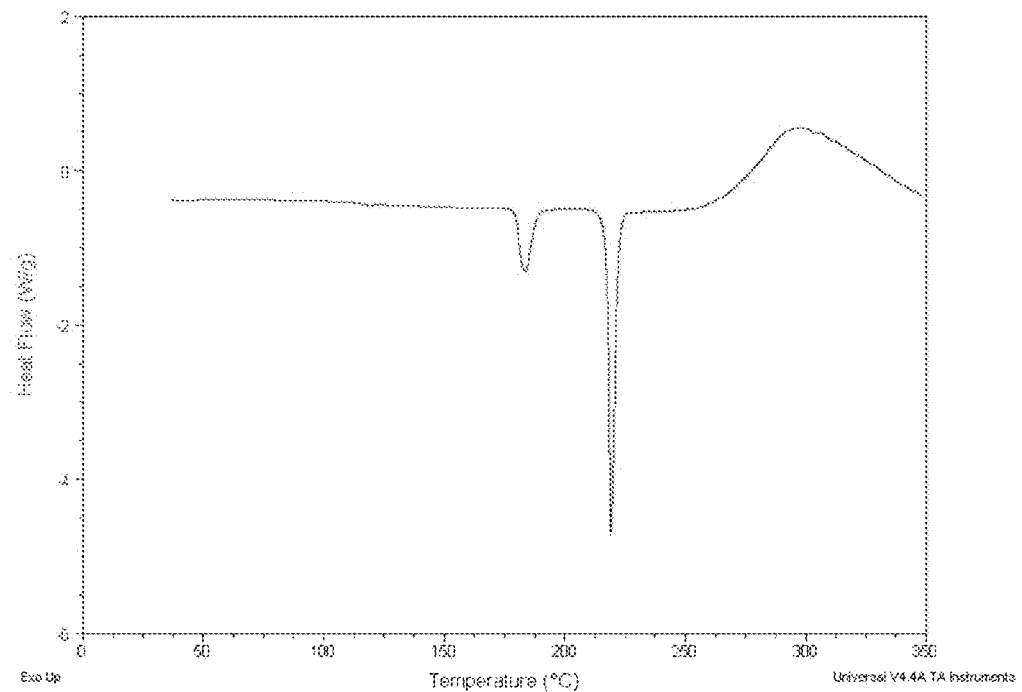
FIGURE 1B: Compound I-1 • hydrochloric acid XRPD
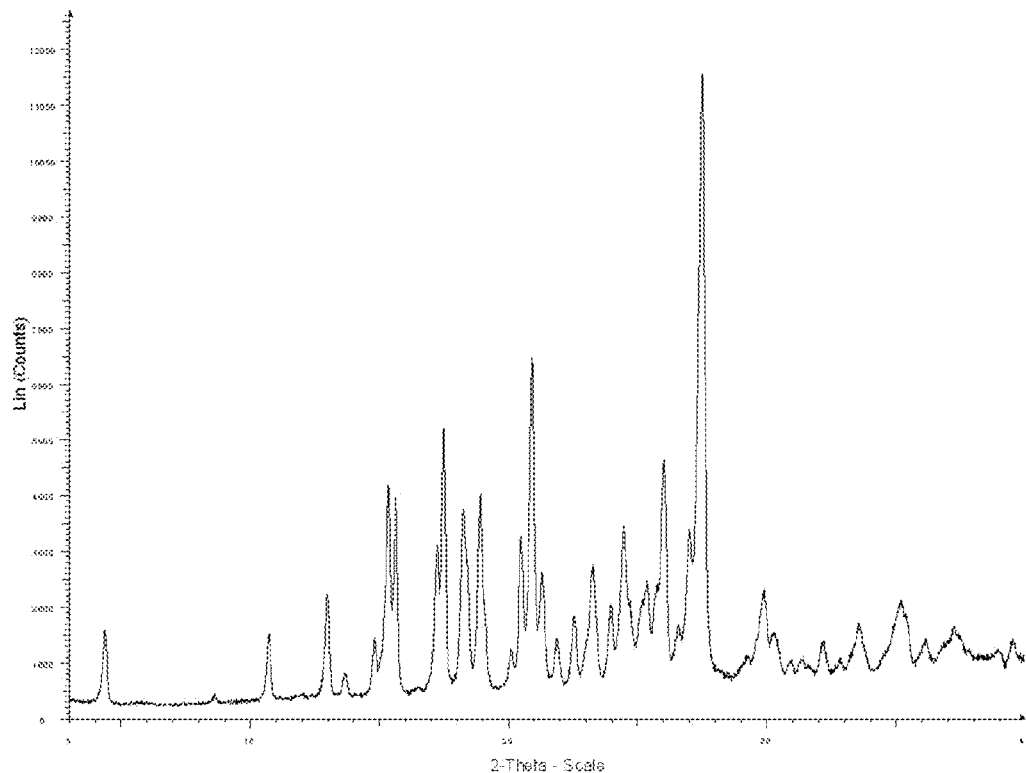

FIGURE 1C: Compound I-1 • hydrate XRPD
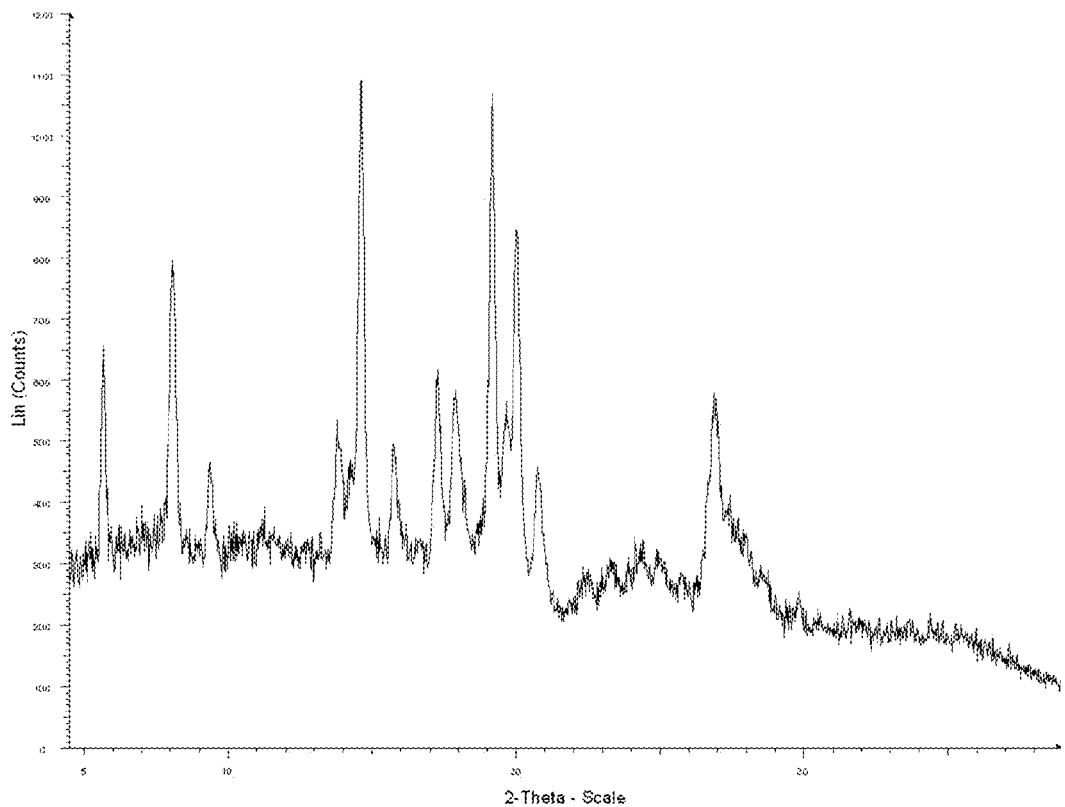
FIGURE 2C: Compound I-1 • hydrate TGA
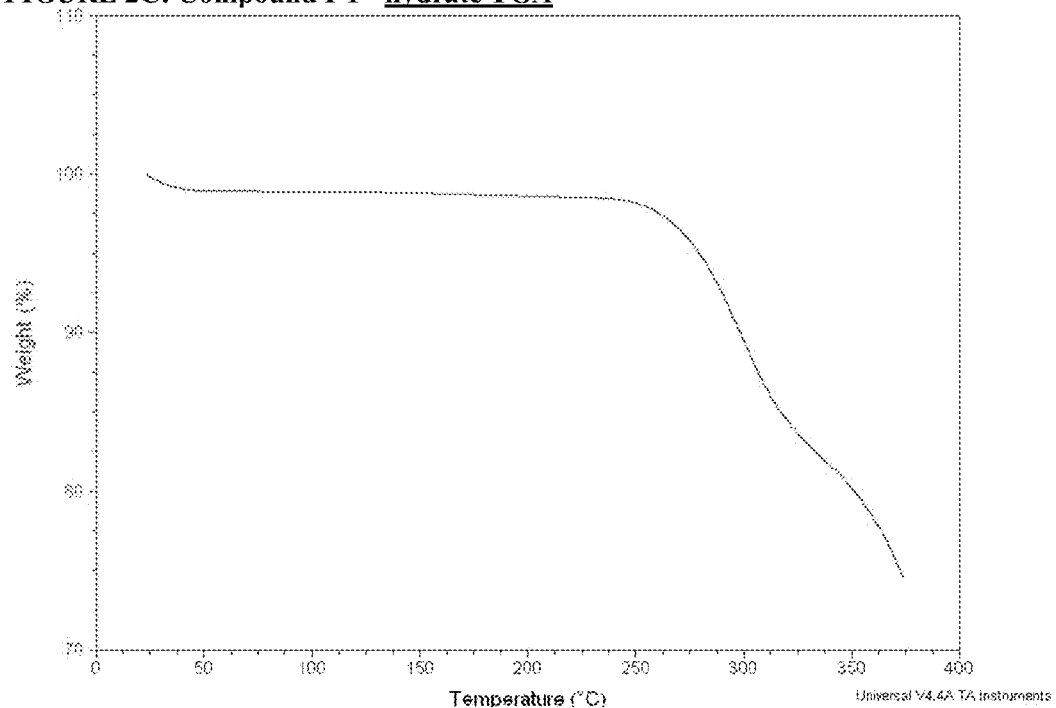

FIGURE 3C: Compound I-1 • hydrate DSC
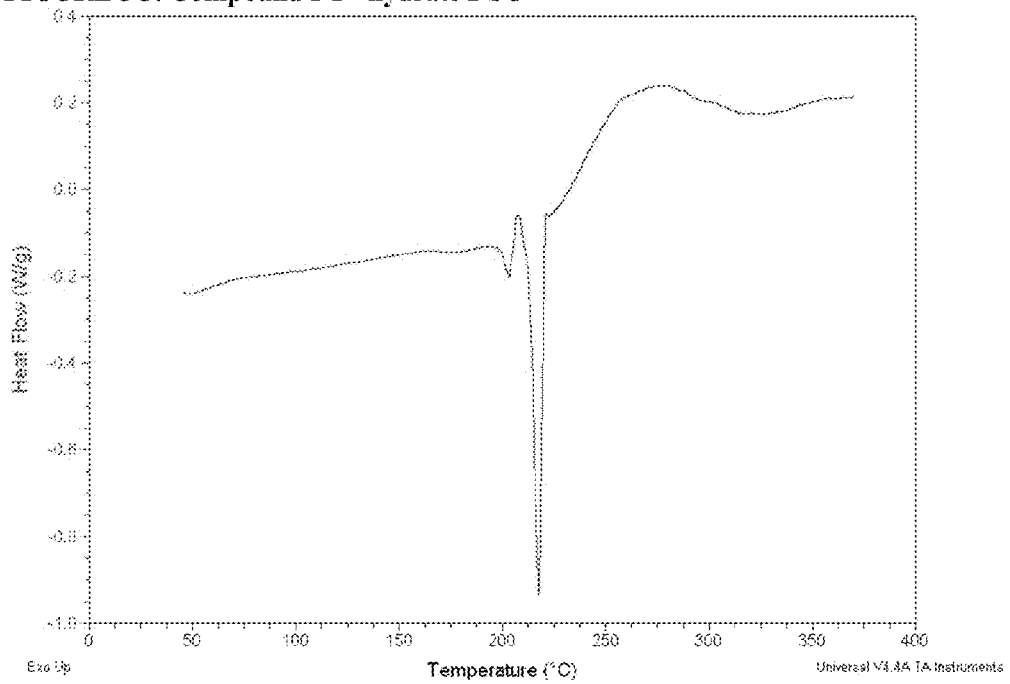
FIGURE 1D: Compound I-1 • 2-hydrochloric acid • 1.5 $H_2O$ XRPD
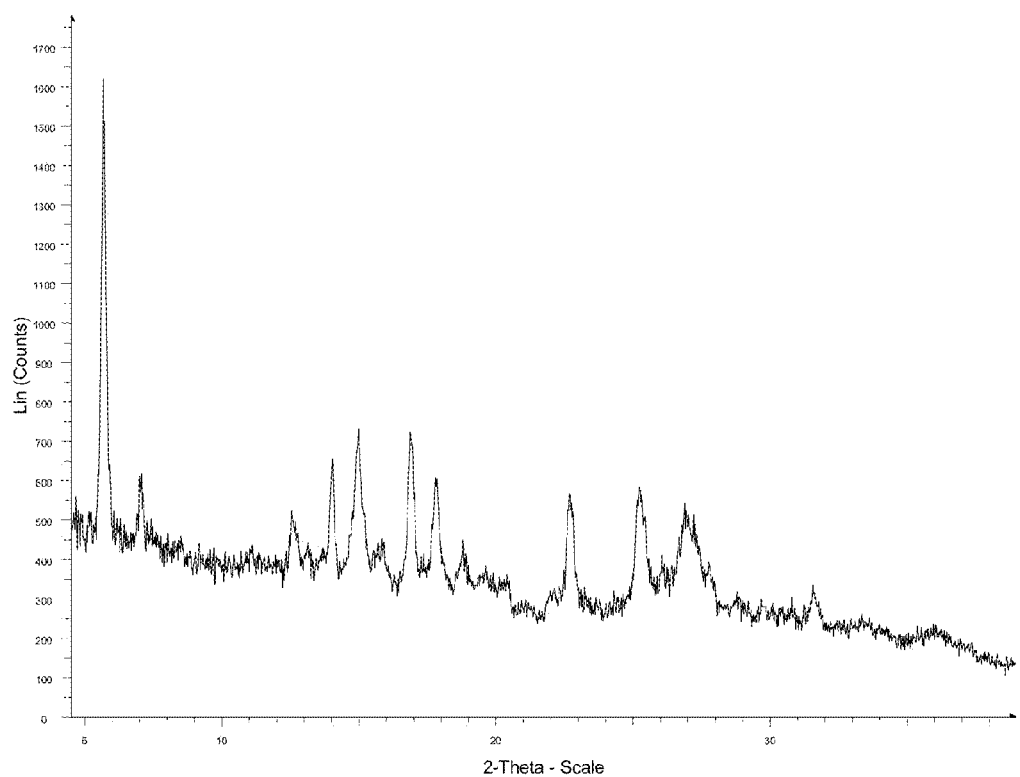

FIGURE 1E: Compound I-1 • hydrochloric acid • hydrate XRPD
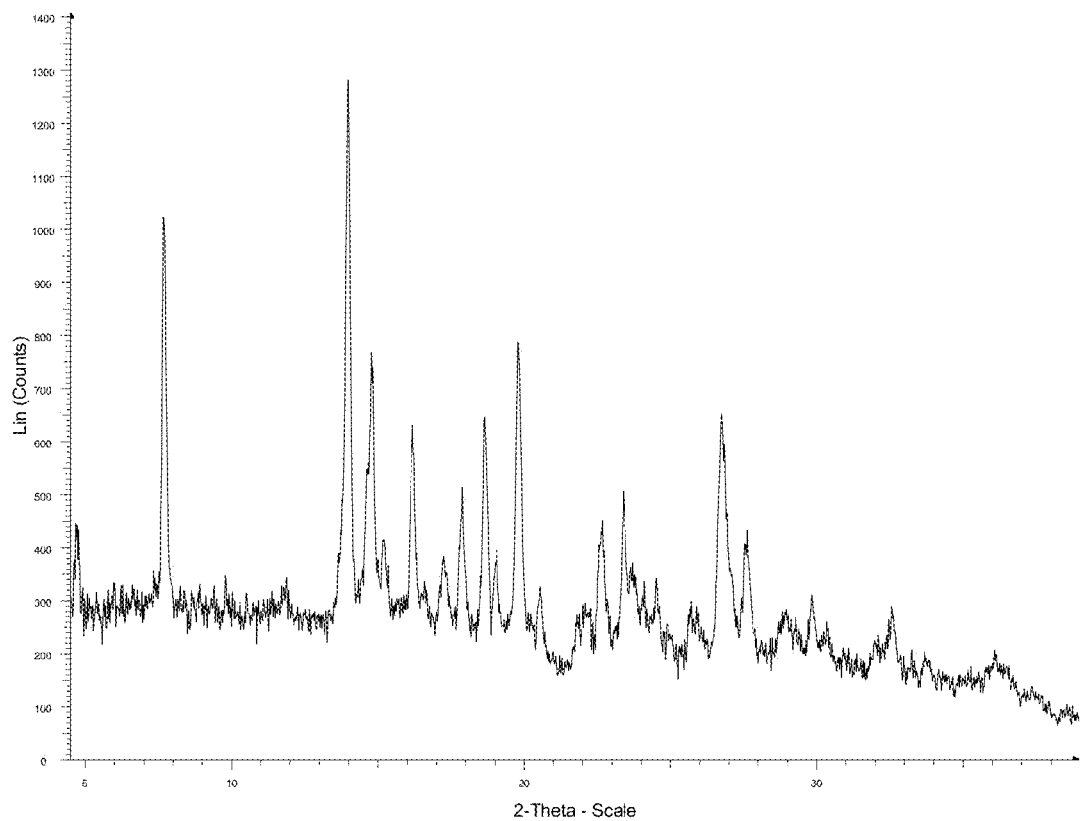
FIGURE 2E: Compound I-1 • hydrochloric acid • hydrate TGA
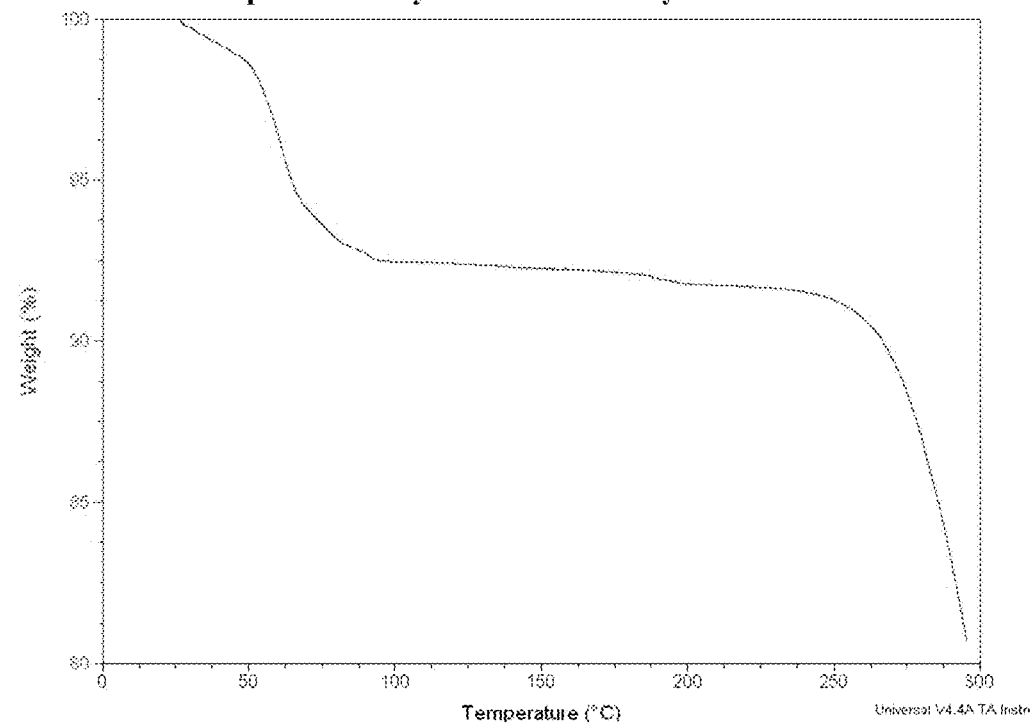

FIGURE 2B: Compound I-1 • hydrochloric acid TGA
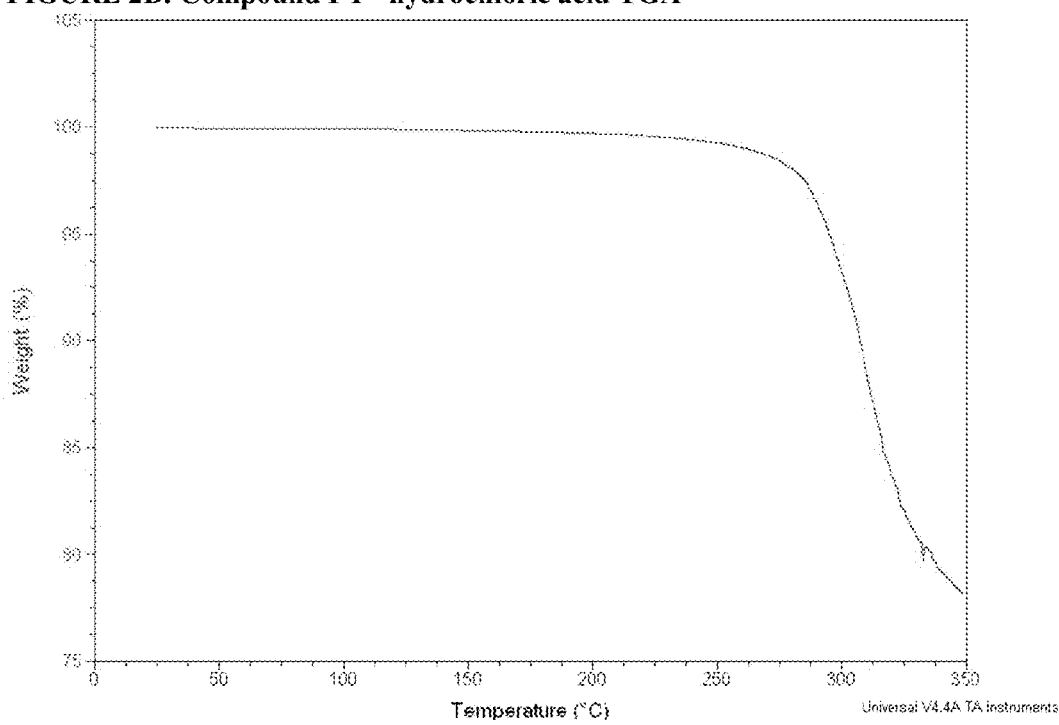
FIGURE 3B: Compound I-1 • hydrochloric acid DSC
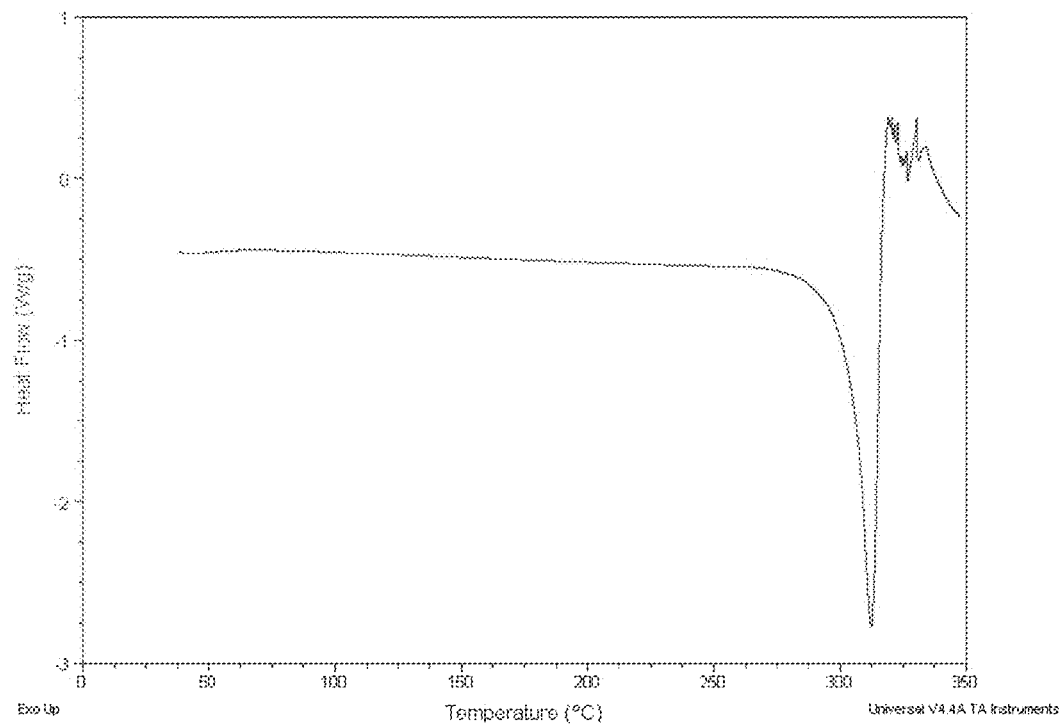

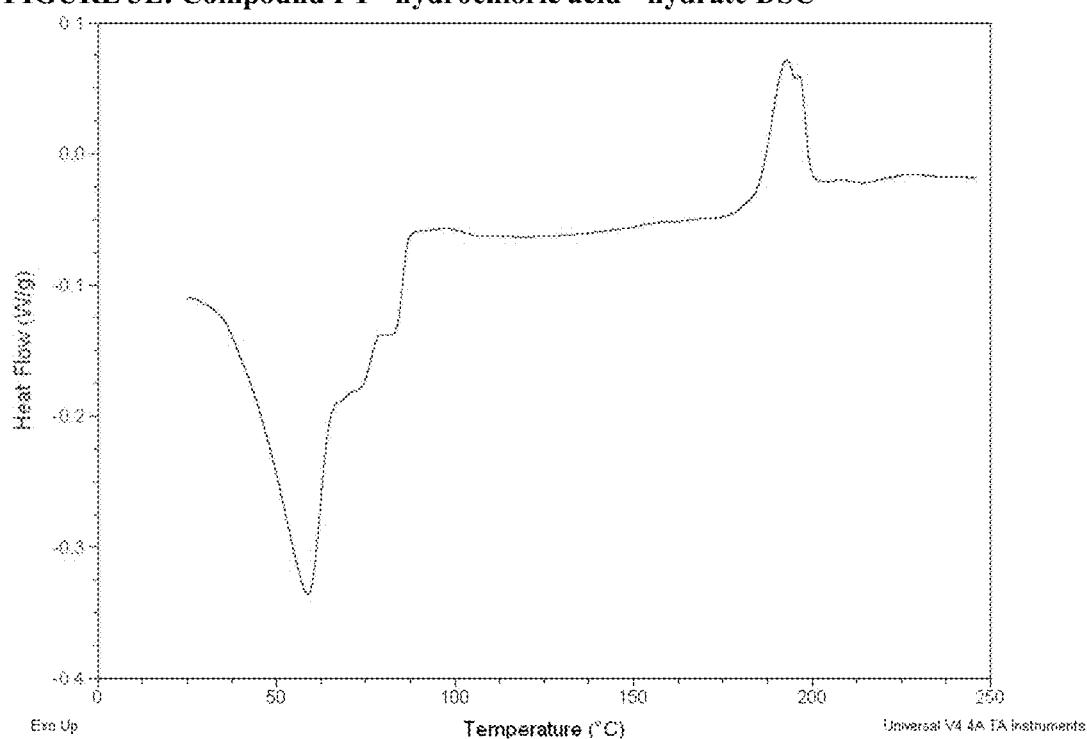
FIGURE 3E: Compound I-1 • hydrochloric acid • hydrate DSC

FIGURE 4: ORTEP plot of asymmetric unit of Compound I-1 free base single crystal structure.
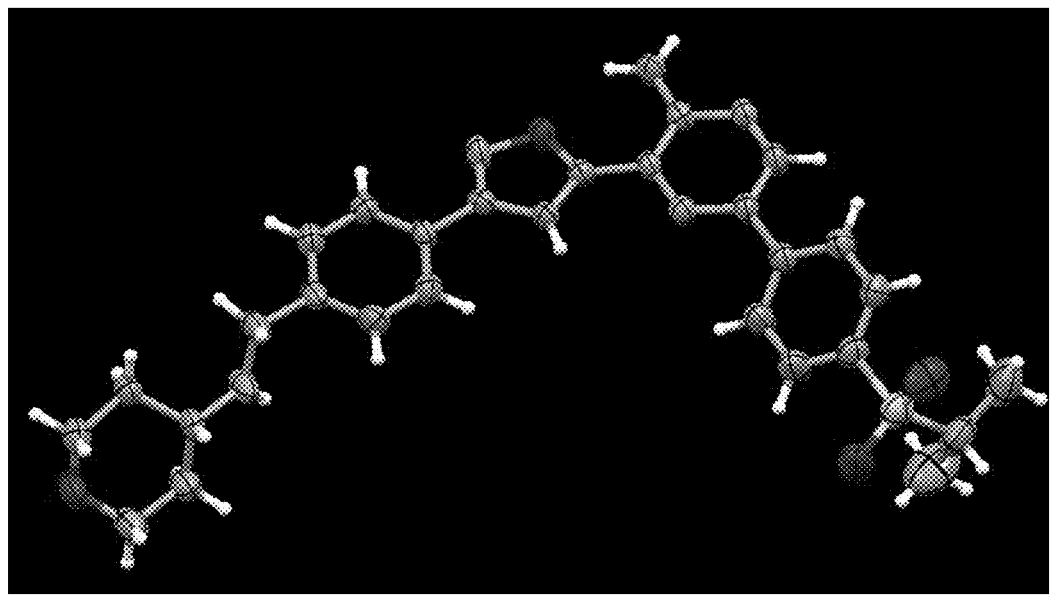
FIGURE 5: ORTEP plot of asymmetric unit of Compound I-1 • hydrochloric acid
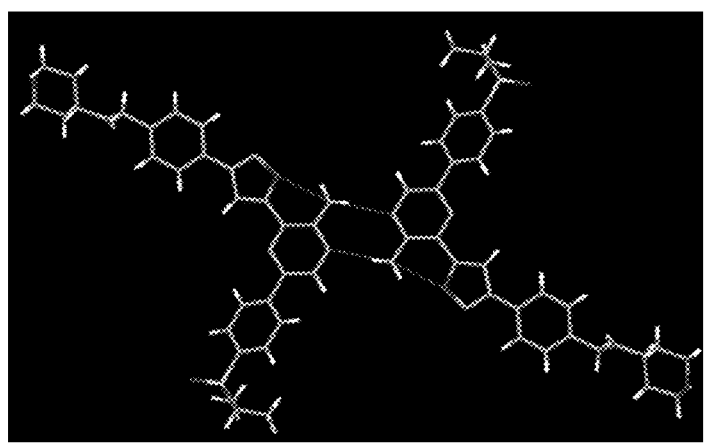
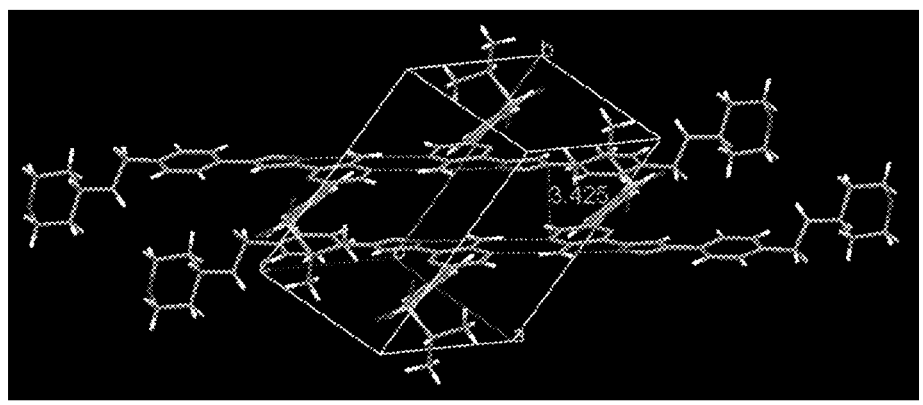

FIGURE 6: Mouse PO PK in tumor
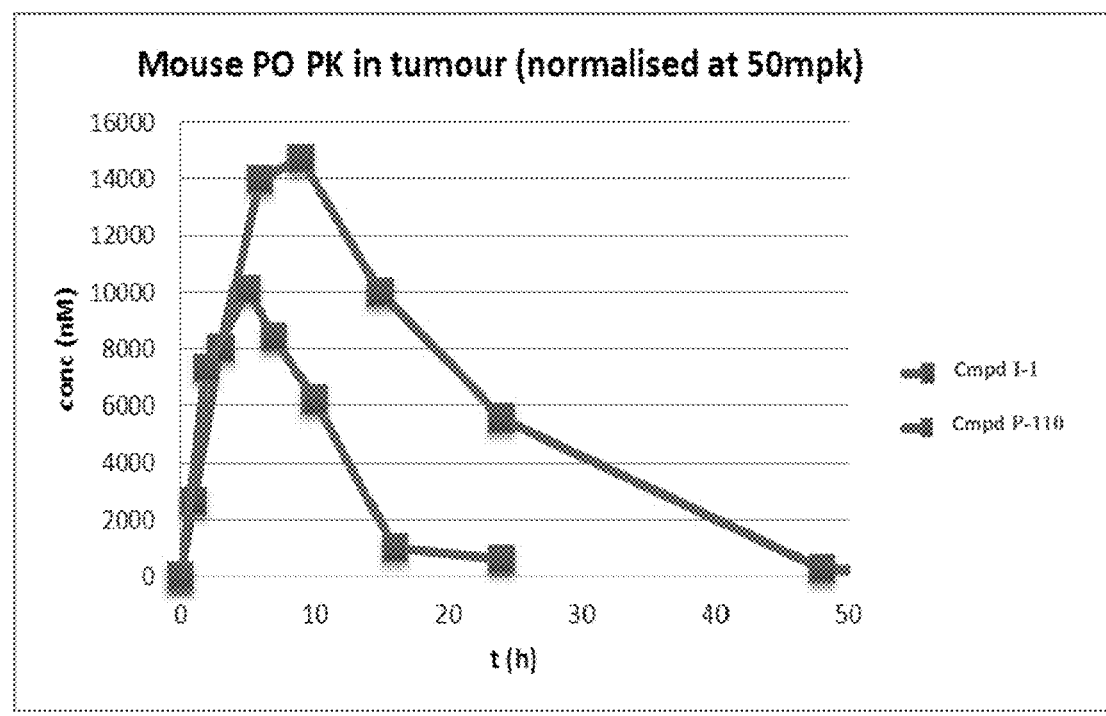

COMPOUNDS USEFUL AS INHIBITORS OF ATR KINASE

CROSS REFERENCE TO RELATED APPLICATIONS

The present application claims the benefit under 35 U.S.C. §119(e) of U.S. provisional application No. 61/541,861 filed on Sep. 30, 2011; U.S. provisional application No. 61/554,174 filed on Nov. 1, 2011; and U.S. provisional application No. 61/620,698 filed on Apr. 5, 2012; the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy, created on Aug. 12, 2014, is named VPI_11-129 US_Sequence Listing.txt and is 1 kilobyte in size.

BACKGROUND OF THE INVENTION

ATR ("ATM and Rad3 related") kinase is a protein kinase involved in cellular responses to DNA damage. ATR kinase acts with ATM ("ataxia telangiectasia mutated") kinase and many other proteins to regulate a cell's response to DNA damage, commonly referred to as the DNA Damage Response ("DDR"). The DDR stimulates DNA repair, promotes survival and stalls cell cycle progression by activating cell cycle checkpoints, which provide time for repair. Without the DDR, cells are much more sensitive to DNA damage and readily die from DNA lesions induced by endogenous cellular processes such as DNA replication or exogenous DNA damaging agents commonly used in cancer therapy.

Healthy cells can rely on a host of different proteins for DNA repair including the DDR kinase ATR. In some cases these proteins can compensate for one another by activating functionally redundant DNA repair processes. On the contrary, many cancer cells harbour defects in some of their DNA repair processes, such as ATM signaling, and therefore display a greater reliance on their remaining intact DNA repair proteins which include ATR.

In addition, many cancer cells express activated oncogenes or lack key tumour suppressors, and this can make these cancer cells prone to dysregulated phases of DNA replication which in turn cause DNA damage. ATR has been implicated as a critical component of the DDR in response to disrupted DNA replication. As a result, these cancer cells are more dependent on ATR activity for survival than healthy cells. Accordingly, ATR inhibitors may be useful for cancer treatment, either used alone or in combination with DNA damaging agents, because they shut down a DNA repair mechanism that is more important for cellular survival in many cancer cells than in healthy normal cells.

In fact, disruption of ATR function (e.g. by gene deletion) has been shown to promote cancer cell death both in the absence and presence of DNA damaging agents. This suggests that ATR inhibitors may be effective both as single agents and as potent sensitizers to radiotherapy or genotoxic chemotherapy.

ATR peptide can be expressed and isolated using a variety of methods known in the literature (see e.g., Ünsal-Kaçmaz et al, *PNAS* 99: 10, pp 6673-6678, May 14, 2002; see also Kumagai et al. *Cell* 124, pp 943-955, Mar. 10, 2006; Unsal-Kacmaz et al. *Molecular and Cellular Biology*, February 2004, p 1292-1300; and Hall-Jackson et al. *Oncogene* 1999, 18, 6707-6713).

For all of these reasons, there is a need for the development of potent and selective ATR inhibitors for the treatment of cancer, either as single agents or as combination therapies with radiotherapy or genotoxic chemotherapy.

DESCRIPTION OF THE FIGURES

FIG. 1A: X-ray powder diffractogram of Compound I-1 free base

FIG. 2A: Thermal gravimetric analysis (TGA) trace of Compound I-1 free base

FIG. 3A: Differential scanning calorimetry trace of Compound I-1 free base

FIG. 1B: X-ray powder diffractogram of Compound I-1•hydrochloric acid

FIG. 2B: Thermal gravimetric analysis (TGA) trace of Compound I-1•hydrochloric acid FIG. 3B: Differential scanning calorimetry trace of Compound I-1•hydrochloric acid FIG. 1C: X-ray powder diffractogram of Compound I-1•hydrate FIG. 2C: Thermal gravimetric analysis (TGA) trace of Compound I-1•hydrate FIG. 3C: Differential scanning calorimetry trace of Compound I-1•hydrate FIG. 1D: X-ray powder diffractogram of Compound I-1•2-hydrochloric acid•1.5$H_2O$ FIG. 1E: X-ray powder diffractogram of Compound I-1•hydrochloric acid•hydrate FIG. 2E: Thermal gravimetric analysis (TGA) trace of Compound I-1•hydrochloric acid•hydrate FIG. 3E: Differential scanning calorimetry trace of Compound I-1•hydrochloric acid•hydrate FIG. 4: ORTEP plot of asymmetric unit of Compound I-1 free base single crystal structure.

FIG. 5: Crystal Structure of Compound I-1•hydrochloric acid

FIG. 6: Mouse PO/PK in tumor

SUMMARY OF THE INVENTION

The compounds of the invention are very potent ATR inhibitors. Furthermore, compared with compounds in the prior art, these compounds have a surprisingly good pK profile, such as low clearance, low volume of distribution, and good oral exposure. These compounds demonstrate surprisingly good single agent activity in vitro. These compounds also show surprising synergy with other cancer agents, such as cisplatin, in in vitro models. These compounds are effective in promoting regression of tumors in various mouse models of cancer.

DETAILED DESCRIPTION OF THE INVENTION

One aspect of the invention provides a compound of Formula I-1:

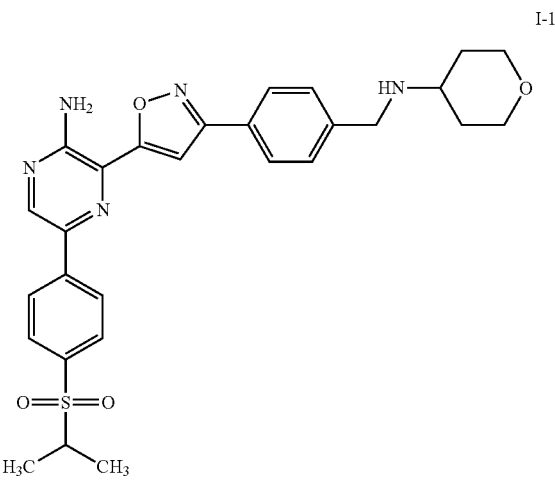 [SMILES: CC(C)S(=O)(=O)c1ccc(-c2cnc(N)c(-c3cc(-c4ccc(CNC5CCOCC5)cc4)no3)n2)cc1]

or a pharmaceutically acceptable salt thereof.

Another aspect of the present invention provides a compound of Formula II:

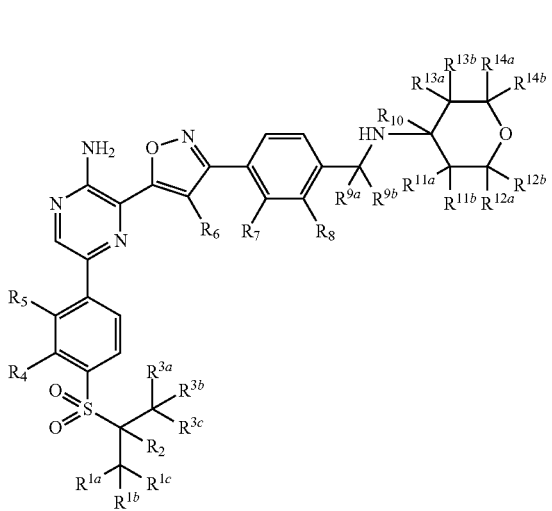

or a pharmaceutically acceptable salt thereof, wherein each $R^{1a}$, $R^{1b}$, $R^{1c}$, $R^2$, $R^{3a}$, $R^{3b}$, $R^{3c}$, $R^4$, $R^5$, $R^6$, $R^7$, $R^8$, $R^{9a}$, $R^{9b}$, $R^{10}$, $R^{11a}$, $R^{11b}$, $R^{12a}$, $R^{12b}$, $R^{13a}$, $R^{13b}$, $R^{14a}$, and $R^{14b}$ is independently hydrogen or deuterium, and at least one of $R^{1a}$, $R^{1b}$, $R^{1c}$, $R^2$, $R^{3a}$, $R^{3b}$, $R^{3c}$, $R^4$, $R^5$, $R^6$, $R^7$, $R^8$, $R^{9a}$, $R^{9b}$, $R^{10}$, $R^{11a}$, $R^{11b}$, $R^{12a}$, $R^{12b}$, $R^{13a}$, $R^{13b}$, $R^{14a}$, or $R^{14b}$ is deuterium.

In one embodiment, $R^{1a}$, $R^{1b}$, $R^{1c}$, $R^2$, $R^{3a}$, $R^{3b}$, and $R^{3c}$ are the same. In some embodiments, $R^{1a}$, $R^{1b}$, $R^{1c}$, $R^2$, $R^{3a}$, $R^{3b}$, and $R^{3c}$ are deuterium, and $R^4$, $R^5$, $R^6$, $R^7$, $R^8$, $R^{9a}$, $R^{9b}$, $R^{10}$, $R^{11a}$, $R^{11b}$, $R^{12a}$, $R^{12b}$, $R^{13a}$, $R^{13b}$, $R^{14a}$, and $R^{14b}$ are deuterium or hydrogen. In another embodiment, $R^{1a}$, $R^{1b}$, $R^{1c}$, $R^2$, $R^{3a}$, $R^{3b}$ and $R^{3c}$ are deuterium, and $R^4$, $R^5$, $R^6$, $R^7$, $R^8$, $R^{9a}$, $R^{9b}$, $R^{10}$, $R^{11a}$, $R^{11b}$, $R^{12a}$, $R^{12b}$, $R^{13a}$, $R^{13b}$, $R^{14a}$, and $R^{14b}$ are hydrogen.

In other embodiments, $R^2$ is deuterium, and $R^{1a}$, $R^{1b}$, $R^{1c}$, $R^{3a}$, $R^{3b}$, $R^{3c}$, $R^4$, $R^5$, $R^6$, $R^7$, $R^8$, $R^{9a}$, $R^{9b}$, $R^{10}$, $R^{11a}$, $R^{11b}$, $R^{12a}$, $R^{12b}$, $R^{13a}$, $R^{13b}$, $R^{14a}$, and $R^{14b}$ are deuterium or hydrogen. In another embodiment, $R^2$ is deuterium, and $R^{1a}$, $R^{1b}$, $R^{1c}$, $R^{3a}$, $R^{3b}$, $R^{3c}$, $R^4$, $R^5$, $R^6$, $R^7$, $R^8$, $R^{9a}$, $R^{9b}$, $R^{10}$, $R^{11a}$, $R^{11b}$, $R^{12a}$, $R^{12b}$, $R^{13a}$, $R^{13b}$, $R^{14a}$, and $R^{14b}$ are hydrogen.

In another embodiment, $R^6$ is deuterium, and $R^{1a}$, $R^{1b}$, $R^{1c}$, $R^2$, $R^{3a}$, $R^{3b}$, $R^{3c}$, $R^4$, $R^5$, $R^7$, $R^8$, $R^{9a}$, $R^{9b}$, $R^{10}$, $R^{11a}$, $R^{11b}$, $R^{12a}$, $R^{12b}$, $R^{13a}$, $R^{13b}$, $R^{14a}$, and $R^{14b}$ are deuterium or hydrogen. In yet another embodiment, $R^6$ is deuterium, and $R^{1a}$, $R^{1b}$, $R^{1c}$, $R^2$, $R^{3a}$, $R^{3b}$, $R^{3c}$, $R^4$, $R^5$, $R^7$, $R^8$, $R^{9a}$, $R^{9b}$, $R^{10}$, $R^{11a}$, $R^{11b}$, $R^{12a}$, $R^{12b}$, $R^{13a}$, $R^{13b}$, $R^{14a}$, and $R^{14b}$ are hydrogen.

In another embodiment, $R^{9a}$ and $R^{9b}$ are the same. In other embodiments, $R^{9a}$ and $R^{9b}$ are deuterium, and $R^{1a}$, $R^{1b}$, $R^{1c}$, $R^2$, $R^{3a}$, $R^{3b}$, $R^{3c}$, $R^4$, $R^5$, $R^6$, $R^7$, $R^8$, $R^{10}$, $R^{11a}$, $R^{11b}$, $R^{12a}$, $R^{12b}$, $R^{13a}$, $R^{13b}$, $R^{14a}$, and $R^{14b}$ are deuterium or hydrogen. In some embodiments, $R^{9a}$ and $R^{9b}$ are deuterium, and $R^{1a}$, $R^{1b}$, $R^{1c}$, $R^2$, $R^{3a}$, $R^{3b}$, $R^{3c}$, $R^4$, $R^5$, $R^6$, $R^7$, $R^8$, $R^{10}$, $R^{11a}$, $R^{11b}$, $R^{12a}$, $R^{12b}$, $R^{13a}$, $R^{13b}$, $R^{14a}$, and $R^{14b}$ are hydrogen.

In another embodiment, $R^7$ is deuterium, and $R^{1a}$, $R^{1b}$, $R^{1c}$, $R^2$, $R^{3a}$, $R^{3b}$, $R^{3c}$, $R^4$, $R^5$, $R^6$, $R^8$, $R^{9a}$, $R^{9b}$, $R^{10}$, $R^{11a}$, $R^{11b}$, $R^{12a}$, $R^{12b}$, $R^{13a}$, $R^{13b}$, $R^{14a}$, and $R^{14b}$ are deuterium or hydrogen. In other embodiments, $R^7$ is deuterium, and $R^{1a}$, $R^{1b}$, $R^{1c}$, $R^2$, $R^{3a}$, $R^{3b}$, $R^{3c}$, $R^4$, $R^5$, $R^6$, $R^8$, $R^{9a}$, $R^{9b}$, $R^{10}$, $R^{11a}$, $R^{11b}$, $R^{12a}$, $R^{12b}$, $R^{13a}$, $R^{13b}$, $R^{14a}$, and $R^{14b}$ are hydrogen.

In yet another embodiment, $R^8$ is deuterium, and $R^{1a}$, $R^{1b}$, $R^{1c}$, $R^2$, $R^{3a}$, $R^{3b}$, $R^{3c}$, $R^4$, $R^5$, $R^6$, $R^7$, $R^{9a}$, $R^{9b}$, $R^{10}$, $R^{11a}$, $R^{11b}$, $R^{12a}$, $R^{12b}$, $R^{13a}$, $R^{13b}$, $R^{14a}$, and $R^{14b}$ are deuterium or hydrogen. In another embodiment, $R^8$ is deuterium, and $R^{1a}$, $R^{1b}$, $R^{1c}$, $R^2$, $R^{3a}$, $R^{3b}$, $R^{3c}$, $R^4$, $R^5$, $R^6$, $R^7$, $R^{9a}$, $R^{9b}$, $R^{10}$, $R^{11a}$, $R^{11b}$, $R^{12a}$, $R^{12b}$, $R^{13a}$, $R^{13b}$, $R^{14a}$, and $R^{14b}$ are hydrogen.

In another embodiment, $R^{1a}$, $R^{1b}$, $R^{1c}$, $R^{3a}$, $R^{3b}$, and $R^{3c}$ are the same. In some embodiments, $R^{1a}$, $R^{1b}$, $R^{1c}$, $R^{3a}$, $R^{3b}$, and $R^{3c}$ are deuterium and $R^2$, $R^4$, $R^5$, $R^6$, $R^7$, $R^8$, $R^{9a}$, $R^{9b}$, $R^{10}$, $R^{11a}$, $R^{11b}$, $R^{12a}$, $R^{12b}$, $R^{13a}$, $R^{13b}$, $R^{14a}$, and $R^{14b}$ are deuterium or hydrogen. In some embodiments, $R^{1a}$, $R^{1b}$, $R^{1c}$, $R^{3a}$, $R^{3b}$, and $R^{3c}$ are deuterium, and $R^2$, $R^4$, $R^5$, $R^6$, $R^7$, $R^8$, $R^{9a}$, $R^{9b}$, $R^{10}$, $R^{11a}$, $R^{11b}$, $R^{12a}$, $R^{12b}$, $R^{13a}$, $R^{13b}$, $R^{14a}$, and $R^{14b}$ are hydrogen.

In yet another embodiment, $R^4$ is deuterium, and $R^{1a}$, $R^{1b}$, $R^{1c}$, $R^2$, $R^{3a}$, $R^{3b}$, $R^{3c}$, $R^5$, $R^6$, $R^7$, $R^8$, $R^{9a}$, $R^{9b}$, $R^{10}$, $R^{11a}$, $R^{11b}$, $R^{12a}$, $R^{12b}$, $R^{13a}$, $R^{13b}$, $R^{14a}$, and $R^{14b}$ are deuterium or hydrogen. In other embodiments, $R^4$ is deuterium, and $R^{1a}$, $R^{1b}$, $R^{1c}$, $R^2$, $R^{3a}$, $R^{3b}$, $R^{3c}$, $R^5$, $R^6$, $R^7$, $R^8$, $R^{9a}$, $R^{9b}$, $R^{10}$, $R^{11a}$, $R^{11b}$, $R^{12a}$, $R^{12b}$, $R^{13a}$, $R^{13b}$, $R^{14a}$, and $R^{14b}$ are hydrogen.

In another embodiment, $R^5$ is deuterium, and $R^{1a}$, $R^{1b}$, $R^{1c}$, $R^2$, $R^{3a}$, $R^{3b}$, $R^{3c}$, $R^4$, $R^6$, $R^7$, $R^8$, $R^{9a}$, $R^{9b}$, $R^{10}$, $R^{11a}$, $R^{11b}$, $R^{12a}$, $R^{12b}$, $R^{13a}$, $R^{13b}$, $R^{14a}$, and $R^{14b}$ are deuterium or hydrogen. In yet another embodiment, $R^5$ is deuterium, and $R^{1a}$, $R^{1b}$, $R^{1c}$, $R^2$, $R^{3a}$, $R^{3b}$, $R^{3c}$, $R^4$, $R^6$, $R^7$, $R^8$, $R^{9a}$, $R^{9b}$, $R^{10}$, $R^{11a}$, $R^{11b}$, $R^{12a}$, $R^{12b}$, $R^{13a}$, $R^{13b}$, $R^{14a}$, and $R^{14b}$ are hydrogen.

In some embodiments, at least one of $R^{9a}$ or $R^{9b}$ are deuterium, and $R^{1a}$, $R^{1b}$, $R^{1c}$, $R^2$, $R^{3a}$, $R^{3b}$, $R^{3c}$, $R^4$, $R^5$, $R^6$, $R^7$, $R^8$, $R^{10}$, $R^{11a}$, $R^{11b}$, $R^{12a}$, $R^{12b}$, $R^{13a}$, $R^{13b}$, $R^{14a}$, and $R^{14b}$ are deuterium or hydrogen. In other embodiments, at least one of $R^{9a}$ or $R^{9b}$ are deuterium, and $R^{1a}$, $R^{1b}$, $R^{1c}$, $R^2$, $R^{3a}$, $R^{3b}$, $R^{3c}$, $R^4$, $R^5$, $R^6$, $R^7$, $R^8$, $R^{10}$, $R^{11a}$, $R^{11b}$, $R^{12a}$, $R^{12b}$, $R^{13a}$, $R^{13b}$, $R^{14a}$, and $R^{14b}$ are hydrogen.

In yet another embodiment, $R^{10}$ is deuterium, and $R^{1a}$, $R^{1b}$, $R^{1c}$, $R^2$, $R^{3a}$, $R^{3b}$, $R^{3c}$, $R^4$, $R^5$, $R^6$, $R^7$, $R^8$, $R^{9a}$, $R^{9b}$, $R^{11a}$, $R^{11b}$, $R^{12a}$, $R^{12b}$, $R^{13a}$, $R^{13b}$, $R^{14a}$, and $R^{14b}$ are deuterium or hydrogen. In other embodiments, $R^{10}$ is deuterium, and $R^{1a}$, $R^{1b}$, $R^{1c}$, $R^2$, $R^{3a}$, $R^{3b}$, $R^{3c}$, $R^4$, $R^5$, $R^6$, $R^7$, $R^8$, $R^{9a}$, $R^{9b}$, $R^{11a}$, $R^{11b}$, $R^{12a}$, $R^{12b}$, $R^{13a}$, $R^{13b}$, $R^{14a}$, and $R^{14b}$ are hydrogen.

In some embodiments, $R^{11a}$, $R^{11b}$, $R^{13a}$, and $R^{13b}$ are the same. In another embodiment, $R^{11a}$, $R^{11b}$, $R^{13a}$, and $R^{13b}$ are deuterium, and $R^{1a}$, $R^{1b}$, $R^{1c}$, $R^2$, $R^{3a}$, $R^{3b}$, $R^{3c}$, $R^4$, $R^5$, $R^6$, $R^7$, $R^8$, $R^{9a}$, $R^{9b}$, $R^{10}$, $R^{12a}$, $R^{12b}$, $R^{14a}$, and $R^{14b}$ are deuterium or hydrogen. In yet another embodiment, $R^{11a}$, $R^{11b}$, $R^{13a}$, and $R^{13b}$ are deuterium, and $R^{1a}$, $R^{1b}$, $R^{1c}$, $R^2$, $R^{3a}$, $R^{3b}$, $R^{3c}$, $R^4$, $R^5$, $R^6$, $R^7$, $R^8$, $R^{9a}$, $R^{9b}$, $R^{10}$, $R^{12a}$, $R^{12b}$, $R^{14a}$, and $R^{14b}$ are hydrogen.

In other embodiments, $R^{12a}$, $R^{12b}$, $R^{14a}$, and $R^{14b}$ are the same. In some embodiments, $R^{12a}$, $R^{12b}$, $R^{14a}$, and $R^{14b}$ are deuterium, and $R^{1a}$, $R^{1b}$, $R^{1c}$, $R^2$, $R^{3a}$, $R^{3b}$, $R^{3c}$, $R^4$, $R^5$, $R^6$, $R^7$, $R^8$, $R^{9a}$, $R^{9b}$, $R^{10}$, $R^{11a}$, $R^{11b}$, $R^{13a}$, and $R^{13b}$ are deuterium or hydrogen. In yet another embodiment, $R^{12a}$, $R^{12b}$, $R^{14a}$, and $R^{14b}$ are deuterium, and $R^{1a}$, $R^{1b}$, $R^{1c}$, $R^2$, $R^{3a}$, $R^{3b}$, $R^{3c}$, $R^4$, $R^5$, $R^6$, $R^7$, $R^8$, $R^{9a}$, $R^{9b}$, $R^{10}$, $R^{11a}$, $R^{11b}$, $R^{13a}$, and $R^{13b}$ are hydrogen.

In another embodiment, $R^{1a}$, $R^{1b}$, $R^{1c}$, $R^2$, $R^{3a}$, $R^{3b}$, $R^{3c}$, and $R^6$ are the same. In other embodiments, $R^{1a}$, $R^{1b}$, $R^{1c}$, $R^2$, $R^{3a}$, $R^{3b}$, $R^{3c}$, and $R^6$ are deuterium, and $R^4$, $R^5$, $R^7$, $R^8$, $R^{9a}$, $R^{9b}$, $R^{10}$, $R^{11a}$, $R^{11b}$, $R^{12a}$, $R^{12b}$, $R^{13a}$, $R^{13b}$, $R^{14a}$, and $R^{14b}$ are deuterium or hydrogen. In yet another embodiment, $R^{1a}$, $R^{1b}$, $R^{1c}$, $R^2$, $R^{3a}$, $R^{3b}$, $R^{3c}$, and $R^6$ are deuterium, and $R^4$, $R^5$, $R^7$, $R^8$, $R^{9a}$, $R^{9b}$, $R^{10}$, $R^{11a}$, $R^{11b}$, $R^{12a}$, $R^{12b}$, $R^{13a}$, $R^{13b}$, $R^{14a}$, and $R^{14b}$ are hydrogen.

In some embodiments, $R^7$, $R^{9a}$, and $R^{9b}$ are the same. In another embodiment, $R^7$, $R^{9a}$, and $R^{9b}$ are deuterium, and $R^{1a}$, $R^{1b}$, $R^{1c}$, $R^2$, $R^{3a}$, $R^{3b}$, $R^{3c}$, $R^4$, $R^5$, $R^6$, $R^8$, $R^{10}$, $R^{11a}$, $R^{11b}$, $R^{12a}$, $R^{12b}$, $R^{13a}$, $R^{13b}$, $R^{14a}$, and $R^{14b}$ are deuterium or hydrogen. In other embodiments, $R^7$, $R^{9a}$, and $R^{9b}$ are deuterium, and $R^{1a}$, $R^{1b}$, $R^{1c}$, $R^2$, $R^{3a}$, $R^{3b}$, $R^{3c}$, $R^4$, $R^5$, $R^6$, $R^8$, $R^{10}$, $R^{11a}$, $R^{11b}$, $R^{12a}$, $R^{12b}$, $R^{13a}$, $R^{13b}$, $R^{14a}$, and $R^{14b}$ are hydrogen.

In another embodiment, $R^2$ and $R^8$ are the same. In yet another embodiment, $R^2$ and $R^8$ are the same, and $R^{1a}$, $R^{1b}$, $R^{1c}$, $R^{3a}$, $R^{3b}$, $R^{3c}$, $R^4$, $R^5$, $R^6$, $R^7$, $R^{9a}$, $R^{9b}$, $R^{10}$, $R^{11a}$, $R^{11b}$, $R^{12a}$, $R^{12b}$, $R^{13a}$, $R^{13b}$, $R^{14a}$, and $R^{14b}$ are deuterium or hydrogen. In some embodiments, $R^{1a}$, $R^{1b}$, $R^{1c}$, $R^{3a}$, $R^{3b}$, $R^{3c}$, $R^4$, $R^5$, $R^6$, $R^7$, $R^{9a}$, $R^{9b}$, $R^{10}$, $R^{11a}$, $R^{11b}$, $R^{12a}$, $R^{12b}$, $R^{13a}$, $R^{13b}$, $R^{14a}$, and $R^{14b}$ are hydrogen.

In other embodiments, $R^{1a}$, $R^{1b}$, $R^{1c}$, $R^{3a}$, $R^{3b}$, $R^{3c}$, and $R^{10}$ are the same. In another embodiment, $R^{1a}$, $R^{1b}$, $R^{1c}$, $R^{3a}$, $R^{3b}$, $R^{3c}$, and $R^{10}$ are deuterium, and $R^2$, $R^4$, $R^5$, $R^6$, $R^7$, $R^8$, $R^{9a}$, $R^{9b}$, $R^{11a}$, $R^{11b}$, $R^{12a}$, $R^{12b}$, $R^{13a}$, $R^{13b}$, $R^{14a}$, and $R^{14b}$ are deuterium or hydrogen. In some embodiments, $R^{1a}$, $R^{1b}$, $R^{1c}$, $R^{3a}$, $R^{3b}$, $R^{3c}$, and $R^{10}$ are deuterium, and $R^2$, $R^4$, $R^5$, $R^6$, $R^7$, $R^8$, $R^{9a}$, $R^{9b}$, $R^{11a}$, $R^{11b}$, $R^{12a}$, $R^{12b}$, $R^{13a}$, $R^{13b}$, $R^{14a}$, and $R^{14b}$ are hydrogen.

In yet another embodiment, $R^4$, $R^{11a}$, $R^{11b}$, $R^{13a}$, and $R^{13b}$ are the same. In other embodiments, $R^4$, $R^{11a}$, $R^{11b}$, $R^{13a}$, and $R^{13b}$ are deuterium, and $R^{1a}$, $R^{1b}$, $R^{1c}$, $R^2$, $R^{3a}$, $R^{3b}$, $R^{3c}$, $R^5$, $R^6$, $R^7$, $R^8$, $R^{9a}$, $R^{9b}$, $R^{10}$, $R^{12a}$, $R^{12b}$, $R^{14a}$, and $R^{14b}$ are deuterium or hydrogen. In some embodiments, $R^4$, $R^{11a}$, $R^{11b}$, $R^{13a}$, and $R^{13b}$ are deuterium, and $R^{1a}$, $R^{1b}$, $R^{1c}$, $R^2$, $R^{3a}$, $R^{3b}$, $R^{3c}$, $R^5$, $R^6$, $R^7$, $R^8$, $R^{9a}$, $R^{9b}$, $R^{10}$, $R^{12a}$, $R^{12b}$, $R^{14a}$, and $R^{14b}$ are hydrogen.

In other embodiments, $R^{12a}$, $R^{12b}$, $R^{14a}$, $R^{14b}$, and at least one of $R^{9a}$ or $R^{9b}$ are the same. In another embodiment, $R^{12a}$, $R^{12b}$, $R^{14a}$, $R^{14b}$, and at least one of $R^{9a}$ or $R^{9b}$ are deuterium, and $R^{1a}$, $R^{1b}$, $R^{1c}$, $R^2$, $R^{3a}$, $R^{3b}$, $R^4$, $R^5$, $R^6$, $R^7$, $R^8$, $R^{10}$, $R^{11a}$, $R^{11b}$, $R^{13a}$, and $R^{13b}$ are deuterium or hydrogen. In yet another embodiment, $R^{12a}$, $R^{12b}$, $R^{14a}$, $R^{14b}$, and at least one of $R^{9a}$ or $R^{9b}$ are deuterium, and $R^{1a}$, $R^{1b}$, $R^{1c}$, $R^2$, $R^{3a}$, $R^{3b}$, $R^{3c}$, $R^4$, $R^5$, $R^6$, $R^7$, $R^8$, $R^{10}$, $R^{11a}$, $R^{11b}$, $R^{13a}$, and $R^{13b}$ are hydrogen.

In some embodiments, $R^{1a}$, $R^{1b}$, $R^{1c}$, $R^2$, $R^{3a}$, $R^{3b}$, $R^{3c}$, $R^6$, and $R^{10}$ are the same. In yet another embodiment, $R^{1a}$, $R^{1b}$, $R^{1c}$, $R^2$, $R^{3a}$, $R^{3b}$, $R^{3c}$, $R^6$, and $R^{10}$ are deuterium, and $R^4$, $R^5$, $R^7$, $R^8$, $R^{9a}$, $R^{9b}$, $R^{11a}$, $R^{11b}$, $R^{12a}$, $R^{12b}$, $R^{13a}$, $R^{13b}$, $R^{14a}$, and $R^{14b}$ are deuterium or hydrogen. In other embodiments, $R^{1a}$, $R^{1b}$, $R^{1c}$, $R^2$, $R^{3a}$, $R^{3b}$, $R^{3c}$, $R^6$, and $R^{10}$ are deuterium, and $R^4$, $R^5$, $R^7$, $R^8$, $R^{9a}$, $R^{9b}$, $R^{11a}$, $R^{11b}$, $R^{12a}$, $R^{12b}$, $R^{13a}$, $R^{13b}$, $R^{14a}$, and $R^{14b}$ are hydrogen.

In another embodiment, $R^2$, $R^7$, $R^{9a}$, and $R^{9b}$ are the same. In yet another embodiment, $R^2$, $R^7$, $R^{9a}$, and $R^{9b}$ are deuterium, $R^{1a}$, $R^{1b}$, $R^{1c}$, $R^{3a}$, $R^{3b}$, $R^{3c}$, $R^4$, $R^5$, $R^6$, $R^8$, $R^{10}$, $R^{11a}$, $R^{11b}$, $R^{12a}$, $R^{12b}$, $R^{13a}$, $R^{13b}$, $R^{14a}$, and $R^{14b}$ are hydrogen or deuterium. In other embodiments, $R^2$, $R^7$, $R^{9a}$, and $R^{9b}$ are deuterium, and $R^{1a}$, $R^{1b}$, $R^{1c}$, $R^{3a}$, $R^{3b}$, $R^{3c}$, $R^4$, $R^5$, $R^6$, $R^8$, $R^{10}$, $R^{11a}$, $R^{11b}$, $R^{12a}$, $R^{12b}$, $R^{13a}$, $R^{13b}$, $R^{14a}$, and $R^{14b}$ are hydrogen.

In some embodiments, $R^{1a}$, $R^{1b}$, $R^{1c}$, $R^2$, $R^{3a}$, $R^{3b}$, $R^{3c}$, $R^5$, $R^6$, $R^7$, $R^{9a}$, $R^{9b}$, $R^{11a}$, $R^{11b}$, $R^{13a}$, and $R^{13b}$ are the same. In another embodiment $R^{1a}$, $R^{1b}$, $R^{1c}$, $R^2$, $R^{3a}$, $R^{3b}$, $R^{3c}$, $R^5$, $R^6$, $R^7$, $R^{9a}$, $R^{9b}$, $R^{11a}$, $R^{11b}$, $R^{13a}$, and $R^{13b}$ are deuterium, and $R^4$, $R^8$, $R^{10}$, $R^{12a}$, $R^{12b}$, $R^{14a}$, and $R^{14b}$ are deuterium or hydrogen. In yet another embodiment, $R^{1a}$, $R^{1b}$, $R^{1c}$, $R^2$, $R^{3a}$, $R^{3b}$, $R^{3c}$, $R^5$, $R^6$, $R^7$, $R^{9a}$, $R^{9b}$, $R^{11a}$, $R^{11b}$, $R^{13a}$, and $R^{13b}$ are deuterium, and $R^4$, $R^8$, $R^{10}$, $R^{12a}$, $R^{12b}$, $R^{14a}$, and $R^{14b}$ are hydrogen.

In some embodiments, the variables are as depicted in the compounds of the disclosure including compounds in Table 1 below.

TABLE 1

I-1

II-2

II-3

TABLE 1-continued
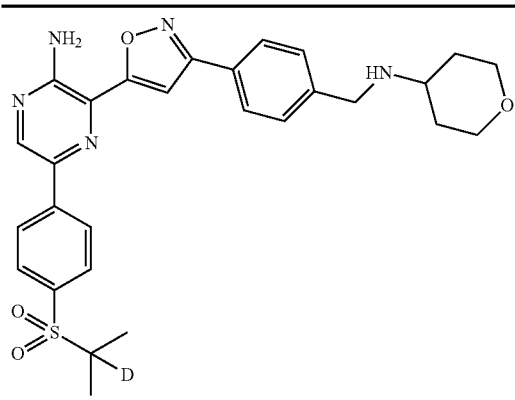
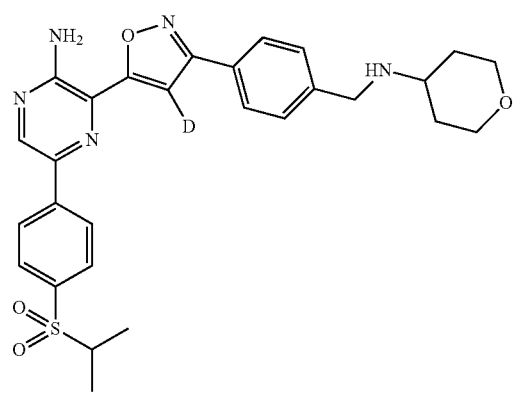 [SMILES: [2H]c1c(-c2ccc(CNC3CCOCC3)cc2)noc1-c1nc(-c2ccc(S(=O)(=O)C(C)C)cc2)cnc1N]
II-4
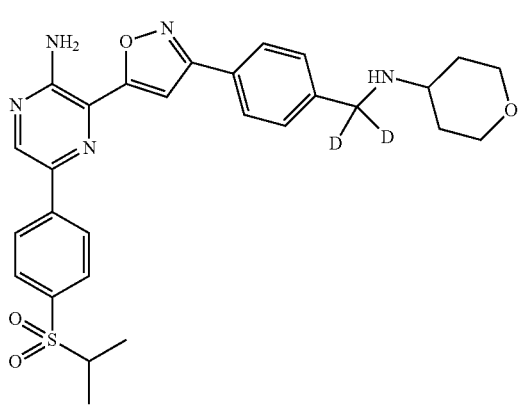 [SMILES: [2H]C([2H])(NC1CCOCC1)c1ccc(-c2cc(-c3nc(-c4ccc(S(=O)(=O)C(C)C)cc4)cnc3N)on2)cc1]
II-5
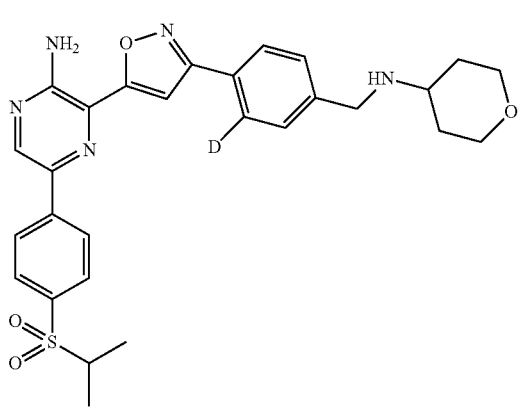 [SMILES: [2H]c1cc(CNC2CCOCC2)ccc1-c1cc(-c2nc(-c3ccc(S(=O)(=O)C(C)C)cc3)cnc2N)on1]
II-6
TABLE 1-continued
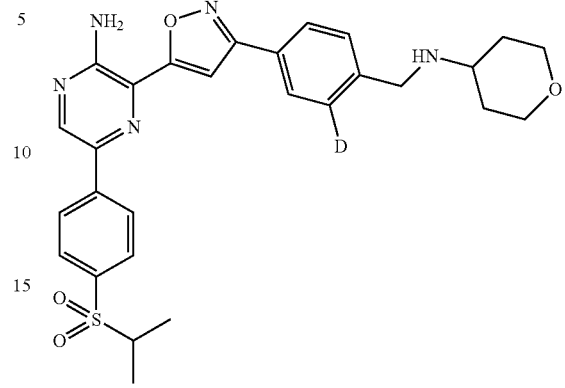 [SMILES: [2H]c1cc(-c2cnc(N)c(-c3cc(-c4ccc(CNC5CCOCC5)cc4)no3)n2)ccc1S(=O)(=O)C(C)C]
II-7
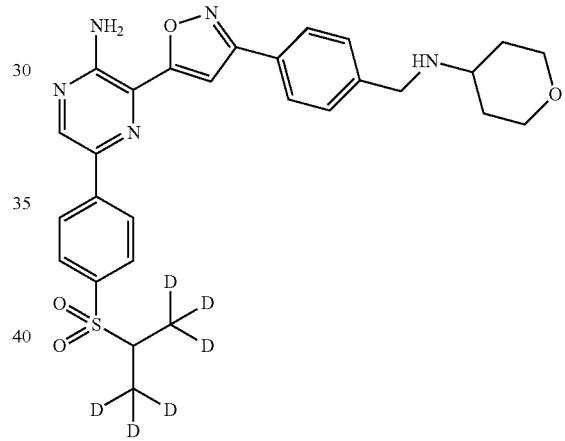
II-8
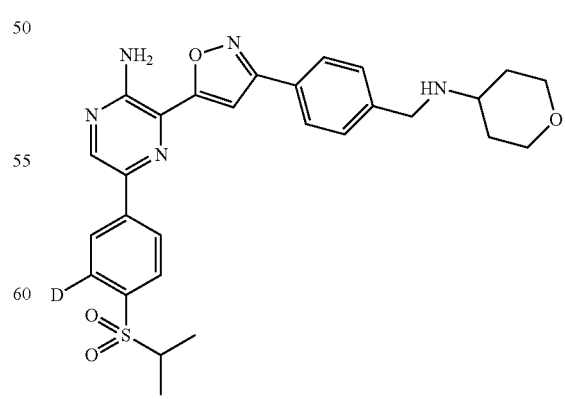
II-9
II-10

TABLE 1-continued
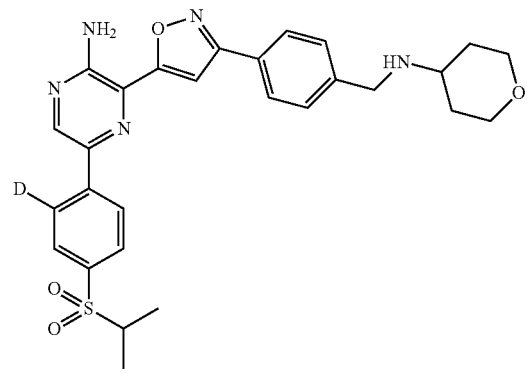 [SMILES: [2H]c1cc(S(=O)(=O)C(C)C)ccc1-c1cnc(N)c(-c2cc(-c3ccc(CNC4CCOCC4)cc3)no2)n1]
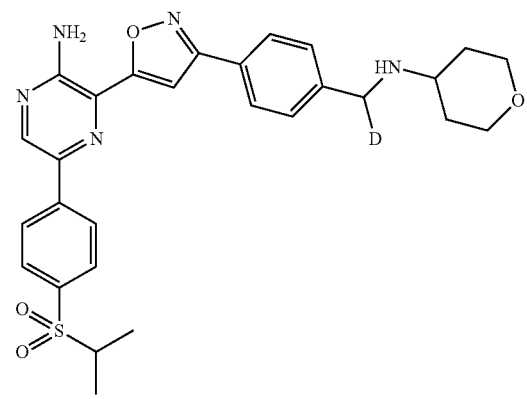 [SMILES: [2H]C(NC1CCOCC1)c1ccc(-c2cc(-c3nc(-c4ccc(S(=O)(=O)C(C)C)cc4)cnc3N)on2)cc1]
II-11
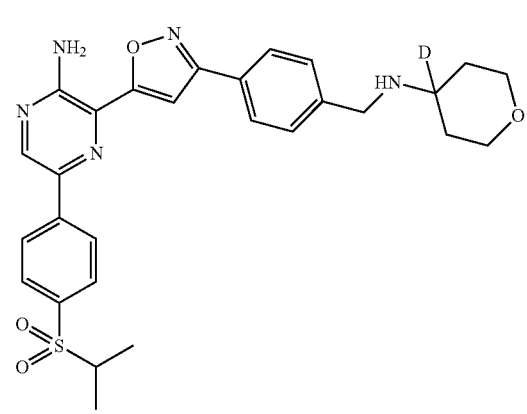 [SMILES: [2H]C1(NCc2ccc(-c3cc(-c4nc(-c5ccc(S(=O)(=O)C(C)C)cc5)cnc4N)on3)cc2)CCOCC1]
II-12
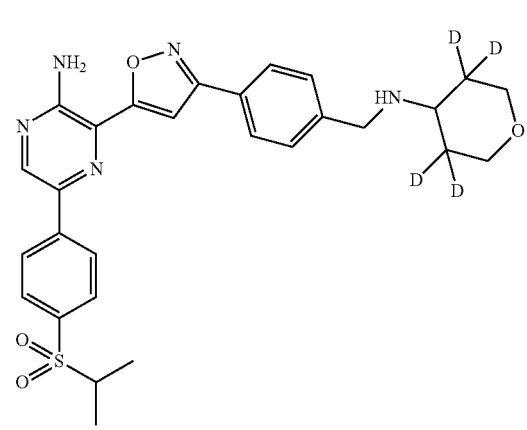 [SMILES: [2H]C1([2H])COCC([2H])([2H])C1NCc1ccc(-c2cc(-c3nc(-c4ccc(S(=O)(=O)C(C)C)cc4)cnc3N)on2)cc1]
II-13
TABLE 1-continued
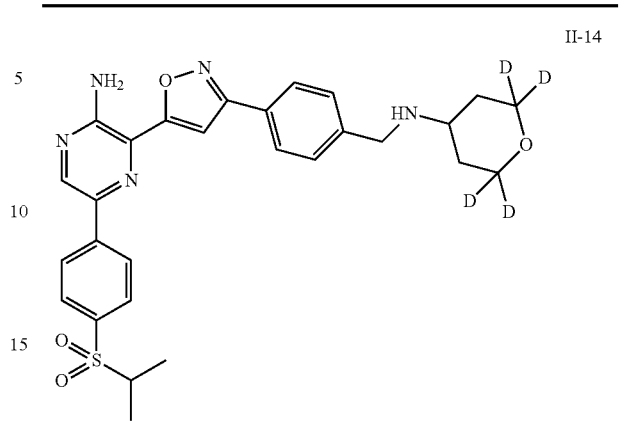
II-14
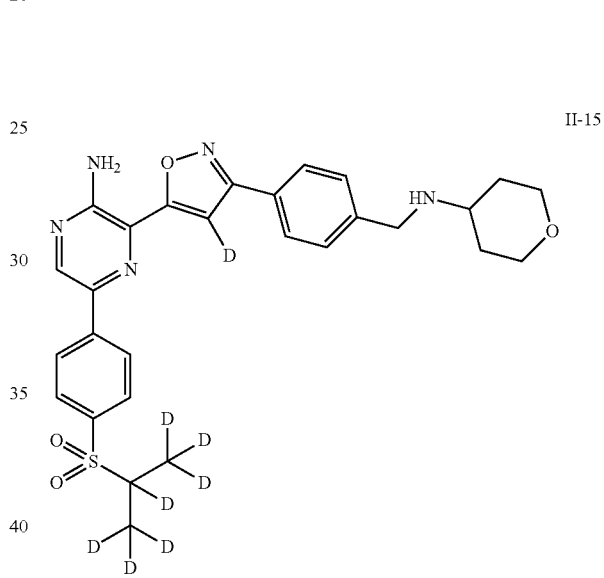
II-15
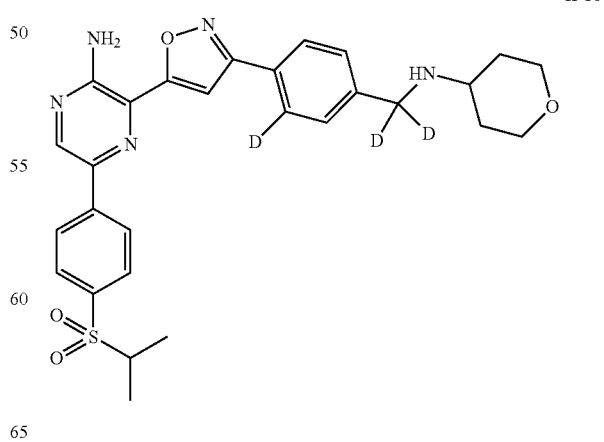
II-16
II-17

TABLE 1-continued

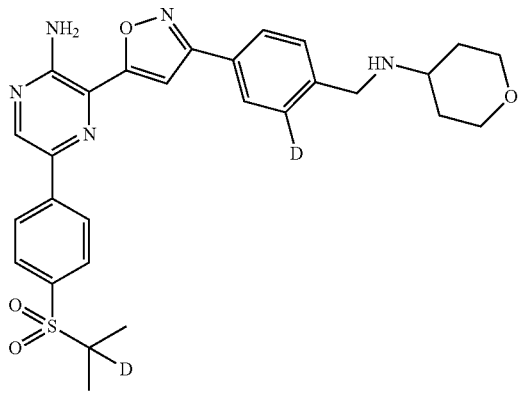 [SMILES: [2H]c1cc(-c2cc(-c3nc(-c4ccc(S(=O)(=O)C([2H])(C)C)cc4)cnc3N)on2)ccc1CNC1CCOCC1]
II-17

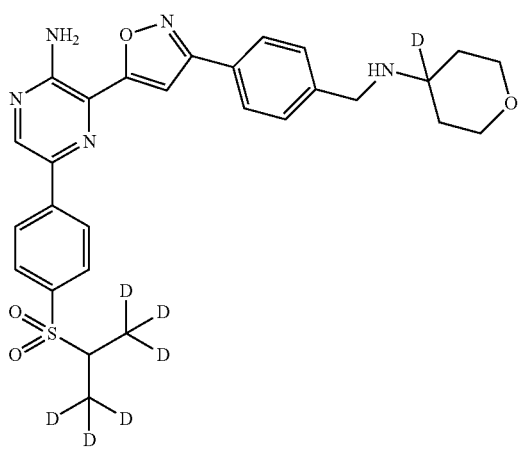 [SMILES: [2H]C1(NCc2ccc(-c3cc(-c4nc(-c5ccc(S(=O)(=O)C(C([2H])([2H])[2H])C([2H])([2H])[2H])cc5)cnc4N)on3)cc2)CCOCC1]
II-18

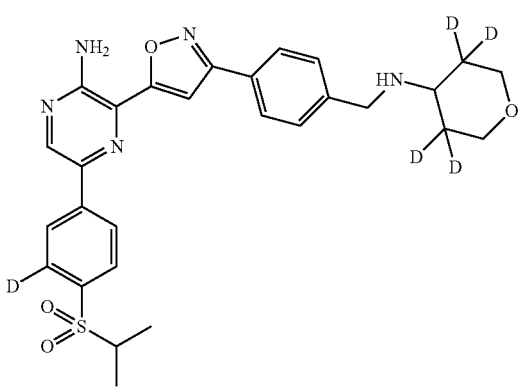 [SMILES: [2H]c1cc(-c2cnc(N)c(-c3cc(-c4ccc(CNC5C([2H])([2H])COCC5([2H])[2H])cc4)no3)n2)ccc1S(=O)(=O)C(C)C]
II-19

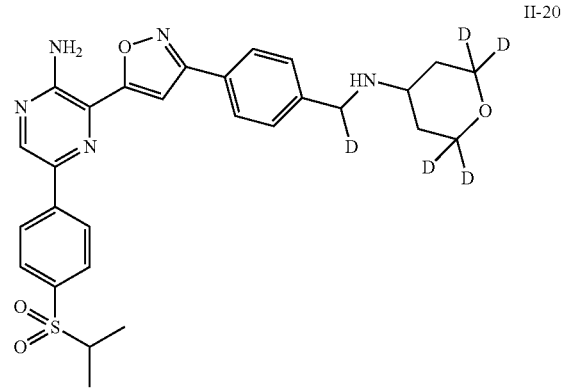
II-20

TABLE 1-continued

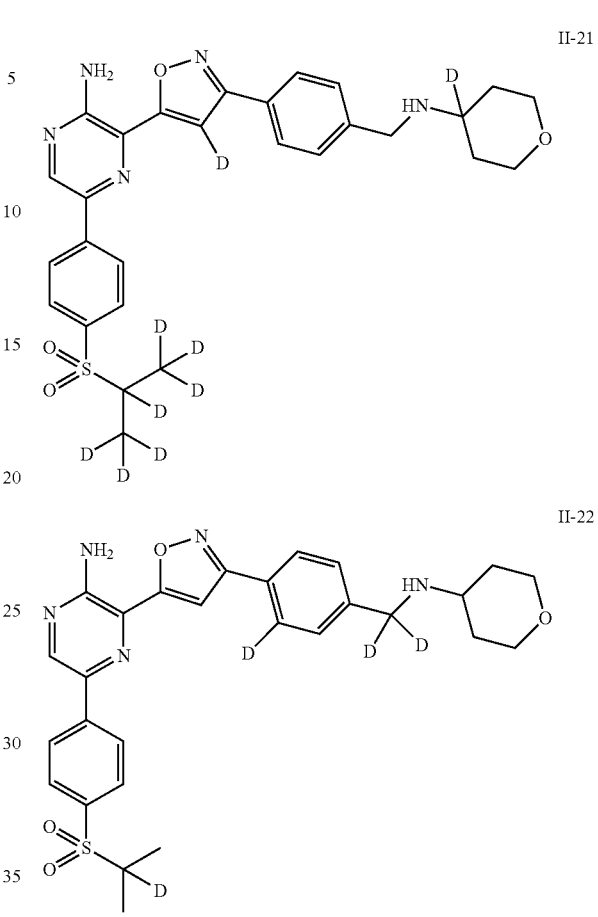
II-21

II-22

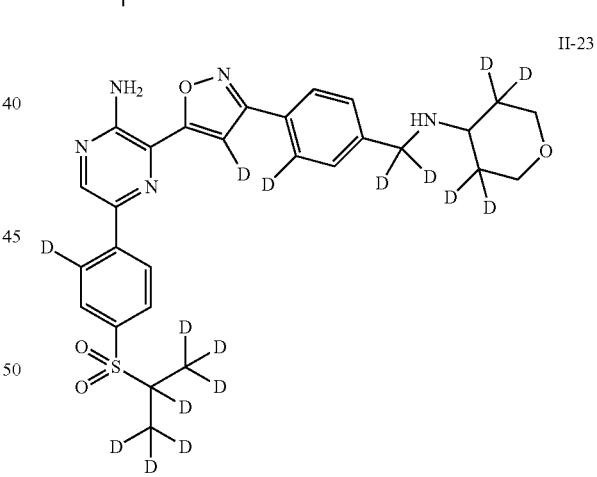
II-23

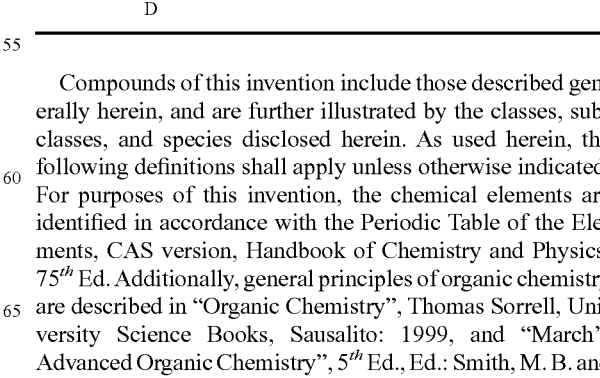

Compounds of this invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

As described herein, compounds of the invention may optionally be substituted with one or more substituents, such as are illustrated generally herein, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

Unless otherwise indicated, a substituent connected by a bond drawn from the center of a ring means that the substituent can be bonded to any position in the ring. In example i below, for instance, $J^1$ can be bonded to any position on the pyridyl ring. For bicyclic rings, a bond drawn through both rings indicates that the substituent can be bonded from any position of the bicyclic ring. In example 11 below, for instance, $J^1$ can be bonded to the 5-membered ring (on the nitrogen atom, for instance), and to the 6-membered ring.

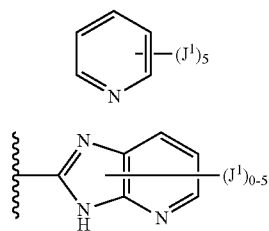

The term "stable", as used herein, refers to compounds that are not substantially altered when subjected to conditions to allow for their production, detection, recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched), branched, or cyclic, substituted or unsubstituted hydrocarbon chain that is completely saturated or that contains one or more units of unsaturation that has a single point of attachment to the rest of the molecule.

Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Aliphatic groups may be linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl. Aliphatic groups may also be cyclic, or have a combination of linear or branched and cyclic groups. Examples of such types of aliphatic groups include, but are not limited to cyclopropyl, cyclobutyl, cyclopentyl, cyclohexyl, cyclohexenyl, —CH$_2$-cyclopropyl, CH$_2$CH$_2$CH(CH$_3$)-cyclohexyl.

The term "cycloaliphatic" (or "carbocycle" or "carbocyclyl") refers to a monocyclic C$_3$-C$_8$ hydrocarbon or bicyclic C$_8$-C$_{12}$ hydrocarbon that is completely saturated or that contains one or more units of unsaturation, but which is not aromatic, that has a single point of attachment to the rest of the molecule wherein any individual ring in said bicyclic ring system has 3-7 members. Examples of cycloaliphatic groups include, but are not limited to, cycloalkyl and cycloalkenyl groups. Specific examples include, but are not limited to, cyclohexyl, cyclopropenyl, and cyclobutyl.

The term "heterocycle", "heterocyclyl", or "heterocyclic" as used herein means non-aromatic, monocyclic, bicyclic, or tricyclic ring systems in which one or more ring members are an independently selected heteroatom. In some embodiments, the "heterocycle", "heterocyclyl", or "heterocyclic" group has three to fourteen ring members in which one or more ring members is a heteroatom independently selected from oxygen, sulfur, nitrogen, or phosphorus, and each ring in the system contains 3 to 7 ring members.

Examples of heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

Cyclic groups, (e.g. cycloaliphatic and heterocycles), can be linearly fused, bridged, or spirocyclic.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation. As would be known by one of skill in the art, unsaturated groups can be partially unsaturated or fully unsaturated. Examples of partially unsaturated groups include, but are not limited to, butene, cyclohexene, and tetrahydropyridine. Fully unsaturated groups can be aromatic, anti-aromatic, or non-aromatic. Examples of fully unsaturated groups include, but are not limited to, phenyl, cyclooctatetraene, pyridyl, thienyl, and 1-methylpyridin-2(1H)-one.

The term "alkoxy", or "thioalkyl", as used herein, refers to an alkyl group, as previously defined, attached through an oxygen ("alkoxy") or sulfur ("thioalkyl") atom.

The terms "haloalkyl", "haloalkenyl", "haloaliphatic", and "haloalkoxy" mean alkyl, alkenyl or alkoxy, as the case may be, substituted with one or more halogen atoms. This term includes perfluorinated alkyl groups, such as —CF$_3$ and —CF$_2$CF$_3$.

The terms "halogen", "halo", and "hal" mean F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring".

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Examples of heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

It shall be understood that the term "heteroaryl" includes certain types of heteroaryl rings that exist in equilibrium between two different forms. More specifically, for example, species such hydropyridine and pyridinone (and likewise hydroxypyrimidine and pyrimidinone) are meant to be encompassed within the definition of "heteroaryl."

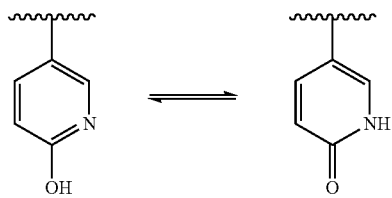 [SMILES: *c1ccc(O)nc1 ; *c1ccc(=O)[nH]c1]

The term "protecting group" and "protective group" as used herein, are interchangeable and refer to an agent used to temporarily block one or more desired functional groups in a compound with multiple reactive sites. In certain embodiments, a protecting group has one or more, or preferably all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Examples of protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agent used to temporarily block one or more desired nitrogen reactive sites in a multifunctional compound. Preferred nitrogen protecting groups also possess the characteristics exemplified for a protecting group above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, a methylene unit of an alkyl or aliphatic chain is optionally replaced with another atom or group. Examples of such atoms or groups include, but are not limited to, nitrogen, oxygen, sulfur, —C(O)—, —C(=N—CN)—, —C(=NR)—, —C(=NOR)—, —SO—, and —SO$_2$—. These atoms or groups can be combined to form larger groups. Examples of such larger groups include, but are not limited to, —OC(O)—, —C(O)CO—, —CO$_2$—, —C(O)NR—, —C(=N—CN), —NRCO—, —NRC(O)O—, —SO$_2$NR—, —NRSO$_2$—, —NRC(O)NR—, —OC(O)NR—, and —NRSO$_2$NR—, wherein R is, for example, H or C$_{1-6}$aliphatic. It should be understood that these groups can be bonded to the methylene units of the aliphatic chain via single, double, or triple bonds. An example of an optional replacement (nitrogen atom in this case) that is bonded to the aliphatic chain via a double bond would be —CH$_2$CH=N—CH$_3$. In some cases, especially on the terminal end, an optional replacement can be bonded to the aliphatic group via a triple bond. One example of this would be CH$_2$CH$_2$CH$_2$C≡N. It should be understood that in this situation, the terminal nitrogen is not bonded to another atom.

It should also be understood that, the term "methylene unit" can also refer to branched or substituted methylene units. For example, in an isopropyl moiety [—CH(CH$_3$)$_2$], a nitrogen atom (e.g. NR) replacing the first recited "methylene unit" would result in dimethylamine [—N(CH$_3$)$_2$]. In instances such as these, one of skill in the art would understand that the nitrogen atom will not have any additional atoms bonded to it, and the "R" from "NR" would be absent in this case.

Unless otherwise indicated, the optional replacements form a chemically stable compound. Optional replacements can occur both within the chain and/or at either end of the chain; i.e. both at the point of attachment and/or also at the terminal end. Two optional replacements can also be adjacent to each other within a chain so long as it results in a chemically stable compound. For example, a C$_3$ aliphatic can be optionally replaced by 2 nitrogen atoms to form —C—N=N. The optional replacements can also completely replace all of the carbon atoms in a chain. For example, a C$_3$ aliphatic can be optionally replaced by —NR—, —C(O)—, and —NR— to form —NRC(O)NR— (a urea).

Unless otherwise indicated, if the replacement occurs at the terminal end, the replacement atom is bound to a hydrogen atom on the terminal end. For example, if a methylene unit of —CH$_2$CH$_2$CH$_3$ were optionally replaced with —O—, the resulting compound could be —OCH$_2$CH$_3$, —CH$_2$OCH$_3$, or —CH$_2$CH$_2$OH. It should be understood that if the terminal atom does not contain any free valence electrons, then a hydrogen atom is not required at the terminal end (e.g., —CH$_2$CH$_2$CH=O or —CH$_2$CH$_2$C=N).

Unless otherwise indicated, structures depicted herein are also meant to include all isomeric (e.g., enantiomeric, diastereomeric, geometric, conformational, and rotational) forms of the structure. For example, the R and S configurations for each asymmetric center, (Z) and (E) double bond isomers, and (Z) and (E) conformational isomers are included in this invention. As would be understood to one skilled in the art, a substituent can freely rotate around any rotatable bonds. For example, a substituent drawn as

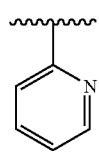

also represents

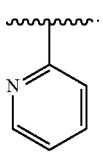

Therefore, single stereochemical isomers as well as enantiomeric, diastereomeric, geometric, conformational, and rotational mixtures of the present compounds are within the scope of the invention.

Unless otherwise indicated, all tautomeric forms of the compounds of the invention are within the scope of the invention.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

"D" and "d" both refer to deuterium.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

Solid Forms

Another aspect of this invention provides solid forms of the compounds of this invention. On embodiment provides a solid form of a compound of formula I-1:

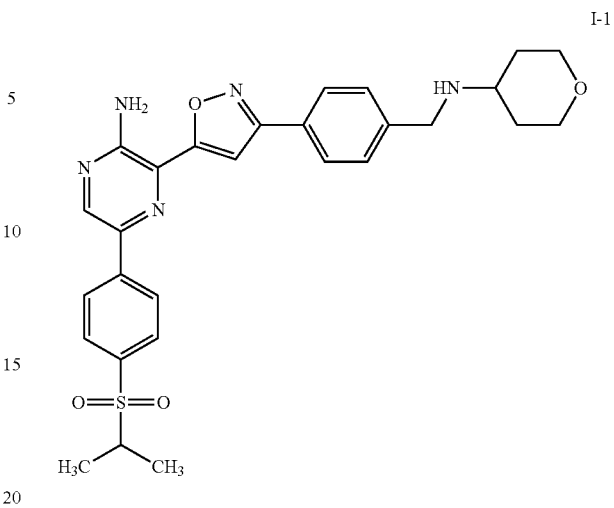

wherein the form is selected from the group consisting of Compound I-1 freebase, Compound I-1•hydrochloric acid, Compound I-1 freebase hydrate, Compound I-1•2-hydrochloric acid•1.5H$_2$O, and Compound I-1•hydrochloric acid hydrate.

In some embodiments, the forms are crystalline.

One embodiment provides a crystalline Compound I-1 free base characterized by a triclinic crystal system, having a P-1 space group, and having the following unit cell dimensions in Å when measured at 120K:

a=6.7319(2) Å
b=12.3762(3) Å
c=17.2422(4) Å.

In some embodiments, crystalline Compound I-1 free base is characterized by a weight loss of from about 0.4% in a temperature range of from about 25° C. to about 350° C.

In other embodiments, crystalline Compound I-1 free base is characterized by one or more peaks expressed in 2-theta±0.2 at about 11.6, 14.3, 18.4, 22.4, and 27.9 degrees in a X-ray powder diffraction pattern obtained using Cu K alpha radiation.

In yet other embodiments, crystalline Compound I-1 free base is characterized by one or more peaks expressed in 2-theta±0.2 at the values described in the peak chart herein. In some embodiments, crystalline Compound I-1 free base is characterized by having an X-ray powder diffraction pattern substantially the same as that shown in FIG. 1A.

Another embodiment provides a crystalline Compound I-1•hydrochloric acid. In some embodiments, Compound I-1•hydrochloric acid is characterized by a weight loss of from about 0.7% in a temperature range of from about 25° C. to about 250° C. In other embodiments, Compound I-1•hydrochloric acid is characterized by one or more peaks expressed in 2-theta±0.2 at about 12.9, 15.3, 15.6, 18.2, and 23.3 degrees in a X-ray powder diffraction pattern obtained using Cu K alpha radiation. In other embodiments, Compound I-1•hydrochloric acid is characterized as having an X-ray powder diffraction pattern substantially the same as that shown in FIG. 1B.

Another embodiment provides crystalline Compound I-1 free base hydrate. In some embodiments, crystalline Compound I-1 free base hydrate is characterized by a weight loss of from about 0.95% in a temperature range of from about 25° C. to about 375° C.

In some embodiments, crystalline Compound I-1 free base hydrate is characterized by one or more peaks expressed in 2-theta±0.2 at about 8.1, 9.4, 14.6, 19.2, and 19.7 degrees in a X-ray powder diffraction pattern obtained using Cu K alpha radiation.

In another embodiment, Compound I-1 free base hydrate is characterized as having an X-ray powder diffraction pattern substantially the same as that shown in FIG. 1C.

Another embodiment provides crystalline Compound I-1•2-hydrochloric acid•1.5H$_2$O. In some embodiments, crystalline Compound I-1•2-hydrochloric acid•1.5H$_2$O is characterized by one or more peaks expressed in 2-theta±0.2 at about 7.0, 12.6, 14.0, 16.9, and 26.1 degrees in a X-ray powder diffraction pattern obtained using Cu K alpha radiation.

In some embodiments, crystalline Compound I-1•2-hydrochloric acid•1.5H$_2$O is characterized as having an X-ray powder diffraction pattern substantially the same as that shown in FIG. 1D.

Another embodiment provides crystalline Compound I•hydrochloric acid hydrate. In some embodiments, the form is characterized by a weight loss of from about 7.5% in a temperature range of from about 25° C. to about 100° C. In some embodiments, the form is characterized by one or more peaks expressed in 2-theta±0.2 at about 7.7, 16.2, 19.0, 19.8, and 23.4 degrees in a X-ray powder diffraction pattern obtained using Cu K alpha radiation.

In other embodiments, Compound I•hydrochloric acid hydrate is characterized as having an X-ray powder diffraction pattern substantially the same as that shown in FIG. 1E.

Another embodiment provides a process for preparing crystalline Compound I•hydrochloric acid comprising adding about 1.1 equivalents of HCl (aq) to a solution of Compound I-1 free base in ethanol at a temperature in a range of 20-55° C. to form crystalline Compound I-1•hydrochloric acid.

Yet another embodiment provides a process for preparing crystalline Compound I-1 free base comprising adding an aqueous solution of NaOH to a solution of Compound I-1•acid salt in ethanol at a temperature in a range of 14-42° C. to form crystalline Compound I-1 free base.

Pharmaceutically Acceptable Salts

The compounds of this invention can exist in free form for treatment, or where appropriate, as a pharmaceutically acceptable salt.

A "pharmaceutically acceptable salt" means any non-toxic salt of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of the ATR protein kinase.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. These salts can be prepared in situ during the final isolation and purification of the compounds. Acid addition salts can be prepared by 1) reacting the purified compound in its free-based form with a suitable organic or inorganic acid and 2) isolating the salt thus formed.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Base addition salts can be prepared by 1) reacting the purified compound in its acid form with a suitable organic or inorganic base and 2) isolating the salt thus formed. Salts derived from appropriate bases include alkali metal (e.g., sodium, lithium, and potassium), alkaline earth metal (e.g., magnesium and calcium), ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization.

Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate. Other acids and bases, while not in themselves pharmaceutically acceptable, may be employed in the preparation of salts useful as intermediates in obtaining the compounds of the invention and their pharmaceutically acceptable acid or base addition salts.

Abbreviations

The following abbreviations are used:

| | |
|---|---|
| ATP | adenosine triphosphate |
| Boc | tert-butyl carbamate |
| Cbz | Carboxybenzyl |
| DCM | dichloromethane |
| DMSO | dimethyl sulfoxide |
| Et$_3$N | triethylamine |
| 2-MeTHF | 2-methyltetrahydrofuran |
| NMM | N-Methyl morpholine |
| DMAP | 4-Dimethylaminopyridine |
| TMS | Trimethylsilyl |
| MTBE | methyl tertbutyl ether |
| EtOAc | ethyl acetate |
| i-PrOAc | isopropyl acetate |
| IPAC | isopropyl acetate |
| DMF | dimethylformamide |
| DIEA | diisopropylethylamine |
| TEA | triethylamine |
| t-BuONa | sodium tertbutoxide |
| K$_2$CO$_3$ | potassium carbonate |
| PG | Protecting group |
| pTSA | para-toluenesulfonic acid |
| TBAF | Tetra-n-butylammonium fluoride |
| $^1$HNMR | proton nuclear magnetic resonance |
| HPLC | high performance liquid chromatography |
| LCMS | liquid chromatography-mass spectrometry |
| TLC | thin layer chromatography |
| Rt | retention time |

Compound Uses

One aspect of this invention provides compounds that are inhibitors of ATR kinase, and thus are useful for treating or lessening the severity of a disease, condition, or disorder where ATR is implicated in the disease, condition, or disorder.

Another aspect of this invention provides compounds that are useful for the treatment of diseases, disorders, and conditions characterized by excessive or abnormal cell proliferation. Such diseases include, a proliferative or hyperproliferative disease. Examples of proliferative and hyperproliferative diseases include, without limitation, cancer and myeloproliferative disorders.

In some embodiments, said compounds are selected from the group consisting of a compound described herein. The term "cancer" includes, but is not limited to the following cancers. Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma, undifferentiated thyroid cancer, medullary thyroid carcinoma, multiple endocrine neoplasia type 2A, multiple endocrine neoplasia type 2B, familial medullary thyroid cancer, pheochromocytoma, paraganglioma; and Adrenal glands: neuroblastoma.

In some embodiments, the cancer is selected from a cancer of the lung or the pancreas. In other embodiments, the cancer is selected from lung cancer, head and neck cancer, pancreatic cancer, gastric cancer, or brain cancer. In yet other embodiments, the cancer is selected from non-small cell lung cancer, small cell lung cancer, pancreatic cancer, biliary tract cancer, head and neck cancer, bladder cancer, colorectal cancer, glioblastoma, esophageal cancer, breast cancer, hepatocellular carcinoma, or ovarian cancer.

Thus, the term "cancerous cell" as provided herein, includes a cell afflicted by any one of the above-identified conditions. In some embodiments, the cancer is selected from colorectal, thyroid, or breast cancer.

The term "myeloproliferative disorders", includes disorders such as polycythemia vera, thrombocythemia, myeloid metaplasia with myelofibrosis, hypereosinophilic syndrome, juvenile myelomonocytic leukemia, systemic mast cell disease, and hematopoietic disorders, in particular, acute-myelogenous leukemia (AML), chronic-myelogenous leukemia (CML), acute-promyelocytic leukemia (APL), and acute lymphocytic leukemia (ALL).

Pharmaceutically Acceptable Derivatives or Prodrugs

In addition to the compounds of this invention, pharmaceutically acceptable derivatives or prodrugs of the compounds of this invention may also be employed in compositions to treat or prevent the herein identified disorders.

The compounds of this invention can also exist as pharmaceutically acceptable derivatives.

A "pharmaceutically acceptable derivative" is an adduct or derivative which, upon administration to a patient in need, is capable of providing, directly or indirectly, a compound as otherwise described herein, or a metabolite or residue thereof. Examples of pharmaceutically acceptable derivatives include, but are not limited to, esters and salts of such esters.

A "pharmaceutically acceptable derivative or prodrug" means any pharmaceutically acceptable ester, salt of an ester or other derivative or salt thereof of a compound, of this invention which, upon administration to a recipient, is capable of providing, either directly or indirectly, a compound of this invention or an inhibitorily active metabolite or residue thereof. Particularly favoured derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Pharmaceutical Compositions

The present invention also provides compounds and compositions that are useful as inhibitors of ATR kinase.

One aspect of this invention provides pharmaceutically acceptable compositions that comprise any of the compounds as described herein, and optionally comprise a pharmaceutically acceptable carrier, adjuvant or vehicle.

The pharmaceutically acceptable carrier, adjuvant, or vehicle, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Combination Therapies

Another aspect of this invention is directed towards a method of treating cancer in a subject in need thereof, comprising administration of a compound of this invention or a pharmaceutically acceptable salt thereof, and an additional therapeutic agent. In some embodiments, said method comprises the sequential or co-administration of the compound or a pharmaceutically acceptable salt thereof, and the additional therapeutic agent.

In some embodiments, said additional therapeutic agent is an anti-cancer agent. In other embodiments, said additional therapeutic agent is a DNA-damaging agent. In yet other embodiments, said additional therapeutic agent is selected from radiation therapy, chemotherapy, or other agents typically used in combination with radiation therapy or chemotherapy, such as radiosensitizers and chemosensitizers. In yet other embodiments, said additional therapeutic agent is ionizing radiation.

As would be known by one of skill in the art, radiosensitizers are agents that can be used in combination with radiation therapy. Radiosensitizers work in various different ways, including, but not limited to, making cancer cells more sensitive to radiation therapy, working in synergy with radiation therapy to provide an improved synergistic effect, acting additively with radiation therapy, or protecting surrounding healthy cells from damage caused by radiation therapy. Likewise chemosensitizers are agents that can be used in combination with chemotherapy. Similarly, chemosensitizers work in various different ways, including, but not limited to, making cancer cells more sensitive to chemotherapy, working in synergy with chemotherapy to provide an improved synergistic effect, acting additively to chemotherapy, or protecting surrounding healthy cells from damage caused by chemotherapy.

Examples of DNA-damaging agents that may be used in combination with compounds of this invention include, but are not limited to Platinating agents, such as Carboplatin, Nedaplatin, Satraplatin and other derivatives; Topo I inhibitors, such as Topotecan, irinotecan/SN38, rubitecan and other derivatives; Antimetabolites, such as Folic family (Methotrexate, Pemetrexed and relatives); Purine antagonists and Pyrimidine antagonists (Thioguanine, Fludarabine, Cladribine, Cytarabine, Gemcitabine, 6-Mercaptopurine, 5-Fluorouracil (5FU) and relatives); Alkylating agents, such as Nitrogen mustards (Cyclophosphamide, Melphalan, Chlorambucil, mechlorethamine, Ifosfamide and relatives); nitrosoureas (eg Carmustine); Triazenes (Dacarbazine, temozolomide); Alkyl sulphonates (eg Busulfan); Procarbazine and Aziridines; Antibiotics, such as Hydroxyurea, Anthracyclines (doxorubicin, daunorubicin, epirubicin and other derivatives); Anthracenediones (Mitoxantrone and relatives); Streptomyces family (Bleomycin, Mitomycin C, actinomycin); and Ultraviolet light.

Other therapies or anticancer agents that may be used in combination with the inventive agents of the present invention include surgery, radiotherapy (in but a few examples, gamma-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, the DNA damaging agents listed herein, spindle poisons (Vinblastine, Vincristine, Vinorelbine, Paclitaxel), podophyllotoxins (Etoposide, Irinotecan, Topotecan), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide.

A compound of the instant invention may also be useful for treating cancer in combination with any of the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®);

dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Ferrara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); zoledronate (Zometa®) and vorinostat (Zolinza®).

For a comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Compositions for Administration into a Subject

The ATR kinase inhibitors or pharmaceutical salts thereof may be formulated into pharmaceutical compositions for administration to animals or humans. These pharmaceutical compositions, which comprise an amount of the ATR inhibitor effective to treat or prevent the diseases or conditions described herein and a pharmaceutically acceptable carrier, are another embodiment of the present invention.

The exact amount of compound required for treatment will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

In some embodiments, these compositions optionally further comprise one or more additional therapeutic agents. For example, chemotherapeutic agents or other anti-proliferative agents may be combined with the compounds of this invention to treat proliferative diseases and cancer. Examples of known agents with which these compositions can be combined are listed above under the "Combination Therapies" section and also throughout the specification. Some embodiments provide a simultaneous, separate or sequential use of a combined preparation.

Modes of Administration and Dosage Forms

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions of the present invention may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include, but are not limited to, cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of protein kinase inhibitor that may be combined with the carrier materials to produce a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

Administering with Another Agent

Depending upon the particular protein kinase-mediated conditions to be treated or prevented, additional drugs, which are normally administered to treat or prevent that condition, may be administered together with the compounds of this invention.

Those additional agents may be administered separately, as part of a multiple dosage regimen, from the protein kinase inhibitor-containing compound or composition. Alternatively, those agents may be part of a single dosage form, mixed together with the protein kinase inhibitor in a single composition.

Another aspect of this invention is directed towards a method of treating cancer in a subject in need thereof, comprising the sequential or co-administration of a compound of this invention or a pharmaceutically acceptable salt thereof, and an anti-cancer agent. In some embodiments, said anti-cancer agent is selected from Platinating agents, such as Cisplatin, Oxaliplatin, Carboplatin, Nedaplatin, or Satraplatin and other derivatives; Topo I inhibitors, such as Camptothecin, Topotecan, irinotecan/SN38, rubitecan and other derivatives; Antimetabolites, such as Folic family (Methotrexate, Pemetrexed and relatives); Purine family (Thioguanine, Fludarabine, Cladribine, 6-Mercaptopurine and relatives); Pyrimidine family (Cytarabine, Gemcitabine, 5-Fluorouracil and relatives); Alkylating agents, such as Nitrogen mustards (Cyclophosphamide, Melphalan, Chlorambucil, mechlorethamine, Ifosfamide, and relatives); nitrosoureas (e.g. Carmustine); Triazenes (Dacarbazine, temozolomide); Alkyl sulphonates (e.g. Busulfan); Procarbazine and Aziridines; Antibiotics, such as Hydroxyurea; Anthracyclines (doxorubicin, daunorubicin, epirubicin and other derivatives); Anthracenediones (Mitoxantrone and relatives); Streptomyces family (Bleomycin, Mitomycin C, actinomycin) and Ultraviolet light.

Another embodiment provides administering a compound of this invention with an additional therapeutic agent that inhibits or modulates a base excision repair protein. In some embodiments, the base excision repair protein is selected from UNG, SMUG1, MBD4, TDG, OGG1, MYH, NTH1, MPG, NEIL1, NEIL2, NEIL3 (DNA glycosylases); APE1, APEX2 (AP endonucleases); LIG1, LIG3 (DNA ligases I and III); XRCC1 (LIG3 accessory); PNK, PNKP (polynucleotide kinase and phosphatase); PARP1, PARP2 (Poly(ADP-Ribose) Polymerases); PolB, PolG (polymerases); FEN1 (endonuclease) or Aprataxin. In other embodiments, the base excision repair protein is selected from PARP1, PARP2, or PolB. In yet other embodiments, the base excision repair protein is selected from PARP1 or PARP2. In some embodiments, the agent is selected from Olaparib (also known as AZD2281 or KU-0059436), Iniparib (also known as BSI-201 or SAR240550), Veliparib (also known as ABT-888), Rucaparib (also known as PF-01367338), CEP-9722, INO-1001, MK-4827, E7016, BMN673, or AZD2461.

Biological Samples

As inhibitors of ATR kinase, the compounds and compositions of this invention are also useful in biological samples. One aspect of the invention relates to inhibiting ATR kinase activity in a biological sample, which method comprises contacting said biological sample with a compound described herein or a composition comprising said compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof. The term "compounds described herein" includes compounds of formula I-1, formula II, and other compounds within the application.

Inhibition of ATR kinase activity in a biological sample is useful for a variety of purposes that are known to one of skill in the art. Examples of such purposes include, but are not limited to, blood transfusion, organ-transplantation, and biological specimen storage.

Study of Protein Kinases

Another aspect of this invention relates to the study of protein kinases in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds as protein kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands. Detailed conditions for assaying a compound utilized in this invention as an inhibitor of ATR is set forth in the Examples below.

Another aspect of the invention provides a method for modulating enzyme activity by contacting a compound described herein with ATR kinase.

Methods of Treatment

In one aspect, the present invention provides a method for treating or lessening the severity of a disease, condition, or disorder where ATR kinase is implicated in the disease state. In another aspect, the present invention provides a method for treating or lessening the severity of an ATR kinase disease, condition, or disorder where inhibition of enzymatic activity is implicated in the treatment of the disease. In another aspect, this invention provides a method for treating or lessening the severity of a disease, condition, or disorder with compounds that inhibit enzymatic activity by binding to the ATR kinase.

Another aspect provides a method for treating or lessening the severity of a kinase disease, condition, or disorder by inhibiting enzymatic activity of ATR kinase with an ATR kinase inhibitor.

One aspect of the invention relates to a method of inhibiting ATR kinase activity in a patient, which method comprises administering to the patient a compound described herein, or a composition comprising said compound. In some embodiments, said method is used to treat or prevent a condition selected from proliferative and hyperproliferative diseases, such as cancer.

Another aspect of this invention provides a method for treating, preventing, or lessening the severity of proliferative or hyperproliferative diseases comprising administering an effective amount of a compound, or a pharmaceutically acceptable composition comprising a compound, to a subject in need thereof. In some embodiments, said subject is a patient. The term "patient", as used herein, means an animal, preferably a human.

In some embodiments, said method is used to treat or prevent cancer. In some embodiments, said method is used to treat or prevent a type of cancer with solid tumors. In yet another embodiment, said cancer is selected from the following cancers: Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, multiple endocrine neoplasia type 2A, multiple endocrine neoplasia type 2B, familial medullary thyroid cancer, pheochromocytoma, paraganglioma; and Adrenal glands: neuroblastoma.

In some embodiments, the cancer is selected from the cancers described herein. In some embodiments, said cancer is lung cancer, head and neck cancer, pancreatic cancer, gastric cancer, or brain cancer. In other embodiments, the cancer is selected from a cancer of the lung or the pancreas.

In yet other embodiments, the cancer is selected from non-small cell lung cancer, small cell lung cancer, pancreatic cancer, biliary tract cancer, head and neck cancer, bladder cancer, colorectal cancer, glioblastoma, esophageal cancer, breast cancer, hepatocellular carcinoma, or ovarian cancer.

In certain embodiments, an "effective amount" of the compound or pharmaceutically acceptable composition is that amount effective in order to treat said disease. The compounds and compositions, according to the method of the present invention, may be administered using any amount and any route of administration effective for treating or lessening the severity of said disease.

One aspect provides a method for inhibiting ATR in a patient comprising administering a compound described herein as described herein. Another embodiment provides a method of treating cancer comprising administering to a patient a compound described herein, wherein the variables are as defined herein.

Some embodiments comprising administering to said patient an additional therapeutic agent selected from a DNA-damaging agent; wherein said additional therapeutic agent is appropriate for the disease being treated; and said additional therapeutic agent is administered together with said compound as a single dosage form or separately from said compound as part of a multiple dosage form.

In some embodiments, said DNA-damaging agent is selected from ionizing radiation, radiomimetic neocarzinostatin, a platinating agent, a Topo I inhibitor, a Topo II inhibitor, an antimetabolite, an alkylating agent, an alkyl sulphonates, an antimetabolite, or an antibiotic. In other embodiments, said DNA-damaging agent is selected from ionizing radiation, a platinating agent, a Topo I inhibitor, a Topo II inhibitor, or an antibiotic.

Examples of Platinating agents include Cisplatin, Oxaliplatin, Carboplatin, Nedaplatin, Satraplatin and other derivatives. Other platinating agents include Lobaplatin, and Triplatin. Other platinating agents include Tetranitrate, Picoplatin, Satraplatin, ProLindac and Aroplatin.

Examples of Topo I inhibitor include Camptothecin, Topotecan, irinotecan/SN38, rubitecan and other derivatives. Other Topo I inhibitors include Belotecan.

Examples of Topo II inhibitors include Etoposide, Daunorubicin, Doxorubicin, Aclarubicin, Epirubicin, Idarubicin, Amrubicin, Pirarubicin, Valrubicin, Zorubicin and Teniposide.

Examples of Antimetabolites include members of the Folic family, Purine family (purine antagonists), or Pyrimidine family (pyrimidine antagonists). Examples of the Folic family include methotrexate, pemetrexed and relatives; examples of the Purine family include Thioguanine, Fludarabine, Cladribine, 6-Mercaptopurine, and relatives; examples of the Pyrimidine family include Cytarabine, gemcitabine, 5-Fluorouracil (5FU) and relatives.

Some other specific examples of antimetabolites include Aminopterin, Methotrexate, Pemetrexed, Raltitrexed, Pentostatin, Cladribine, Clofarabine, Fludarabine, Thioguanine, Mercaptopurine, Fluorouracil, Capecitabine, Tegafur, Carmofur, Floxuridine, Cytarabine, Gemcitabine, Azacitidine and Hydroxyurea.

Examples of alkylating agents include Nitrogen mustards, Triazenes, alkyl sulphonates, Procarbazine and Aziridines. Examples of Nitrogen mustards include Cyclophosphamide, Melphalan, Chlorambucil and relatives; examples of nitrosoureas include Carmustine; examples of triazenes include Dacarbazine and temozolomide; examples of alkyl sulphonates include Busulfan.

Other specific examples of alkylating agents include Mechlorethamine, Cyclophosphamide, Ifosfamide, Trofosfamide, Chlorambucil, Melphalan, Prednimustine, Bendamustine, Uramustine, Estramustine, Carmustine, Lomustine, Semustine, Fotemustine, Nimustine, Ranimustine, Streptozocin, Busulfan, Mannosulfan, Treosulfan, Carboquone, ThioTEPA, Triaziquone, Triethylenemelamine, Procarbazine, Dacarbazine, Temozolomide, Altretamine, Mitobronitol, Actinomycin, Bleomycin, Mitomycin and Plicamycin.

Examples of antibiotics include Mitomycin, Hydroxyurea; Anthracyclines, Anthracenediones, Streptomyces family. Examples of Anthracyclines include doxorubicin, daunorubicin, epirubicin and other derivatives; examples of Anthracenediones include Mitoxantrone and relatives; examples of Streptomyces family inclue Bleomycin, Mitomycin C, and actinomycin.

In certain embodiments, said platinating agent is Cisplatin or Oxaliplatin; said Topo I inhibitor is Camptothecin; said Topo II inhibitor is Etoposide; and said antibiotic is Mitomycin. In other embodiments, said platinating agent is selected from Cisplatin, Oxaliplatin, Carboplatin, Nedaplatin, or Satraplatin; said Topo I inhibitor is selected from Camptothecin, Topotecan, irinotecan/SN38, rubitecan; said Topo II inhibitor is selected from Etoposide; said antimetabolite is selected from a member of the Folic Family, the Purine Family, or the Pyrimidine Family; said alkylating agent is selected from nitrogen mustards, nitrosoureas, triazenes, alkyl sulfonates, Procarbazine, or aziridines; and said antibiotic is selected from Hydroxyurea, Anthracyclines, Anthracenediones, or Streptomyces family.

In some embodiments, the additional therapeutic agent is ionizing radiation. In other embodiments, the additional therapeutic agent is Cisplatin or Carboplatin. In yet other embodiments, the additional therapeutic agent is Etoposide. In yet other embodiments, the additional therapeutic agent is Temozolomide.

In certain embodiments, the additional therapeutic agent is selected from one or more of the following: Cisplatin, Carboplatin, gemcitabine, Etoposide, Temozolomide, or ionizing radiation.

Another embodiment provides methods for treating pancreatic cancer by administering a compound described herein in combination with another known pancreatic cancer treatment. One aspect of the invention includes administering a compound described herein in combination with gemcitabine. In some embodiments, the pancreatic cancer comprises one of the following cell lines: PSN-1, MiaPaCa-2 or Panc-1.

According to another aspect, the cancer comprises one of the following primary tumor lines: Panc-M or MRC5.

Another aspect of the invention includes administering a compound described herein in combination with radiation therapy. Yet another aspect provides a method of abolishing radiation-induced G2/M checkpoint by administering a compound described herein in combination with radiation treatment.

Another aspect provides a method of treating pancreatic cancer by administering to pancreatic cancer cells a compound described herein in combination with one or more cancer therapies. In some embodiments, the compound is combined with chemoradiation, chemotherapy, and/or radiation therapy. As would be understood by one of skill in the art, chemoradiation refers to a treatment regime that includes both chemotherapy (such as gemcitabine) and radiation. In some embodiments, the chemotherapy is gemcitabine.

Yet another aspect provides a method of increasing the sensitivity of pancreatic cancer cells to a cancer therapy selected from gemcitabine or radiation therapy by administering a compound described herein in combination with the cancer therapy.

In some embodiments, the cancer therapy is gemcitabine. In other embodiments, the cancer therapy is radiation therapy. In yet another embodiment the cancer therapy is chemoradiation.

Another aspect provides a method of inhibiting phosphorylation of Chk1 (Ser 345) in a pancreatic cancer cell comprising administering a compound described herein after treatment with gemcitabine (100 nM) and/or radiation (6 Gy) to a pancreatic cancer cell.

Another aspect provides method of radiosensitizing hypoxic PSN-1, MiaPaCa-2 or PancM tumor cells by administering a compound described herein to the tumor cell in combination with radiation therapy.

Yet another aspect provides a method of sensitizing hypoxic PSN-1, MiaPaCa-2 or PancM tumor cells by administering a compound described herein to the tumor cell in combination with gemcitabine.

Another aspect provides a method of sensitizing PSN-1 and MiaPaCa-2 tumor cells to chemoradiation by administering a compound described herein to the tumor cells in combination with chemoradiation.

Another aspect provides a method of disrupting damage-induced cell cycle checkpoints by administering a compound described herein in combination with radiation therapy to a pancreatic cancer cell.

Another aspect provides a method of inhibiting repair of DNA damage by homologous recombination in a pancreatic cancer cell by administering a compound described herein in combination with one or more of the following treatments: chemoradiation, chemotherapy, and radiation therapy.

In some embodiments, the chemotherapy is gemcitabine.

Another aspect provides a method of inhibiting repair of DNA damage by homologous recombination in a pancreatic cancer cell by administering a compound described herein in combination with gemcitabine and radiation therapy.

In some embodiments, the pancreatic cancer cells are derived from a pancreatic cell line selected from PSN-1, MiaPaCa-2 or Panc-1.

In other embodiments, the pancreatic cancer cells are in a cancer patient.

Another aspect of the invention provides a method of treating non-small cell lung cancer comprising administering to a patient a compound described herein in combination with one or more of the following additional therapeutic agents: Cisplatin or Carboplatin, Etoposide, and ionizing radiation. Some embodiments comprise administering to a patient a compound described herein in combination with Cisplatin or Carboplatin, Etoposide, and ionizing radiation. In some embodiments the combination is Cisplatin, Etoposide, and ionizing radiation. In other embodiments the combination is Carboplatin, Etoposide, and ionizing radiation.

Another embodiment provides a method of promoting cell death in cancer cells comprising administering to a patient a compound described herein, or a composition comprising said compound.

Yet another embodiment provides a method of preventing cell repair of DNA damage in cancer cells comprising administering to a patient a compound described herein, or a composition comprising said compound. Yet another embodiment provides a method of preventing cell repair caused by of DNA damage in cancer cells comprising administering to a patient a compound described herein, or composition comprising said compound.

Another embodiment provides a method of sensitizing cells to DNA damaging agents comprising administering to a patient a compound described herein, or a composition comprising said compound.

In some embodiments, the method is used on a cancer cell having defects in the ATM signaling cascade. In some embodiments, said defect is altered expression or activity of one or more of the following: ATM, p53, CHK2, MRE11, RAD50, NBS1, 53BP1, MDC1, H2AX, MCPH1/BRIT1, CTIP, or SMC1. In other embodiments, said defect is altered expression or activity of one or more of the following: ATM, p53, CHK2, MRE11, RAD50, NBS1, 53BP1, MDC1 or H2AX. According to another embodiment, the method is used on a cancer, cancer cell, or cell expressing DNA damaging oncogenes.

In another embodiment, the cell is a cancer cell expressing DNA damaging oncogenes. In some embodiments, said cancer cell has altered expression or activity of one or more of the following: K-Ras, N-Ras, H-Ras, Raf, Myc, Mos, E2F, Cdc25A, CDC4, CDK2, Cyclin E, Cyclin A and Rb.

According to another embodiment, the method is used on a cancer, cancer cell, or cell has a defect in a protein involved in base excision repair ("base excision repair protein"). There are many methods known in the art for determining whether a tumor has a defect in base excision repair. For example, sequencing of either the genomic DNA or mRNA products of each base excision repair gene (e.g., UNG, PARP1, or LIG1) can be performed on a sample of the tumor to establish whether mutations expected to modulate the function or expression of the gene product are present (Wang et al., Cancer Research 52:4824 (1992)). In addition to the mutational inactivation, tumor cells can modulate a DNA repair gene by hypermethylating its promoter region, leading to reduced gene expression. This is most commonly assessed using methylation-specific polymerase chain reaction (PCR) to quantify methylation levels on the promoters of base excision repair genes of interest. Analysis of base excision repair gene promoter methylation is available commercially (http://www.sabiosciences.com/dna_methylation_product/HTML/MEAH-421A.html).

Finally, the expression levels of base excision repair genes can be assessed by directly quantifying levels of the mRNA and protein products of each gene using standard techniques such as quantitative reverse transcriptase-coupled polymerase chain reaction (RT-PCR) and immunohohistochemistry (IHC), respectively (Shinmura et al., Carcinogenesis 25: 2311 (2004); Shinmura et al., Journal of Pathology 225:414 (2011)).

In some embodiments, the base excision repair protein is UNG, SMUG1, MBD4, TDG, OGG1, MYH, NTH1, MPG, NEIL1, NEIL2, NEIL3 (DNA glycosylases); APE1, APEX2 (AP endonucleases); LIG1, LIG3 (DNA ligases I and III); XRCC1 (LIG3 accessory); PNK, PNKP (polynucleotide kinase and phosphatase); PARP1, PARP2 (Poly(ADP-Ribose) Polymerases); PolB, PolG (polymerases); FEN1 (endonuclease) or Aprataxin.

In some embodiments, the base excision repair protein is PARP1, PARP2, or PolB. In other embodiments, the base excision repair protein is PARP1 or PARP2.

The methods described above (gene sequence, promoter methylation and mRNA expression) may also be used to characterize the status (e.g., expression or mutation) of other genes or proteins of interesting, such DNA-damaging oncogenes expressed by a tumor or defects in the ATM signaling cascade of a cell.

Yet another embodiment provides use of a compound described herein as a radio-sensitizer or a chemo-sensitizer.

Yet other embodiment provides use of a compound described herein as a single agent (monotherapy) for treating cancer. In some embodiments, the compounds described herein are used for treating patients having cancer with a DNA-damage response (DDR) defect. In other embodiments, said defect is a mutation or loss of ATM, p53, CHK2, MRE11, RAD50, NBS1, 53BP1, MDC1, or H2AX.

Compounds and Compositions for Use

One embodiment provides a compound or composition as described herein for use as a radio-sensitizer or a chemo-sensitizer. Another embodiment provides a compound or composition as described herein for use as a single agent (monotherapy) for treating cancer.

Another embodiment provides a compound or composition as described herein for treating patients having cancer with a DNA-damage response (DDR) defect. In some embodiments, said defect is a mutation or loss of ATM, p53, CHK2, MRE11, RAD50, NBS1, 53BP1, MDC1, or H2AX. In other embodiments, said defect is a mutation or loss of ATM, p53, CHK2, MRE11, RAD50, NBS1, 53BP1, MDC1, H2AX, MCPH1/BRIT1, CTIP, or SMC1.

Another embodiment provides compounds or compositions described herein for treating cancer. In some embodiments, the compound or composition is further combined with an additional therapeutic agent described herein. In some embodiments, the compound or composition is further combined with a DNA damaging agent described herein.

In some embodiments, the cancer has a defect in a pathway described herein.

Manufacture of Medicaments

One embodiment provides the use of a compound or composition described herein for the manufacture of a medicament for use as a radio-sensitizer or a chemo-sensitizer. Another embodiment provides the use of a compound or composition described herein for the manufacture of a medicament for the manufacture of a medicament for use as a single agent (monotherapy) for treating cancer.

Yet another embodiment provides the use of a compound or composition described herein for the manufacture of a medicament for the manufacture of a medicament for treating patients having cancer with a DNA-damage response (DDR) defect. In some embodiments, said defect is a mutation or loss of ATM, p53, CHK2, MRE11, RAD50, NBS1, 53BP1, MDC1, or H2AX. In other embodiments, said defect is a mutation or loss of ATM, p53, CHK2, MRE11, RAD50, NBS1, 53BP1, MDC1, H2AX, MCPH1/BRIT1, CTIP, or SMC1.

Another embodiment provides the use of a compound or composition described herein for the manufacture of a medicament for treating cancer. In some embodiments, the compound or composition is combined with an additional therapeutic agent, such as a DNA damaging agent, described herein. In another embodiment, the cancer has a defect in a pathway described herein.

SCHEMES AND EXAMPLES

The compounds of the disclosure may be prepared in light of the specification using steps generally known to those of ordinary skill in the art. Those compounds may be analyzed by known methods, including but not limited to LCMS (liquid chromatography mass spectrometry) and NMR (nuclear magnetic resonance). The following generic schemes and examples illustrate how to prepare the compounds of the present disclosure. The examples are for the purpose of illustration only and are not to be construed as limiting the scope of the invention in any way. $^1$H-NMR spectra were recorded at 400 MHz using a Bruker DPX 400 instrument. Mass spec. samples were analyzed on a MicroMass Quattro Micro mass spectrometer operated in single MS mode with electrospray ionization.

Scheme A: General Synthesis of Compound I-1

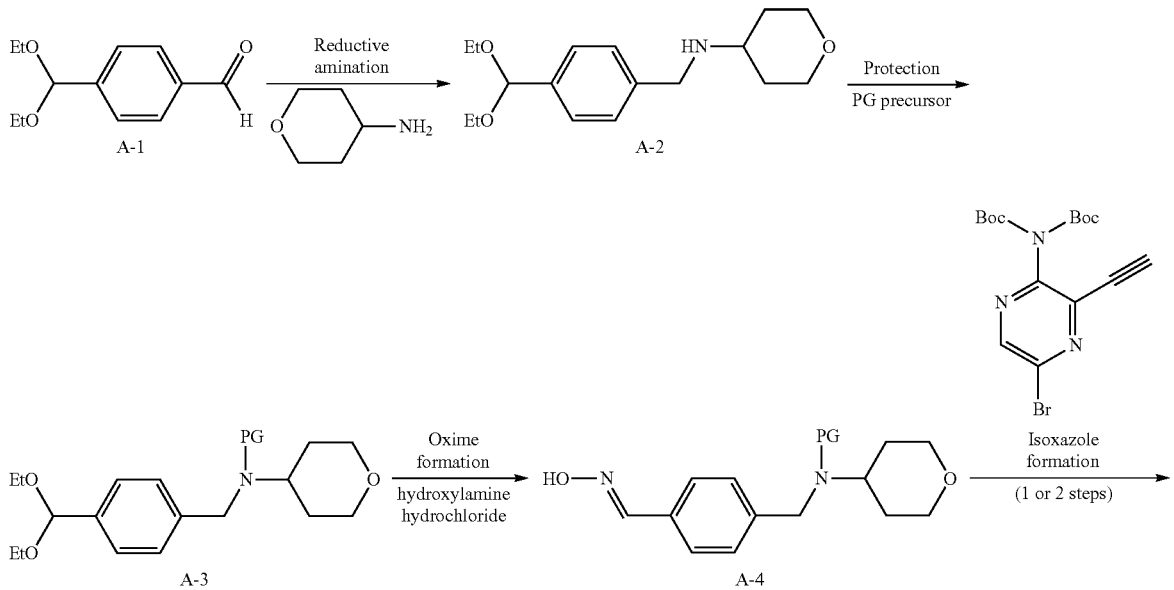

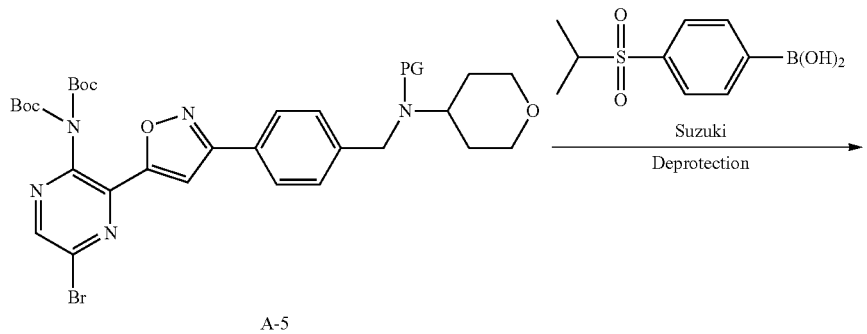

A-5

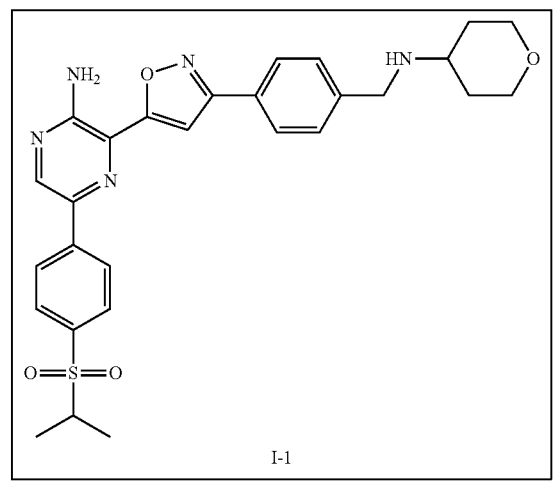

I-1

The compound of formula I-1 can be made according to the steps outlined in Scheme A. Reductive amination between compound A-1 and tetrahydro-2H-pyran-4-amine lead to compound A-2. Suitable reductive amination conditions include, for example, combining compound A-1 with tetrahydro-2H-pyran-4-amine in methanol to form an intermediate which reduced with NaBH$_4$ to form compound A-2. Compound A-2 can then be protected with nitrogen protecting groups known to one of skill in the art. For example, compound B-2 can be combined with (Boc)$_2$O and Et$_3$N in DCM to form compound A-3 (wherein PG=Boc).

Compound A-3 can be combined with hydroxylamine hydrochloride under suitable oxime formation conditions to form compound A-4. Suitable oxime formation conditions include either a one-step procedure or a two-step procedure. The one-step procedure comprises stirring 1 equivalent of compound A-3 with a 1.1 equivalents of NH$_2$OH.HCl in a 10:1 v/v mixture of THF/water. The two step procedure comprises first deprotecting the ketal group of compound 3 into an aldehyde under suitable deprotection conditions, and then forming an oxime under suitable two-step oxime formation conditions to form compound A-4.

Compound A-4 can be combined with the Boc-protected aminopyrazine shown in Scheme A under suitable isoxazole formation conditions to form compound A-5. Compound A-4 is transformed and engaged in a [3+2] cycloaddition to form the isoxazole A-5. This transformation can be conducted in one pot but requires two distinct steps. The first step is an oxidation of the oxime functional group into a nitrone, or a similar intermediate with the same degree of oxidation, for example a chlorooxime. This reactive species then reacts with an alkyne in a [3+2] cycloaddition to form the isoxazole adduct.

Finally, compound A-5 undergoes a metal-assisted coupling reaction followed by deprotection to form a compound of formula I-1. For example, compound A-5 can be combined with a boronic acid under Suzuki cross-coupling conditions followed by acid-mediated deprotection to form the compound of formula I-1.

Scheme AA: Example Synthesis of Compound I-1

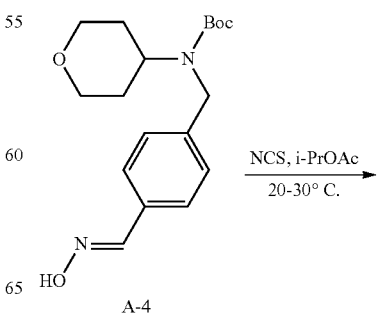

A-4

-continued

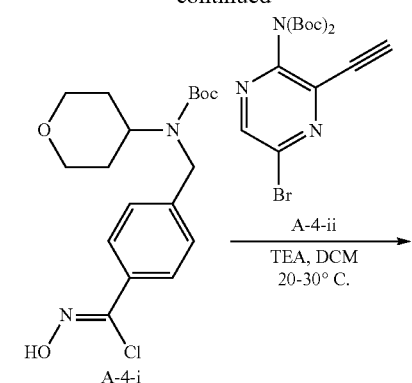

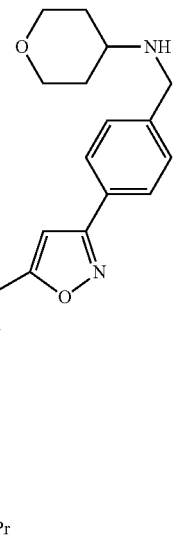

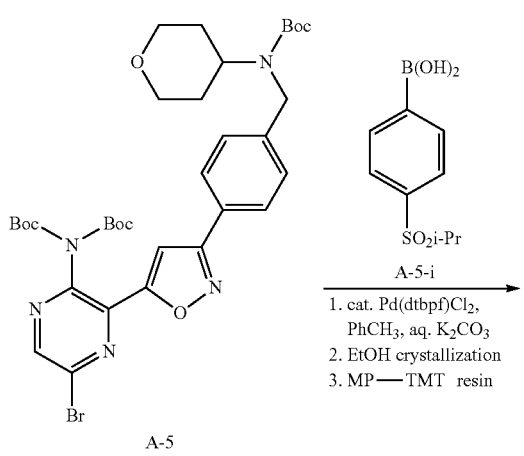

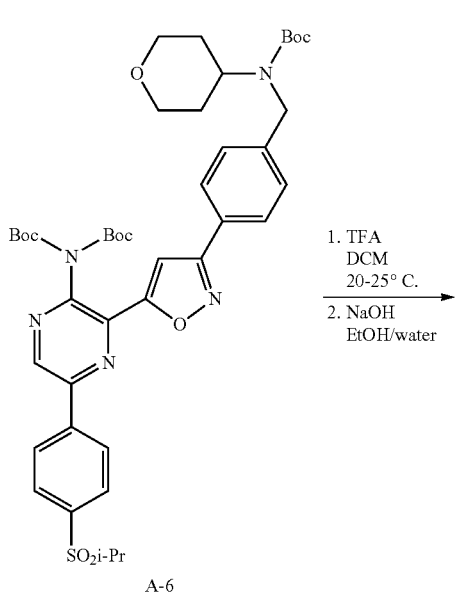

Example 1

Synthesis of 5-(4-(Isopropylsulfonyl)phenyl)-3-(3-(4-(tetrahydropyran-4-ylamino)methyl)phenyl) isoxazol-5-yl)pyrazin-2-amine (Compound I-1)

Step 1: Preparation of N-(4-(diethoxymethyl)benzyl) tetrahydro-2H-pyran-4-amine (A-2)

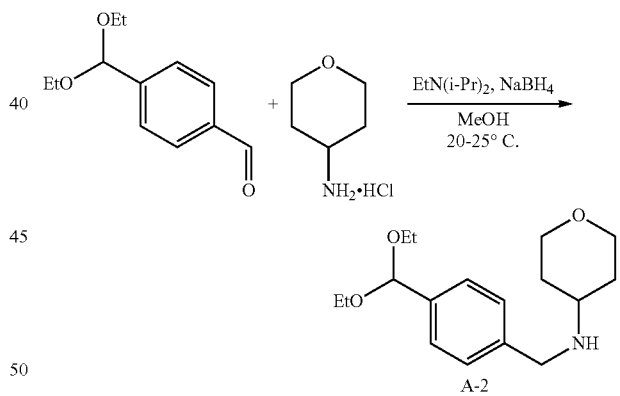

A solution of tetrahydro-2H-pyran-4-amine hydrochloride (1.13 kg, 8.21 mol) in MeOH (14.3 L) is stirred at about 20° C. then Et$_3$N (1.06 kg, 1.43 L, 8.21 mol) is added. The mixture is stirred for at least 5 min then terephthalaldehyde diethyl acetal (1.43 kg, 6.84 mol) is added while maintaining the reaction temperature between 20-25° C. The mixture is stirred for at least 45 min to form the imine. NaBH$_4$ caplets (414 g, 11.0 mol) are added while maintaining the reaction temperature below about 25° C. The mixture is stirred for 1 h after the addition is completed. The reaction mixture is quenched by adding 1 M NaOH (13.7 L) then extracted with MTBE. The organic solution was washed with brine (7.13 L) then dried (Na$_2$SO$_4$) and concentrated to afford Compound A-2 (2197 g; 109% yield, 94.4 area % purity by HPLC) as a hazy oil. $^1$H NMR (400 MHz, CDCl$_3$) δ 7.43 (d, J=8.1 Hz, 2H), 7.31 (d, J=8.1 Hz, 2H), 5.49 (s, 1H), 4.66 (br s, 1H), 4.03-3.91 (m, 2H), 3.82 (s, 2H), 3.69-3.47 (m, 4H), 3.38 (td, J=11.6, 2.1 Hz, 2H), 2.78-2.65 (m, 1H), 1.90-1.81 (m, 2H), 1.53-1.37 (m, 2H), 1.23 (t, J=7.1 Hz, 6H).

Step 2: Preparation of tert-butyl 4-(diethoxymethyl)benzyl(tetrahydro-2H-pyran-4-yl)carbamate (A-3)

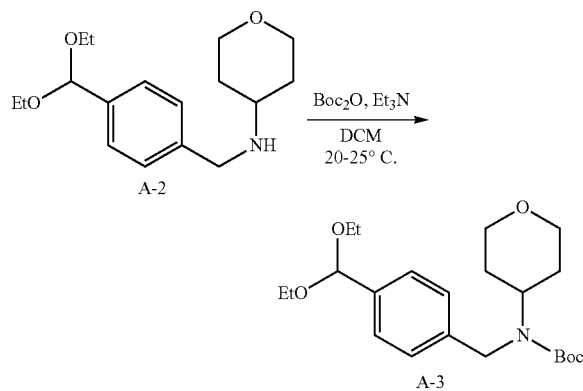

A mixture of N-(4-(diethoxymethyl)benzyl)tetrahydro-2H-pyran-4-amine (A-2) (2195 g, 7.48 mol) in CH$_2$Cl$_2$ (22.0 L) is stirred at 25° C. then di-t-butyl dicarbonate (1.71 kg, 7.86 mol) is added. Et$_3$N (795 g, 1.10 L) is then added while maintaining the reaction temperature between 20-25° C. The reaction mixture is stirred at about 25° C. for 12-20 h. After the reaction is completed, the mixture is cooled to about 20° C. and quenched with 0.5 M aqueous citric acid (7.48 L, 3.74 mol) while maintaining the reaction temperature between 20-25° C. The organic phase is collected, washed with sat. NaHCO$_3$ (6.51 L, 7.48 mol), washed with brine (6.59 L), and dried (Na$_2$SO$_4$) then concentrated to afford tert-butyl 4-(diethoxymethyl)benzyl(tetrahydro-2H-pyran-4-yl)carbamate (A-3) (2801 g; 95% yield, 98.8 area % purity by HPLC) as a thick, amber oil. $^1$H NMR (400 MHz, CDCl$_3$) δ 7.40 (d, J=8.1 Hz, 2H), 7.21 (d, J=7.9 Hz, 2H), 5.49 (s, 1H), 4.39 (br s, 3H), 3.93 (br dd, J=10.8, 3.8 Hz, 2H), 3.67-3.47 (m, 4H), 3.40 (br m, 2H), 1.68-1.59 (m, 4H), 1.39 (br s, 9H), 1.23 (t, J=7.1 Hz, 6H).

Step 3: Preparation of tert-butyl 4-((hydroxyimino)methyl)benzyl(tetrahydro-2H-pyran-4-yl)carbamate (A-4)

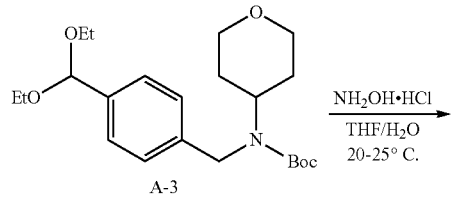

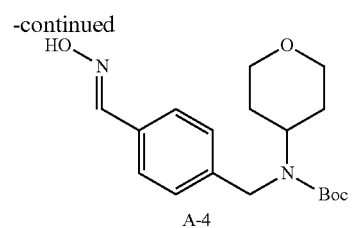

A solution of tert-butyl 4-(diethoxymethyl)benzyl(tetrahydro-2H-pyran-4-yl)carbamate (A-3) (2.80 kg, 7.12 mol) in THF (28.0 L) and water (2.80 L) is stirred at about 20° C. Hydroxylamine hydrochloride (593 g, 8.54 mol) is added while maintaining the reaction temperature between 20-25° C. The reaction mixture is stirred at about 20° C. for 16-20 h then diluted with CH$_2$Cl$_2$ (8.4 L) and 50% brine (11.2 L) and stirred for at least 5 min. The phases are separated then the organic phase is washed with 50% brine (2×2.8 L), dried (Na$_2$SO$_4$) and concentrated. The concentrate is diluted with MeOH (1.4 L) and re-concentrated. The concentrate is diluted with MeOH (14.0 L) and transferred to a reaction vessel. The solution is warmed to about 25° C. then water (14.0 L) is added over about 1-1.5 h; after about 10 L of water is added, the mixture is seeded and a hazy suspension is observed. Additional water (8.4 L) is added over 1.5 h to further precipitate the product. After aging, the solid is collected by filtration. The filter-cake is washed with heptane (5.6 L) and dried to afford tert-butyl 4-((hydroxyimino)methyl)benzyl(tetrahydro-2H-pyran-4-yl)carbamate (A-4) (1678 g; 71% 71% yield, 91.5 area % purity by HPLC) as an off-white powder. $^1$H NMR (400 MHz, CDCl$_3$) δ 8.12 (s, 1H), 7.51 (d, J=8.2 Hz, 2H), 7.24 (d, J=7.9 Hz, 2H), 4.40 (br s, 3H), 3.96 (dd, J=10.4, 3.6 Hz, 2H), 3.41 (br m, 2H), 1.69-1.61 (m, 4H), 1.39 (br s, 9H).

Step 4: Preparation of (tert-butyl 4-(chloro(hydroxyimino)methyl)benzyl(tetrahydro-2H-pyran-4-yl)carbamate (A-4-i)

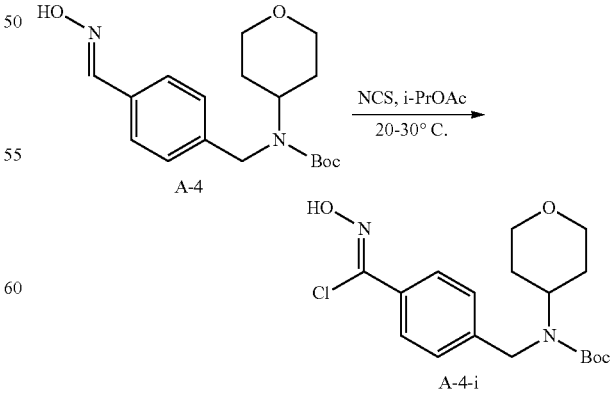

A suspension of (E)-tert-butyl 4-((hydroxyimino)methyl)benzyl(tetrahydro-2H-pyran-4-yl)carbamate (A-4) (1662 g, 4.97 mol) in i-PrOAc (16.6 L) is stirred at 20° C. in a reactor. N-chlorosuccinimide (730 g, 5.47 mol) is added maintaining about 20° C. The suspension is stirred at about 20° C. to complete the reaction. The suspension is diluted with water (8.3 L) and stirred to dissolve the solid. The phases are separated and the organic phase is washed with water (8.3 L). The organic phase is concentrated then diluted with i-PrOAc (831 mL). Heptane (13.3 L; 8 V) is slowly added to induce crystallization. The thick suspension is then stirred for 1 h. The solid is collected by filtration; the filter-cake is washed with heptane (2×1.6 L; 2×1 V) and dried to afford (Z)-tert-butyl 4-(chloro(hydroxyimino)methyl)benzyl(tetrahydro-2H-pyran-4-yl)carbamate (A-4-i) (1628 g 89%, 98.0 area % purity by HPLC) as a white powder.

Step 5: Preparation of tert-butyl(5-bromo-3-(3-(4-(((tert-butoxycarbonyl)(tetrahydro-2H-pyran-4-yl)amino)methyl)phenyl)isoxazol-5-yl)pyrazin-2-yl)(tert-butoxycarbonyl)carbamate (A-5)

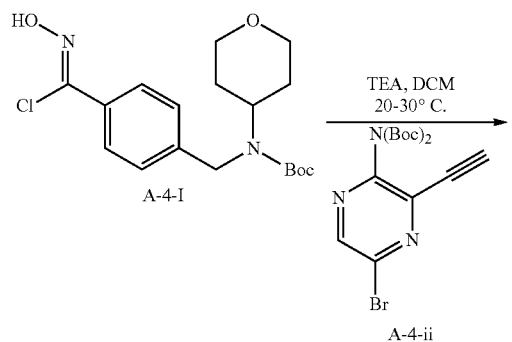

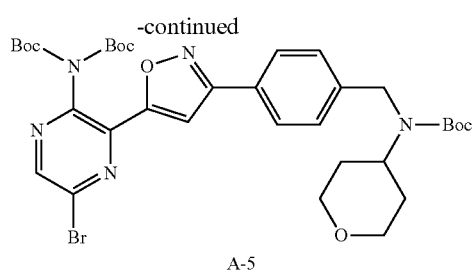

A solution of tert-butyl 4-(chloro(hydroxyimino)methyl)benzyl(tetrahydro-2H-pyran-4-yl)carbamate (A-4-i) (1.60 kg, 4.34 mol) and tert-butyl N-(5-bromo-3-ethynylpyrazin-2-yl)-N-tert-butoxycarbonylcarbamate (Compound A-4-ii) (1.73 kg, 4.34 mol) in $CH_2Cl_2$ (12.8 L) is stirred at 20° C. $Et_3N$ (483 g, 665 mL; 4.77 mol) is added and the reaction temperature maintained below 30° C. The suspension stirred at 20° C. to complete the reaction then diluted with water (8.0 L) and agitated. The phases are separated and the organic phase is washed with water (8.0 L) and then concentrated. i-PrOAc (1.6 L) is added and the mixture and heated at 50° C. Heptane (4.0 L) was slowly added then the suspension is allowed to cool to ambient temperature and stirred overnight. Additional heptane (7.2 L) is added to the suspension and it is stirred for 1 h. The solid is collected by filtration. The filter-cake is washed with heptane (2×1.6 L) and dried to afford tert-butyl(5-bromo-3-(3-(4-(((tert-butoxycarbonyl)(tetrahydro-2H-pyran-4-yl)amino)methyl)phenyl)isoxazol-5-yl)pyrazin-2-yl)(tert-butoxycarbonyl)carbamate (A-5) (2.478 kg; 78%, 97.8 area % purity by HPLC) as a fine, tan powder.
$^1H$ NMR (400 MHz, $CDCl_3$) δ 8.60 (s, 1H), 7.78 (d, J=8.3 Hz, 2H), 7.31 (m, 3H), 4.42 (br m, 3H), 4.03-3.82 (m, 2H), 3.38 (br s, 2H), 1.60 (m, 4H), 1.36 (s, 27H).

Step 6: Preparation of tert-butyl tert-butoxycarbonyl (3-(3-(4-(((tert-butoxycarbonyl)(tetrahydro-2H-pyran-4-yl)amino)methyl)phenyl)isoxazol-5-yl)-5-(4-(isopropylsulfonyl)phenyl)pyrazin-2-yl)carbamate

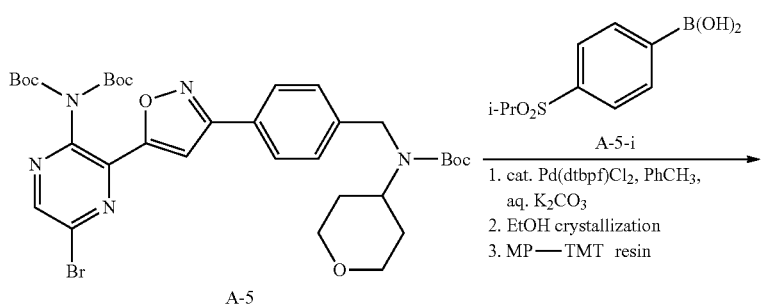

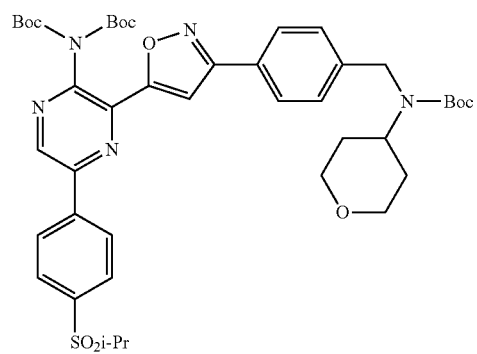

A mixture of tert-butyl(5-bromo-3-(3-(4-(((tert-butoxycarbonyl)(tetrahydro-2H-pyran-4-yl)amino)methyl)phenyl)isoxazol-5-yl)pyrazin-2-yl)(tert-butoxycarbonyl)carbamate (A-5) (425 g, 582 mmol), K₂CO₃ (161 g, 1.16 mol; 2.0 equiv.), and (4-(isopropylsulfonyl)phenyl)boronic acid (133 g, 582 mmol) in toluene (2.98 L) and water (850 mL) is stirred and degassed with N₂ at ambient temperature. The catalyst [1,1'-bis(di-tert-butylphosphino)ferrocene]dichloropalladium(II), (Pd(dtbpf)Cl₂; 1.90 g, 2.91 mmol) is added and the mixture is degassed for an additional 10 min. The mixture is heated at 70° C. until the reaction is complete. The mixture is cooled to 50° C., diluted with water (850 mL) and filtered through a bed of Celite. The phases are separated. The organic phase is concentrated then the residue is diluted with EtOH (1.70 L) and re-concentrated. With mixing at 40° C., the concentrate is diluted with EtOH (1.70 L) to induce crystallization. The suspension is cooled to 20° C. and stirred for 4 h. The solid is collected by filtration. The filter-cake is washed with EtOH (2×425 mL) and air-dried to afford tert-butyl tert-butoxycarbonyl(3-(3-(4-(((tert-butoxycarbonyl)(tetrahydro-2H-pyran-4-yl)amino)methyl)phenyl)isoxazol-5-yl)-5-(4-(isopropylsulfonyl)phenyl)pyrazin-2-yl)carbamate (A-6) as a beige powder. The solid is dissolved in THF (2.13 L) and slurried with Biotage MP-TMT resin (48 g) at ambient temperature. The resin is removed by filtration and the filtrate concentrated to remove most of the THF. The concentrate is diluted with EtOH (970 mL) and re-concentrated to about half the original volume. The concentrate is diluted again with EtOH (970 mL) and mixed for 1 h at 40° C. The suspension is cooled to ambient temperature and the solid is collected by filtration then dried to afford tert-butyl tert-butoxycarbonyl (3-(3-(4-(((tert-butoxycarbonyl)(tetrahydro-2H-pyran-4-yl)amino)methyl)phenyl)isoxazol-5-yl)-5-(4-(isopropylsulfonyl)phenyl)pyrazin-2-yl)carbamate (A-6) (416 g 86% yield, 99.3 area % purity by HPLC) as a white powder. ¹H NMR (400 MHz, CDCl₃) δ 9.04 (s, 1H), 8.38-8.28 (m, 2H), 8.10-8.01 (m, 2H), 7.82 (d, J=8.2 Hz, 2H), 7.34 (m, 3H), 4.44 (br s, 2H), 3.94 (dd, J=10.5, 3.5 Hz, 2H), 3.40 (br s, 2H), 3.25 (hept, J=6.8 Hz, 1H), 1.65 (m, 4H), 1.38 (br s, 27H), 1.33 (d, J=6.9 Hz, 6H).

Step 7: Preparation of 5-(4-(isopropylsulfonyl)phenyl)-3-(3-(4-(((tetrahydro-2H-pyran-4-yl)amino)methyl)phenyl)isoxazol-5-yl)pyrazin-2-amine (1-1) freebase form

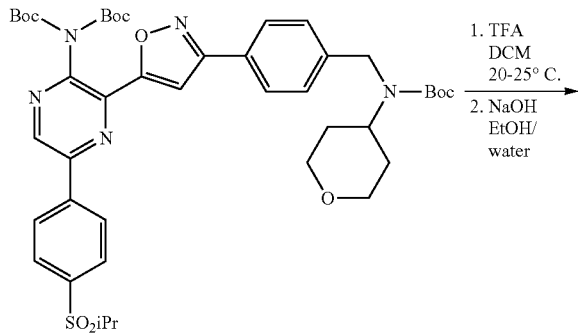

A-6

1. TFA DCM 20-25° C.
2. NaOH EtOH/water

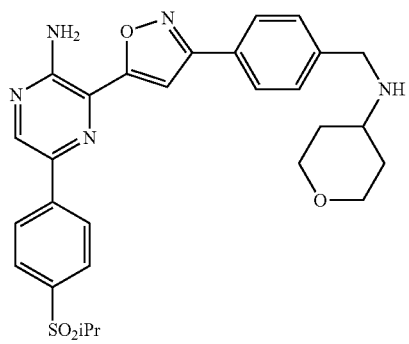

I-1

A suspension of tert-butyl tert-butoxycarbonyl(3-(3-(4-(((tert-butoxycarbonyl)(tetrahydro-2H-pyran-4-yl)amino)methyl)phenyl)isoxazol-5-yl)-5-(4-(isopropylsulfonyl)phenyl)pyrazin-2-yl)carbamate (A-6) (410 g; 492 mmol) in CH₂Cl₂ (410 mL) is stirred at ambient temperature in a flask. TFA (841 g, 568 mL; 7.4 mol) is added while maintaining the reaction temperature between 20-25° C. The solution is stirred at ambient temperature for about 3 h when analysis shows reaction completion. The solution is cooled to about 5-10° C. and diluted with EtOH (3.3 L) while maintaining the temperature below 20° C. A 5.0 M aqueous solution of NaOH (1.77 L; 8.85 mol) is added while allowing the reaction temperature to rise from about 14° C. to about 42° C. The suspension is heated at 70-75° C. for 6 h while removing distillate. The suspension is allowed to cool to ambient temperature. The solid is collected by filtration and the filter-cake is washed with water (4×1.64 L). The filter-cake is washed with EtOH (2×820 mL) and dried to afford 5-(4-(isopropylsulfonyl)phenyl)-3-(3-(4-(((tetrahydro-2H-pyran-4-yl)amino)methyl)phenyl) isoxazol-5-yl)pyrazin-2-amine (Compound I-1) (257 g; 98% yield, 99.5 area % purity by HPLC) as a yellow powder. ¹H NMR (400 MHz, DMSO) δ 8.94 (s, 1H), 8.44-8.33 (m, 2H), 7.94 (t, J=8.2 Hz, 4H), 7.76 (s, 1H), 7.53 (d, J=8.2 Hz, 2H), 7.20 (s, 2H), 3.83 (m, 1H), 3.80 (s, 3H), 3.46 (hept, J=6.8 Hz, 1H), 3.25 (td, J=11.4, 2.1 Hz, 2H), 2.66-2.54 (m, 1H), 1.79 (br dd, 2H), 1.36-1.22 (m, 2H), 1.19 (d, J=6.8 Hz, 6H). ¹³C NMR (101 MHz, DMSO) δ 167.57, 151.76, 141.07, 137.58, 135.75, 129.16, 128.53, 126.57, 126.41, 125.69, 124.52, 102.13, 65.83, 54.22, 52.60, 49.19, 33.18, 15.20.

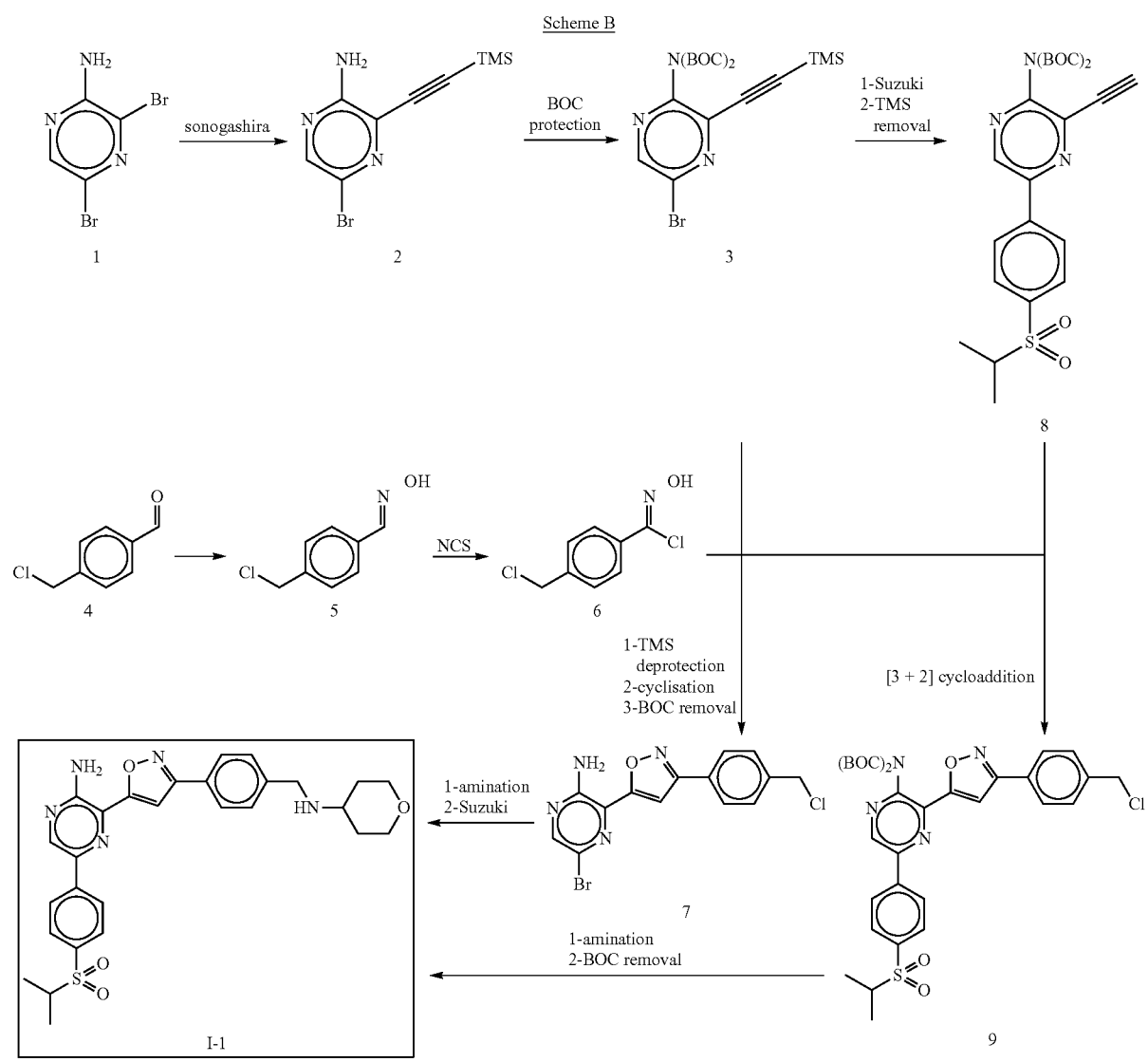

Scheme B

The compound of formula I-1 can also be made according to the method described in Scheme B.

Example 2

Synthesis of 5-(4-(Isopropylsulfonyl)phenyl)-3-(3-(4-(tetrahydropyran-4-ylamino)methyl)phenyl) isoxazol-5-yl)pyrazin-2-amine (Compound I-1)

Step 1:
5-Bromo-3-((trimethylsilyl)ethynyl)pyrazin-2-amine 2

(Trimethylsilyl)acetylene (1.845 g, 2.655 mL, 18.78 mmol) was added dropwise to a solution of 3,5-dibromopyrazin-2-amine 1 (5 g, 19.77 mmol) in DMF (25 mL) Triethylamine (10.00 g, 13.77 mL, 98.85 mmol), copper(I) iodide (451.7 mg, 2.372 mmol) and Pd(PPh$_3$)$_4$ (1.142 g, 0.9885 mmol) were then added and the resulting solution stirred at RT for 30 minutes. The reaction mixture was diluted with EtOAc and water and the layers separated. The aqueous layer was extracted further with EtOAc and the combined organic layers washed with water, dried (MgSO$_4$) and concentrated in vacuo. The residue was purified by column chromatography eluting with 15% EtOAc/Petroleum ether to give the product as a yellow solid (3.99 g, 75% Yield). $^1$H NMR (400.0 MHz, DMSO) δ 0.30 (9H, s), 8.06 (1H, s); MS (ES+) 271.82

Step 2: tert-Butyl N-tert-butoxycarbonyl-N-[5-bromo-3-((trimethylsilyl)ethynyl) pyrazin-2-yl]carbamate 3

5-Bromo-3-(2-trimethylsilylethynyl)pyrazin-2-amine 2 (2.85 g, 10.55 mmol) was dissolved in DCM (89.06 mL) and treated with BOC anhydride (6.908 g, 7.272 mL, 31.65 mmol) followed by DMAP (128.9 mg, 1.055 mmol). The reaction was allowed to stir at ambient temperature for 2 hours. The mixture was then diluted with DCM and NaHCO$_3$ and the layers separated. The aqueous layer was extracted further with DCM, dried (MgSO$_4$), filtered and concentrated in vacuo. The resultant residue was purified by column chromatography eluting with dichloromethane to give the desired product as a colourless oil (4.95 g, 99% Yield). ¹H NMR (400.0 MHz, DMSO) δ 0.27 (9H, s), 1.42 (18H, s), 8.50 (1H, s); MS (ES+) 472.09

Step 3: Di-tert-butyl 5-bromo-3-ethynylpyrazin-2-yliminodicarbonate

Sodium carbonate (918.5 µL of 2 M, 1.837 mmol) was added to a solution of tert-butyl N-[5-bromo-3-(2-trimethylsilylethynyl)pyrazin-2-yl]-N-tert-butoxycarbonyl-carbamate 3 (720 mg, 1.531 mmol) in DMF (2 mL) and the resulting solution was heated at 90° C. for 20 min. at RT. The reaction mixture was then partitioned between EtOAc (10 mL) and water (10 mL). The combined organic extract was sequentially washed with water (3×10 mL), brine, dried (MgSO₄) and concentrated in vacuo to yield the product as a yellow solid. ¹H NMR (400.0 MHz, DMSO) δ 1.35 (18H, s), 3.45 (1H, s), 8.47 (1H, s).

Step 4: 4-(Chloromethyl)benzaldehyde oxime 5

Hydroxylamine hydrochloride (10.11 g, 145.5 mmol) was added to a solution of 4-(chloromethyl)benzaldehyde 4 (7.5 g, 48.51 mmol) in EtOH. The mixture was heated at 50° C. for 3 h then concentrated in vacuo. The residue was partitioned between DCM and water. The combined organic extract was dried (MgSO₄) and concentrated in vacuo yielding a white solid that was used without further purification (8.1 g, 98%). ¹H NMR (400 MHz, DMSO) δ 4.77 (2H, s), 7.46 (2H, d, J=8.0 Hz), 7.60 (2H, d, J=8.0 Hz), 8.15 (1H, s), 11.32 (1H, s).

Step 5: 4-(Chloromethyl)-N-hydroxybenzimidoyl chloride 6

4-(chloromethyl)benzaldehyde oxime 5 (15.8 g, 93.16 mmol) was dissolved in DMF (300 mL). NCS (13.69 g, 102.5 mmol) was added in portions and then HCl in dioxane (100 mL of 4 M, 400.0 mmol) was added slowly, cooling the mixture with an ice water bath to moderate the exotherm, keeping internal temperature below 33° C. The mixture was then stirred at room temperature for 1 hour. The solution was partitioned between EtOAc and water and the organic extract was washed with water and brine (5×200 ml), dried over MgSO₄ and concentrated under reduced pressure to give a colourless solid (21.65 g, 95%). ¹H NMR (400 MHz, CDCl₃) δ 4.63 (2H, s), 7.45 (2H, d, J=8 Hz), 7.86 (2H, d, J=8 Hz), 8.36 (1H, s).

Step 6: 5-Bromo-3-(3-(4-(chloromethyl)phenyl)isoxazol-5-yl)pyrazin-2-amine 7

Triethylamine (330.3 mg, 455.0 µL, 3.264 mmol) was added to a solution of tert-butyl N-(5-bromo-3-ethynylpyrazin-2-yl)-N-tert-butoxycarbonyl-carbamate (1000 mg, 2.511 mmol) and 4-(chloromethyl)-N-hydroxy-benzimidoyl chloride 6 (563.6 mg, 2.762 mmol) in DCM (7 mL). The mixture was stirred at RT overnight. The reaction mixture was partitioned between DCM and water and the organic extract was dried (MgSO₄) and concentrated in vacuo yielding an oil that was dissolved in DCM (10 mL). TFA (2 mL) was added and the mixture was stirred at RT for 15 min before being concentrated in vacuo. MS (ES-) 364

Step 7: tert-Butyl N-(3-ethynyl-5-(4-(isopropylsulfonyl)phenyl)pyrazin-2-yl)N-tert-butoxycarbonyl-carbamate tert-butyl 8

N-[5-bromo-3-(2-trimethylsilylethynyl)pyrazin-2-yl]-N-tertbutoxycarbonyl-carbamate 3 (3 g, 6.377 mmol) and (4-isopropylsulfonylphenyl)boronic acid (1.491 g, 6.536 mmol) were dissolved in MeCN/water (60/12 mL). K₃PO₄ (2.706 g, 12.75 mmol) was added and the reaction mixture was degassed with a flow of nitrogen (5 cycles). Pd[P(tBu)₃]₂ (162.9 mg, 0.3188 mmol) was added and the resulting mixture was stirred at room temperature for 1 h. The reaction mixture was poured quickly into a mixture of ethyl acetate (500 mL), water (90 mL) and 1% aqueous sodium metabisulphite at 4° C., shaken well and the layer separated. The organic fraction was dried over MgSO₄, filtered and the filtrate was treated with 3-mercaptopropyl ethyl sulphide on silica (0.8 mmol/g, 1 g), pre-absorbed onto silica gel then purified by column chromatography on silica gel eluting with 30-40% EtOAc/petroleum ether. The solvents were concentrated in vacuo to leave the product as a yellow viscous oil that was triturated with petroleum ether to yield the product as beige crystals (1.95 g, 61%); ¹H NMR (400 MHz, DMSO) δ 1.20 (m, 6H), 1.39 (s, 18H), 3.50 (m, 1H), 5.01 (s, 1H), 8.03 (m, 2H), 8.46 (m, 2H) and 9.37 (s, 1H).

Step 8: tert-Butyl N-tert-butoxycarbonyl-N-[3-[3-[4-(chloromethyl)phenyl]isoxazol-5-yl]-5-(4-isopropylsulfonylphenyl)pyrazin-2-yl]carbamate 9

Triethylamine (899.0 mg, 1.238 mL, 8.884 mmol) was added to a solution of tert-butyl N-tert-butoxycarbonyl-N-[3-ethynyl-5-(4-isopropylsulfonylphenyl)pyrazin-2-yl]carbamate 8 (4.05 g, 8.074 mmol) and 4-(chloromethyl)-N-hydroxybenzimidoyl chloride (2.063 g, 8.494 mmol) in DCM (12 mL). The mixture was stirred at RT for 22 h then partitioned between DCM and an ice/water solution. The combined organic extract was dried over MgSO₄ and concentrated under reduced pressure then purified by chromatography on silica gel (eluent 30-50% EtAc/petrol) yielding tert-butyl N-tert-butoxycarbonyl-N-[3-[3-[4-(chloromethyl)phenyl]isoxazol-5-yl]-5-(4-isopropylsulfonylphenyl)pyrazin-2-yl] carbamate as colourless crystals (4.53 g, 79%). ¹H NMR (400 MHz, CDCl₃) δ 1.41 (18H, s), 4.66 (2H, s), 7.37 (1H, s), 7.54 (2H, d, J=8.0 Hz), 7.90 (2H, d, J=8.0 Hz), 8.66 (1H, s)

Step 9: 5-(4-(Isopropylsulfonyl)phenyl)-3-(3-(4-(tetrahydropyran-4-ylamino)methyl)phenyl) isoxazol-5-yl)pyrazin-2-amine (Compound I)

A solution of tert-butyl N-tert-butoxycarbonyl-N-[3-[3-[4-(chloromethyl)phenyl]isoxazol-5-yl]-5-(4-isopropylsulfonylphenyl)pyrazin-2-yl]carbamate 9 (4.1 g, 6.127 mmol), 4-aminotetrahydro-2H-pyran (2.479 g, 24.51 mmol), KI (1.017 g, 324.9 µL, 6.127 mmol) and DIPEA (791.9 mg, 1.067 mL, 6.127 mmol) in DMF (51 mL) was stirred at 40° C. for 3 h then stirred overnight at rt. The mixture was slowly poured onto a stirred ice/water mixture (400 ml) and stirred at rt overnight. The mixture was filtered and washed with water to give a wet paste which was dissolved in warm EtAc (500 ml), washed with water then brine, dried over MgSO₄ and concentrated under reduced pressure to give a yellow foam. The above material was dissolved into DCM (40 mL) and treated at RT with TFA (8 mL, 103.8 mmol). The mixture was stirred for 1 h at RT, then concentrated under reduced pressure. The residue was azeotroped three times with a DCM/MeOH yielding a yellow solid that was stirred in a mixture of ethanol (50 mL) and water (50 mL). Excess potassium carbonate (20 mL of 0.5 M, 10 mmol) was added and the mixture was stirred for 45 min at RT. The solid was filtered off, washed with water and dried under high vacuum at 77° C. to give 5-(4-isopropylsulfonylphenyl)-3-[3-[4-[(tetrahydropyran-4-ylamino)methyl]phenyl]isoxazol-5-yl]pyrazin-2-amine (2.857 g, 5.354 mmol) as a free base.

Step 10: 5-(4-(Isopropylsulfonyl)phenyl)-3-(3-(4-(tetrahydropyran-4-ylamino)methyl)phenyl)isoxazol-5-yl)pyrazin-2-amine (Compound I) Hydrochloride Formation To methanol (20 ml) at 0° C. was added dropwise acetyl chloride (420 µL, 5.907 mmol). The mixture was stirred for 10 min. and this solution was then added dropwise to a solution of 5-(4-isopropylsulfonylphenyl)-3-[3-[4-[(tetrahydropyran-4-ylamino)methyl]phenyl]isoxazol-5-yl]pyrazin-2-amine I (2.857 g, 5.354 mmol) in DCM (100 mL) and methanol (20 mL). The mixture was stirred at RT overnight. The yellow precipitate was filtered off and washed with anhydrous DCM then dried under high vacuum at 65-70° C. to give 2.07 g of pure hydrochloride salt. $^1$H NMR (400 MHz, DMSO) δ 1.19 (6H, d), 1.62-1.75 (2H, m), 2.02-2.07 (2H, m), 3.26-3.35 (3H, m), 3.90-3.97 (2H, dd), 4.25-4.29 (2H, m), 7.25 (2H, br hump), 7.79 (2H, d), 7.86 (1H, s), 7.94 (2H, d), 8.12 (2H, d), 8.39 (2H, d), 8.97 (1H, s), 9.35 (2H, br s); MS (ES+) 534.3.

The compound of formula I-1 can be made according to the method described in Schemes A or B.

Synthesis of Deuterated Analogs

Scheme C: Formation of d1-boronate

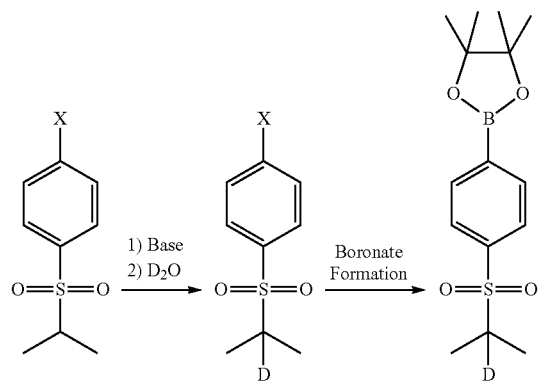

Scheme C shows a general synthetic method for the preparation of d1-boronate intermediates. A suitable 1-halo-(isopropylsulfonyl)benzene is treated with a base such as, but not limited to NaH, LiHMDS or KHMDS followed by quenching of the anion with deuterium source such as D$_2$O. The halogen is then transformed into a suitable boronate derivative via, for example, metal mediated cross-coupling catalyzed by, for instance, Pd($^t$Bu$_3$)$_2$ or Pd(dppf)Cl$_2$.DCM.

Scheme D: Formation of d6-boronate

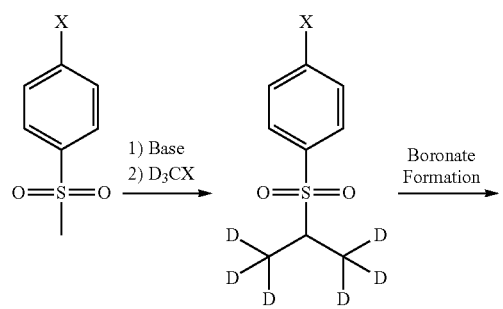

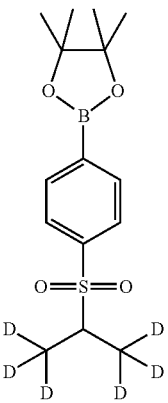

Scheme D shows a general synthetic method for the preparation of d6-boronate intermediates. A suitable 1-halo-(methylsulfonyl)benzene is treated with a base such as, but not limited to NaH, LiHMDS or KHMDS followed by quenching of the anion with deuterium source such as D$_3$CI. This reaction is repeated until the desired amount of deuterium has been incorporated into the molecule. The halogen is then transformed into a suitable boronate derivative via, for example, metal mediated cross-coupling catalyzed by, for instance, Pd($^t$Bu$_3$)$_2$ or Pd(dppf)Cl$_2$.DCM.

Scheme E: Formation of d7-boronate

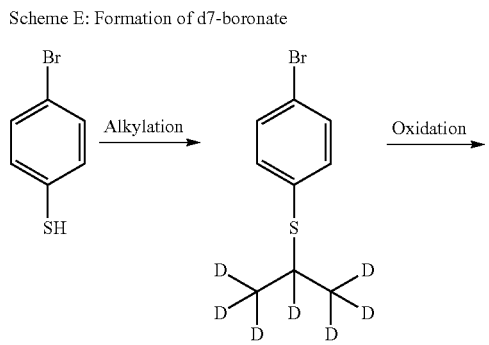

Scheme E shows a general synthetic method for the preparation of d7-boronate intermediates. 4-Bromobenzenethiol is treated with a base such as, but not limited to NaH, LiHMDS or KHMDS followed by quenching of the anion with deuterium source such as 1,1,1,2,3,3,3-heptadeuterio-2-iodo-propane. The sulfide is then oxidized to the corresponding sulfone using, for example, mCPBA or Oxone. The halogen is then transformed into a suitable boronate derivative via, for example, metal mediated cross-coupling catalyzed by, for instance, Pd($^t$Bu$_3$)$_2$ or Pd(dppf)Cl$_2$.DCM.

Scheme F: Formation of aryl ring deuterated boronate

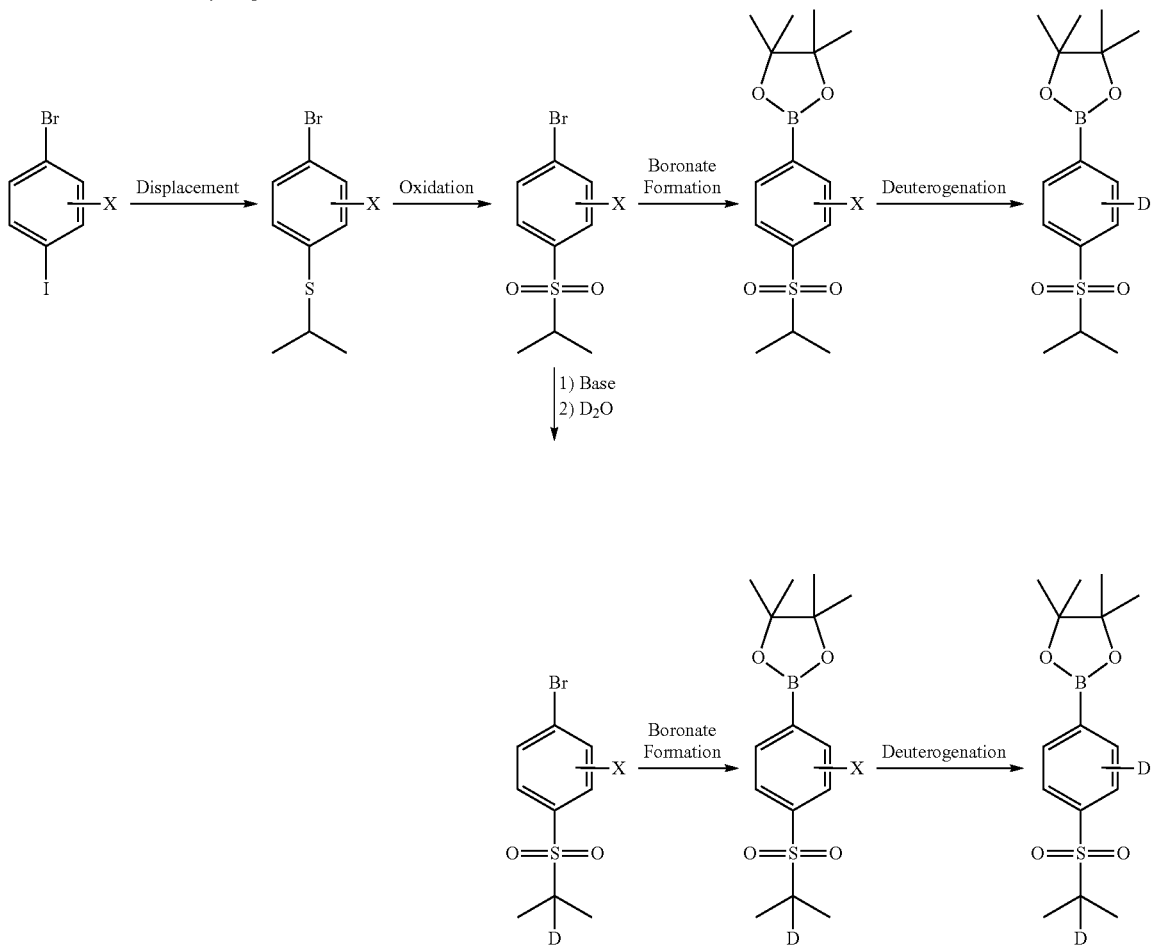

Scheme F shows a general synthetic method for the preparation of boronate intermediates where the aryl ring is substituted with a deuterium. A suitable 1-iodo-4-bromo-aryl derivative is treated with a substituted thiol such as propane-2-thiol under metal catalyzed coupling conditions using a catalyst such as CuI. The sulfide is then oxidized to the corresponding sulfone using, for example, mCPBA or Oxone. The bromide is then transformed into a suitable boronate derivative via, for example, metal mediated cross-coupling catalyzed by, for instance, Pd($^t$Bu$_3$)$_2$ or Pd(dppf)Cl$_2$.DCM. The remaining substituent is then converted into deuterium by, for instance, metal catalyzed halogen-deuterium exchange using a suitable metal catalyst, such as Pd on C under an atmosphere of deuterium gas. In addition, the 1-bromo-(isopropylsulfonyl)benzene can be treated with a base such as, but not limited to NaH, LiHMDS or KHMDS followed by quenching of the anion with deuterium source such as D$_2$O. The bromide is then transformed into a suitable boronate derivative via, for example, metal mediated cross-coupling catalyzed by, for instance, Pd($^t$Bu$_3$)$_2$ or Pd(dppf)Cl$_2$.DCM. The remaining substituent is then converted into deuterium by, for instance, metal catalyzed halogen-deuterium exchange using a suitable metal catalyst, such as Pd on C under an atmosphere of deuterium gas.

Scheme G: Formation of aryl ring deuterated boronate

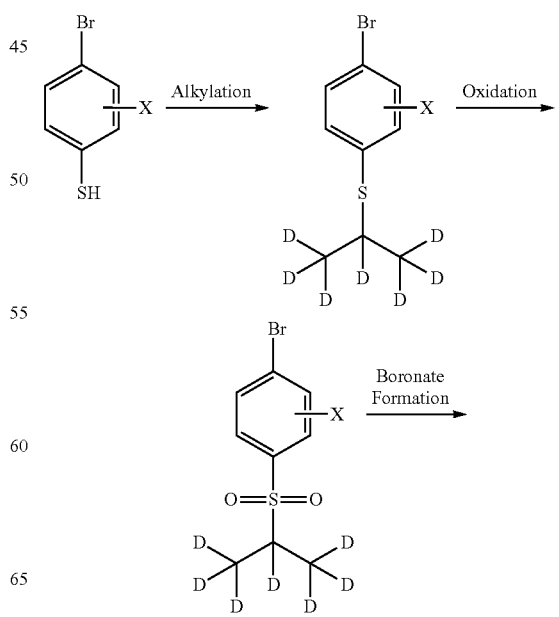

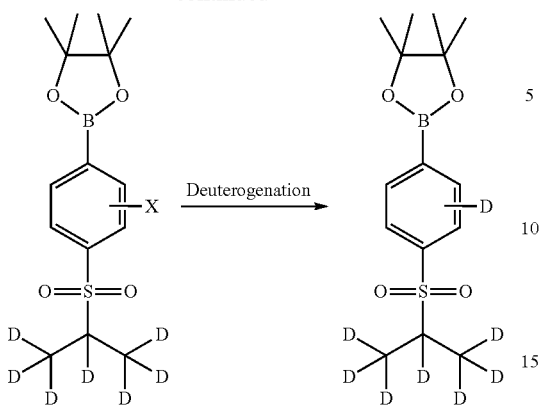

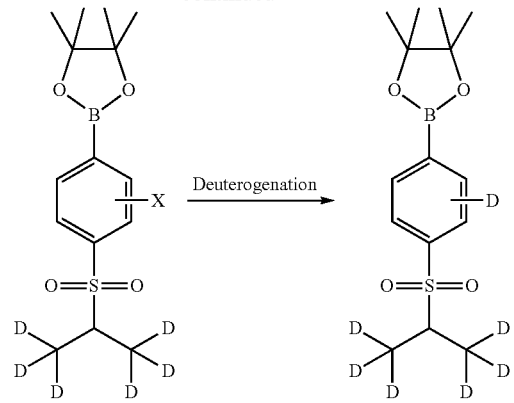</p>

Scheme G shows another general synthetic method for the preparation of boronate intermediates where the aryl ring is substituted with a deuterium. A substituted 4-bromobenzenethiol is treated with a base such as, but not limited to NaH, LiHMDS or KHMDS followed by quenching of the anion with deuterium source such as 1,1,1,2,3,3,3-heptadeuterio-2-iodo-propane. The sulfide is then oxidized to the corresponding sulfone using, for example, mCPBA or Oxone. The halogen is then transformed into a suitable boronate derivative via, for example, metal mediated cross-coupling catalyzed by, for instance, Pd($^t$Bu$_3$)$_2$ or Pd(dppf)Cl$_2$.DCM. The remaining substituent is then converted into deuterium by, for instance, metal catalyzed halogen-deuterium exchange using a suitable metal catalyst, such as Pd on C under an atmosphere of deuterium gas.

Scheme H: Formation of aryl ring deuterated boronate

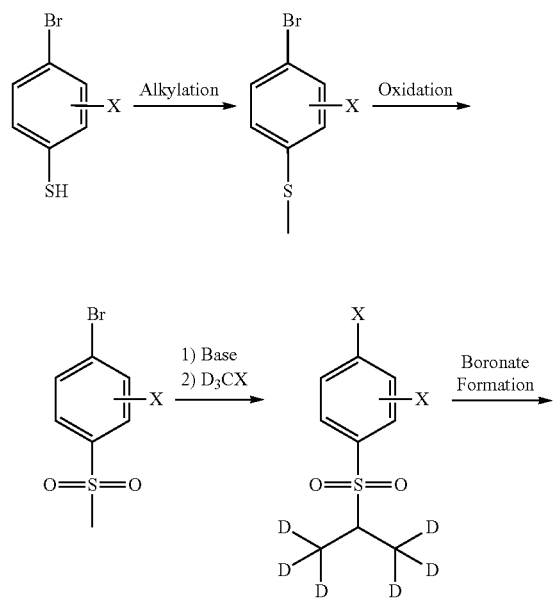

Scheme H shows another general synthetic method for the preparation of boronate intermediates where the aryl ring is substituted with a deuterium. A substituted 4-bromobenzenethiol is treated with a base such as, but not limited to NaH, LiHMDS or KHMDS followed by quenching of the anion with for instance MeI. The sulfide is then oxidized to the corresponding sulfone using, for example, mCPBA or Oxone. The sulfone is treated with a base such as, but not limited to NaH, LiHMDS or KHMDS followed by quenching of the anion with deuterium source such as D$_3$CI. This reaction is repeated until the desired amount of deuterium has been incorporated into the molecule. The halogen is then transformed into a suitable boronate derivative via, for example, metal mediated cross-coupling catalyzed by, for instance, Pd($^t$Bu$_3$)$_2$ or Pd(dppf)Cl$_2$.DCM. The remaining substituent is then converted into deuterium by, for instance, metal catalyzed halogen-deuterium exchange using a suitable metal catalyst, such as Pd on C under an atmosphere of deuterium gas.

Scheme I: Formation of aryl ring deuterated oxime intermediates

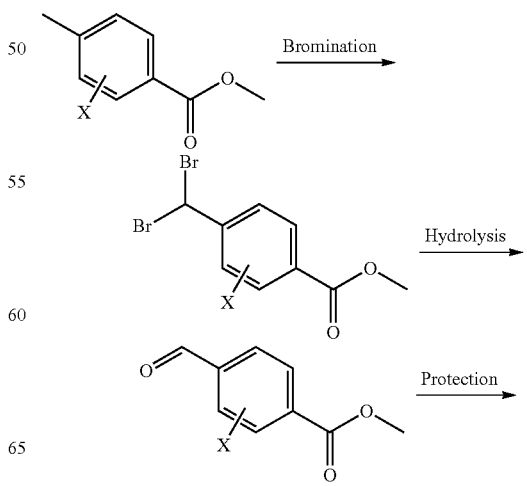

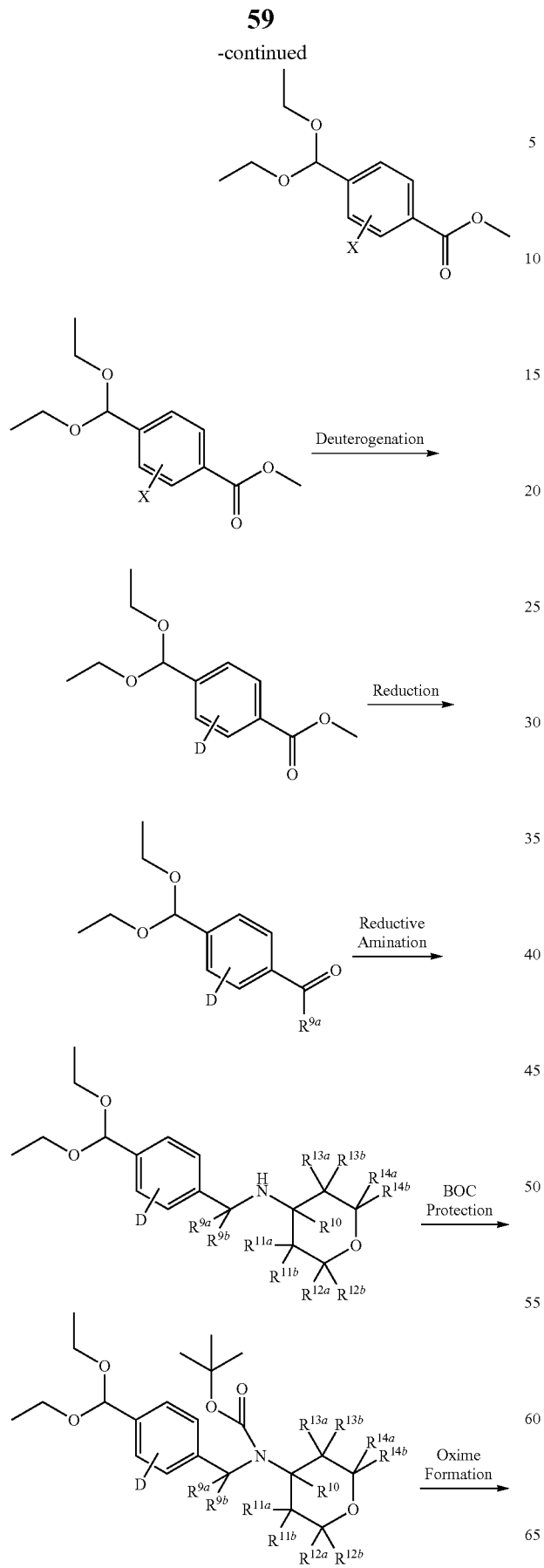
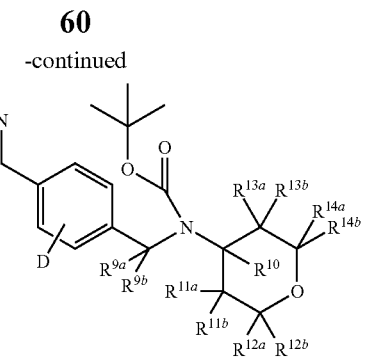

Scheme I shows a general synthetic method for the preparation of oxime intermediates where the aryl ring is substituted with a deuterium. The methyl group of an appropriately substituted methyl 4-methylbenzoate derivative can be converted into the corresponding dibromide under conditions such as AIBN catalyzed bromination with NBS. This dibromide is then hydrolysed to the corresponding aldehyde, for instance using $AgNO_3$ in acetone/water. Protection of the aldehyde as a suitable acetal, for instance the diethyl acetal and subsequent conversion of the remaining substituent into deuterium by, for instance, metal catalyzed halogen-deuterium exchange using a suitable metal catalyst, such as Pd on C under an atmosphere of deuterium gas gives the deuterated ester intermediate. The ester functionality can be reduced using reagents such as $LiAlH_4$, $NaBH_4$, $NaBD_4$ or $LiAlD_4$ to give corresponding aldehyde. This can be reacted under reductive amination conditions using a suitable amine, such as methylamine or d3-methylamine using a reducing agent such as $NaBH_4$ or $NaBD_4$ to give the corresponding amine derivative. This can be protected with, for instance a BOC group and the acetal converted into the oxime using, for instance, hydroxylamine hydrochloride in THF/water.

Scheme J: Formation of aryl ring deuterated oxime intermediates

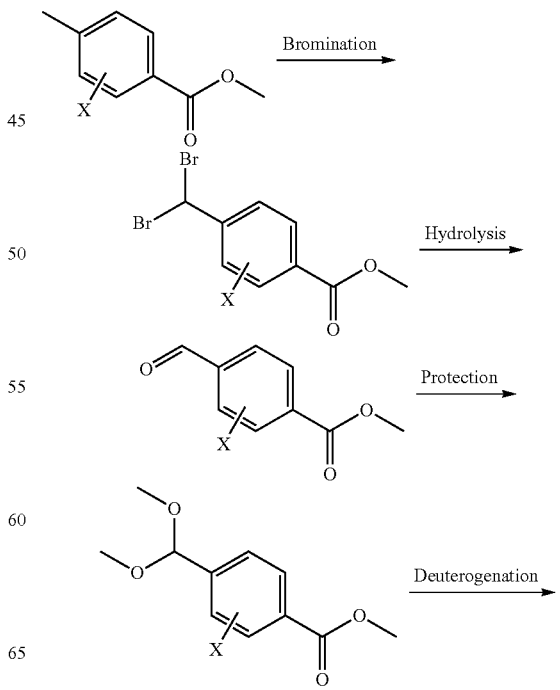

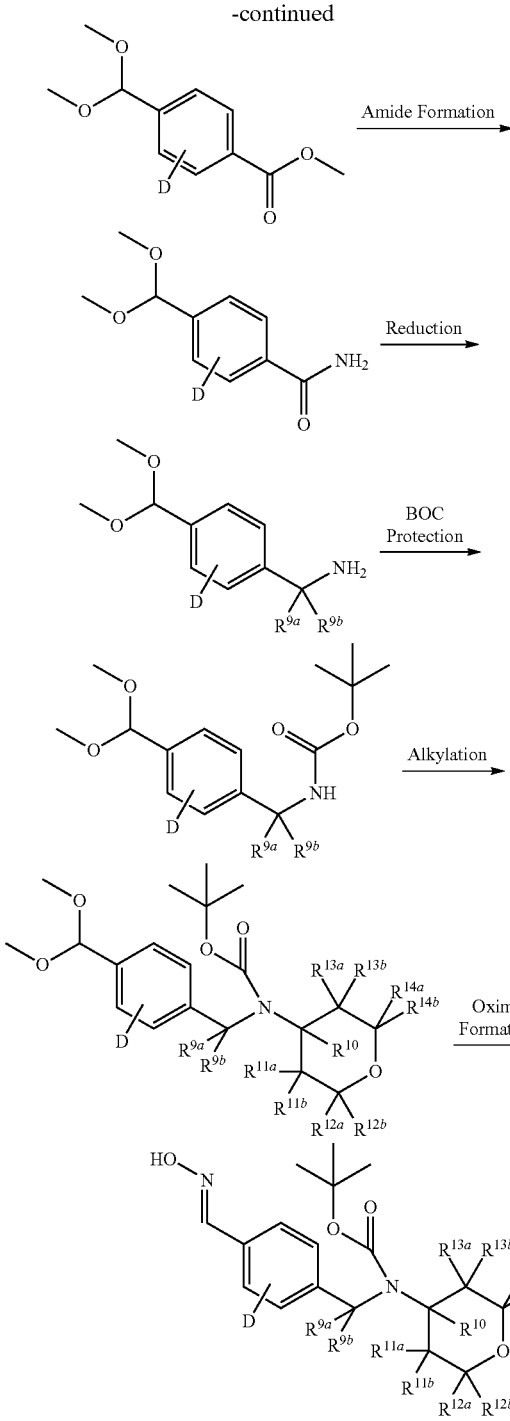

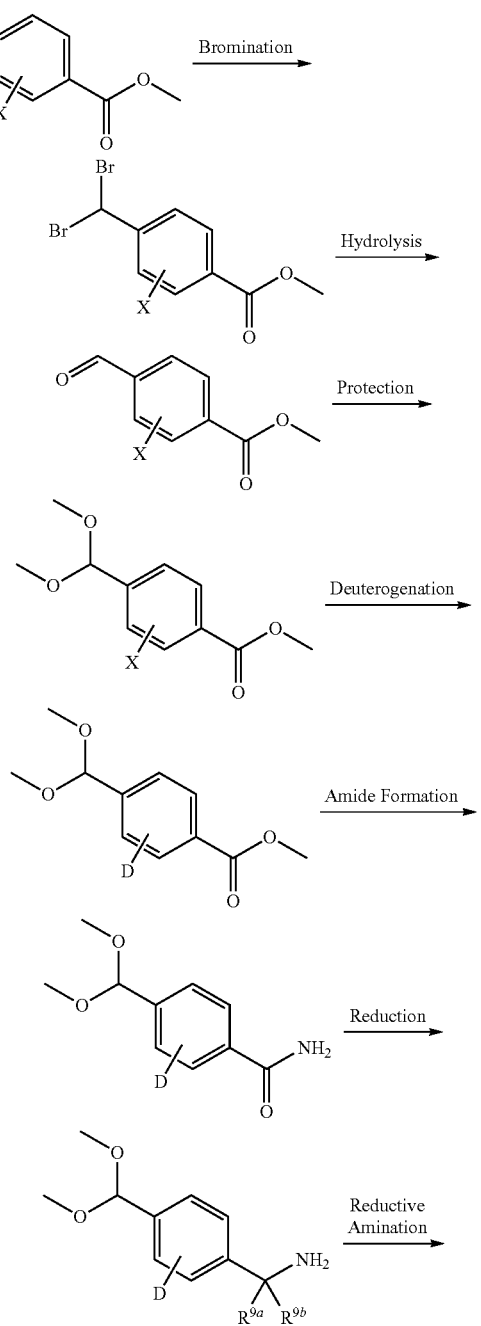

C under an atmosphere of deuterium gas gives the deuterated ester intermediate. The ester functionality can be converted into the corresponding primary amide under standard conditions, such as heating with a solution of ammonia in methanol. The amide can be reduced to the corresponding amine using reagents not limited to $LiAlH_4$ or $LiAlD_4$. This can be protected with, for instance a BOC group. The carbamate NH can be alkylated under basic conditions using for instance NaH, LiHMDS or KHMDS followed by quenching of the anion with deuterium source such MeI or $D_3CI$. The acetal can be converted into the oxime using, for instance, hydroxylamine hydrochloride in THF/water.

Scheme K: Formation of aryl ring deuterated oxime intermediates

Scheme J shows another general synthetic method for the preparation of oxime intermediates where the aryl ring is substituted with a deuterium. The methyl group of an appropriately substituted methyl 4-methylbenzoate derivative can be converted into the corresponding dibromide under conditions such as AIBN catalyzed bromination with NBS. This di-bromide is then hydrolysed to the corresponding aldehyde, for instance using $AgNO_3$ in acetone/water. Protection of the aldehyde as a suitable acetal, for instance the dimethyl acetal and subsequent conversion of the remaining substituent into deuterium by, for instance, metal catalyzed halogen-deuterium exchange using a suitable metal catalyst, such as Pd on

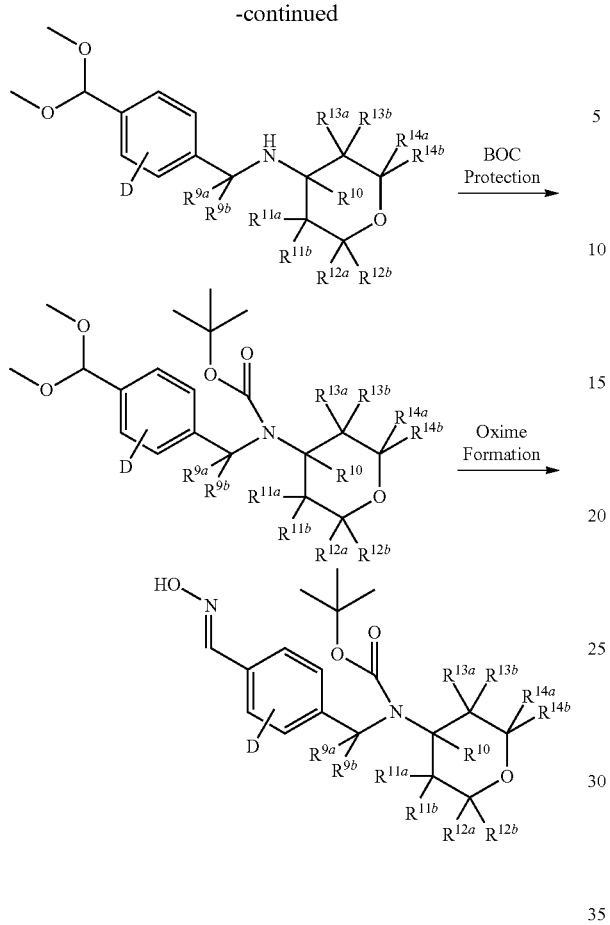

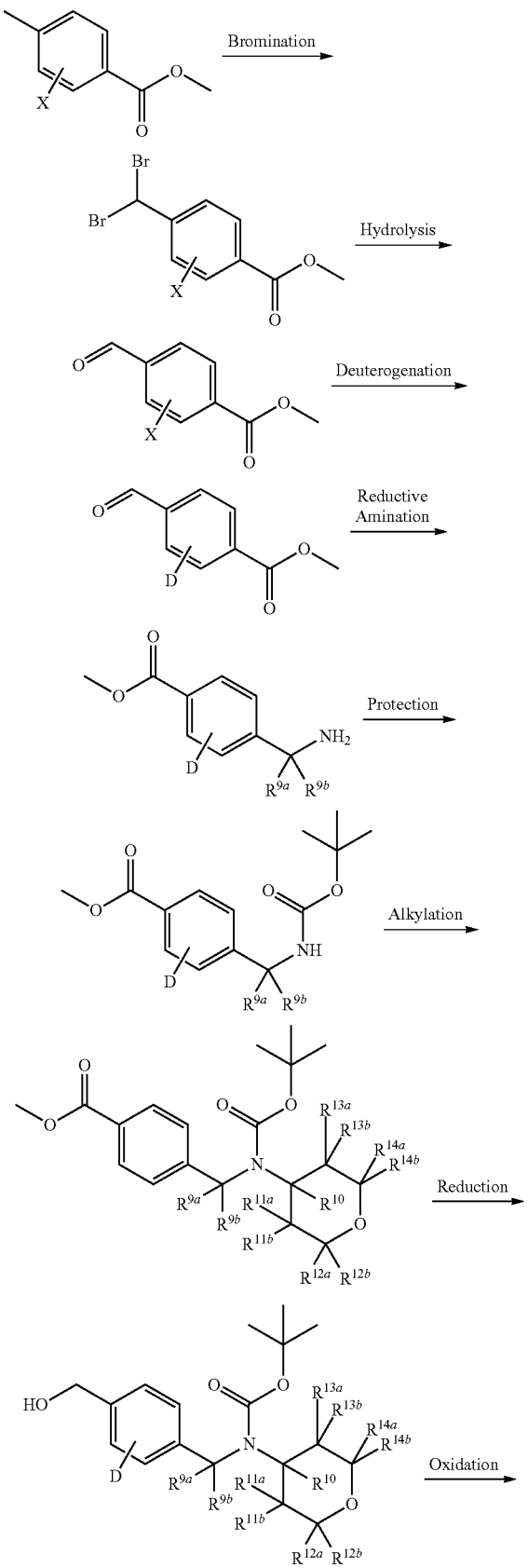

Scheme L: Formation of aryl ring deuterated oxime intermediates

Scheme K shows another general synthetic method for the preparation of oxime intermediates where the aryl ring is substituted with a deuterium. The methyl group of an appropriately substituted methyl 4-methylbenzoate derivative can be converted into the corresponding dibromide under conditions such as AIBN catalyzed bromination with NBS. This di-bromide is then hydrolysed to the corresponding aldehyde, for instance using $AgNO_3$ in acetone/water. Protection of the aldehyde as a suitable acetal, for instance the dimethyl acetal and subsequent conversion of the remaining substituent into deuterium by, for instance, metal catalyzed halogen-deuterium exchange using a suitable metal catalyst, such as Pd on C under an atmosphere of deuterium gas gives the deuterated ester intermediate. The ester functionality can be converted into the corresponding primary amide under standard conditions, such as heating with a solution of ammonia in methanol. The amide can be reduced to the corresponding amine using reagents not limited to $LiAlH_4$ or $LiAlD_4$. This can be reacted under reductive amination conditions using a suitable amine, such as methylamine, d3-methylamine, formaldehyde or d2-formaldehyde using a reducing agent such as $NaBH_4$ or $NaBD_4$ to give the corresponding amine derivative. This can be protected with, for instance a BOC group. The acetal can be converted into the oxime using, for instance, hydroxylamine hydrochloride in THF/water.

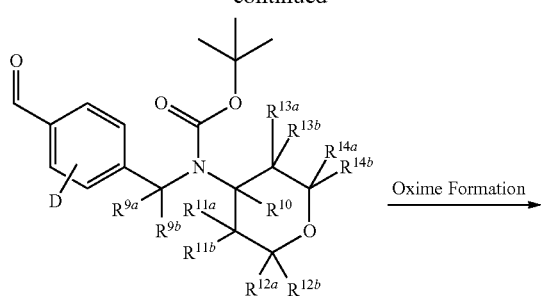

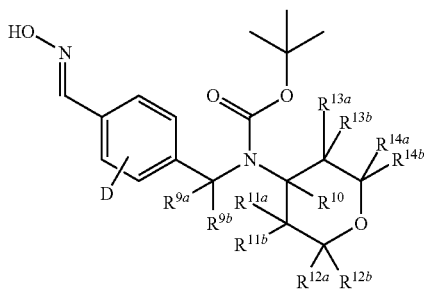

Scheme L shows another general synthetic method for the preparation of oxime intermediates where the aryl ring is substituted with a deuterium. The methyl group of an appropriately substituted methyl 4-methylbenzoate derivative can be converted into the corresponding dibromide under conditions such as AIBN catalyzed bromination with NBS. This di-bromide is then hydrolysed to the corresponding aldehyde, for instance using $AgNO_3$ in acetone/water. Protection of the aldehyde as a suitable acetal, for instance the dimethyl acetal and subsequent conversion of the remaining substituent into deuterium by, for instance, metal catalyzed halogen-deuterium exchange using a suitable metal catalyst, such as Pd on C under an atmosphere of deuterium gas gives the deuterated ester intermediate. This can be reacted under reductive amination conditions using a suitable amine, such as ammonium hydroxide using a reducing agent such as $NaBH_4$ or $NaBD_4$ to give the corresponding amine derivative. This can be protected with, for instance a BOC group and the carbamate NH alkylated under basic conditions using for instance NaH, LiHMDS or KHMDS followed by quenching of the anion with deuterium source such Met or $D_3Cl$. The ester can be reduced to the corresponding alcohol using a suitable reducing agent such as $LiBH_4$ or $NaBH_4$. The alcohol can be oxidized to the aldehyde using reagents such as $MnO_2$ or Dess-Martin periodane. The acetal can be converted into the oxime using, for instance, aqueous hydroxylamine.

Scheme M: Formation of deuterated oxime intermediates

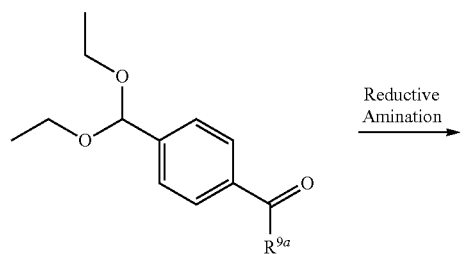

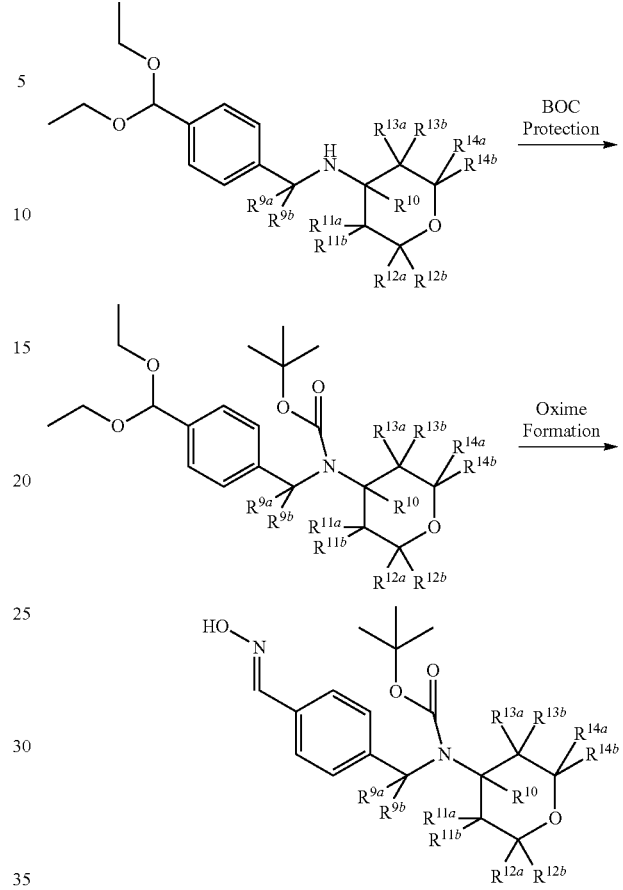

Scheme M shows a general synthetic method for the preparation of deuterated oxime intermediates. 4-(diethoxymethyl) benzaldehyde can be reacted under reductive amination conditions using a suitable amine, such as methylamine or d3-methylamine using a reducing agent such as $NaBH_4$ or $NaBD_4$ to give the corresponding amine derivative. This can be protected with, for instance a BOC group and the acetal converted into the oxime using, for instance, hydroxylamine hydrochloride in THF/water.

Scheme N: Formation of deuterated oxime intermediates

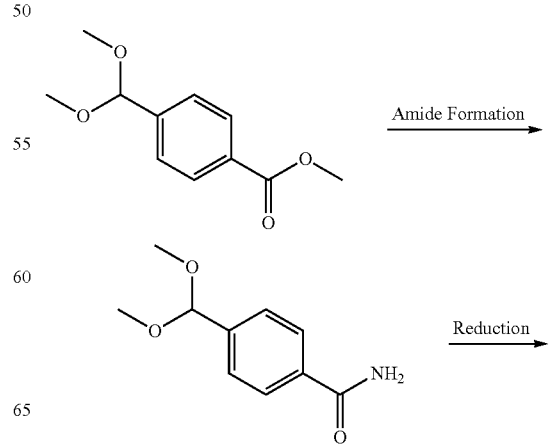

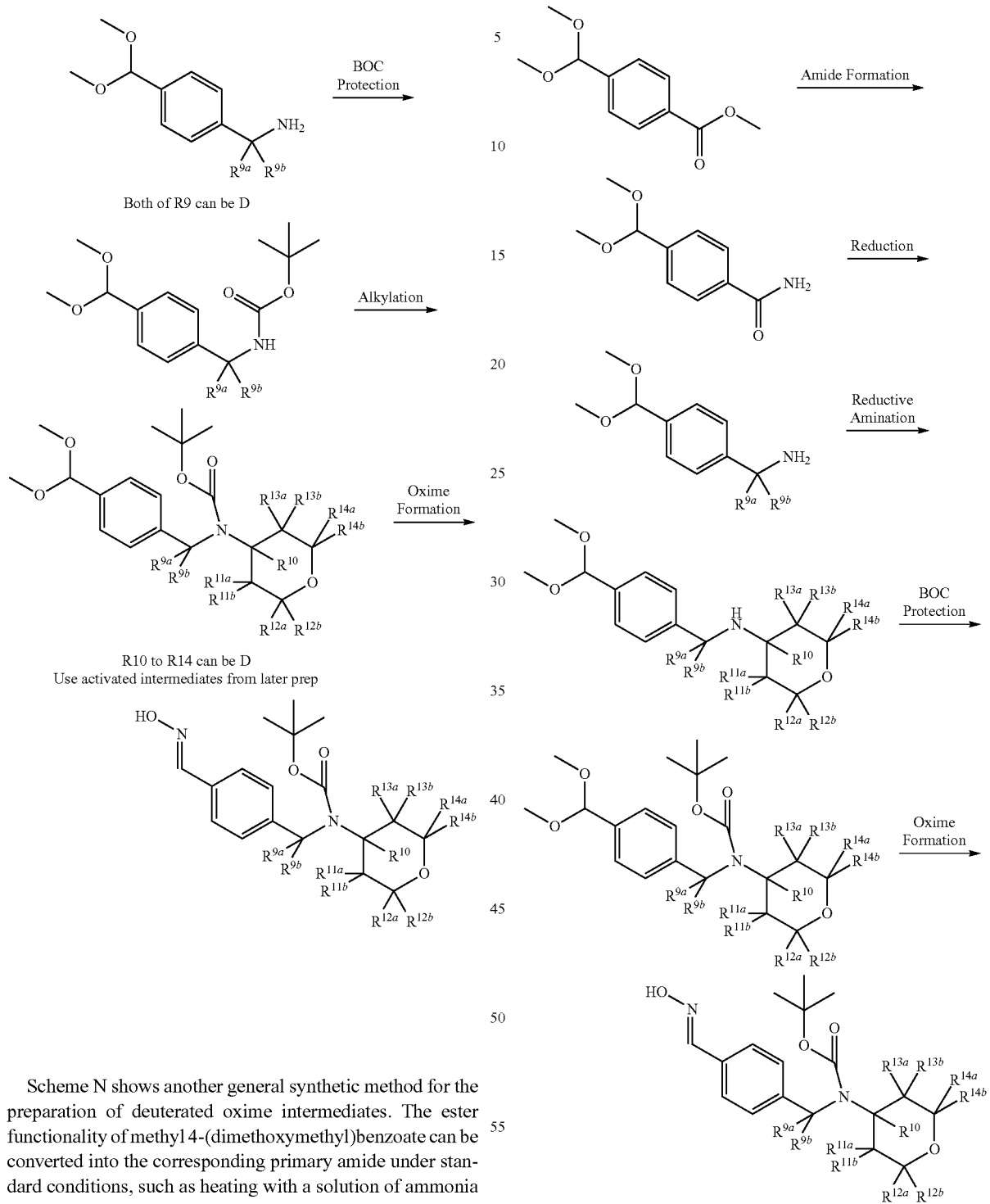

Scheme N shows another general synthetic method for the preparation of deuterated oxime intermediates. The ester functionality of methyl 4-(dimethoxymethyl)benzoate can be converted into the corresponding primary amide under standard conditions, such as heating with a solution of ammonia in methanol. The amide can be reduced to the corresponding amine using reagents not limited to LiAlH$_4$ or LiAlD$_4$. This can be protected with, for instance a BOC group. The carbamate NH can be alkylated under basic conditions using for instance NaH, LiHMDS or KHMDS followed by quenching of the anion with deuterium source such MeI or D$_3$Cl. The acetal can be converted into the oxime using, for instance, hydroxylamine hydrochloride in THF/water.

Scheme O shows another general synthetic method for the preparation of deuterated oxime intermediates. The ester functionality of methyl 4-(dimethoxymethyl)benzoate can be converted into the corresponding primary amide under standard conditions, such as heating with a solution of ammonia in methanol. The amide can be reduced to the corresponding amine using reagents not limited to LiAlH$_4$ or LiAlD$_4$. This can be reacted under reductive amination conditions using a suitable amine, such as methylamine, d3-methylamine, formaldehyde or d2-formaldehyde using a reducing agent such as NaBH$_4$ or NaBD$_4$ to give the corresponding amine derivative. This can be protected with, for instance a BOC group. The acetal can be converted into the oxime using, for instance, hydroxylamine hydrochloride in THF/water.

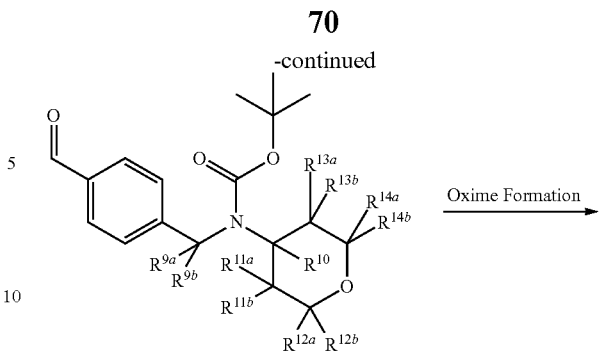

Scheme P: Formation of deuterated oxime intermediates

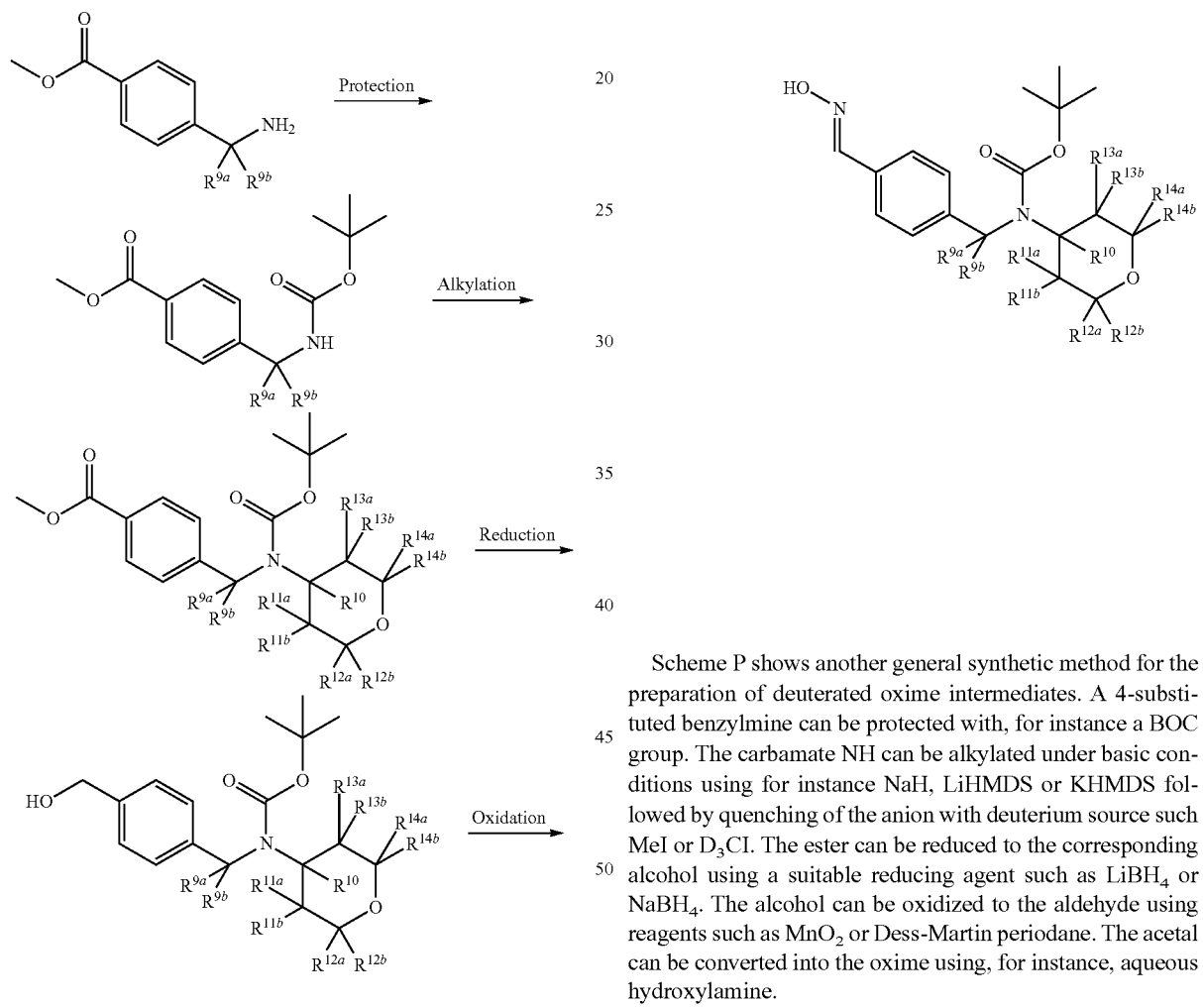

Scheme P shows another general synthetic method for the preparation of deuterated oxime intermediates. A 4-substituted benzylmine can be protected with, for instance a BOC group. The carbamate NH can be alkylated under basic conditions using for instance NaH, LiHMDS or KHMDS followed by quenching of the anion with deuterium source such MeI or D$_3$CI. The ester can be reduced to the corresponding alcohol using a suitable reducing agent such as LiBH$_4$ or NaBH$_4$. The alcohol can be oxidized to the aldehyde using reagents such as MnO$_2$ or Dess-Martin periodane. The acetal can be converted into the oxime using, for instance, aqueous hydroxylamine.

Scheme Q: Formation of isoxazole derivatives

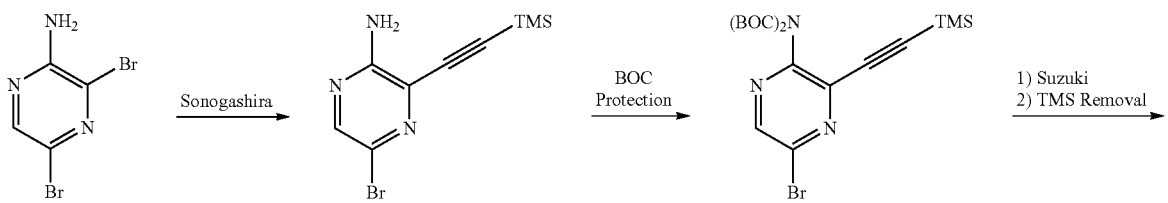

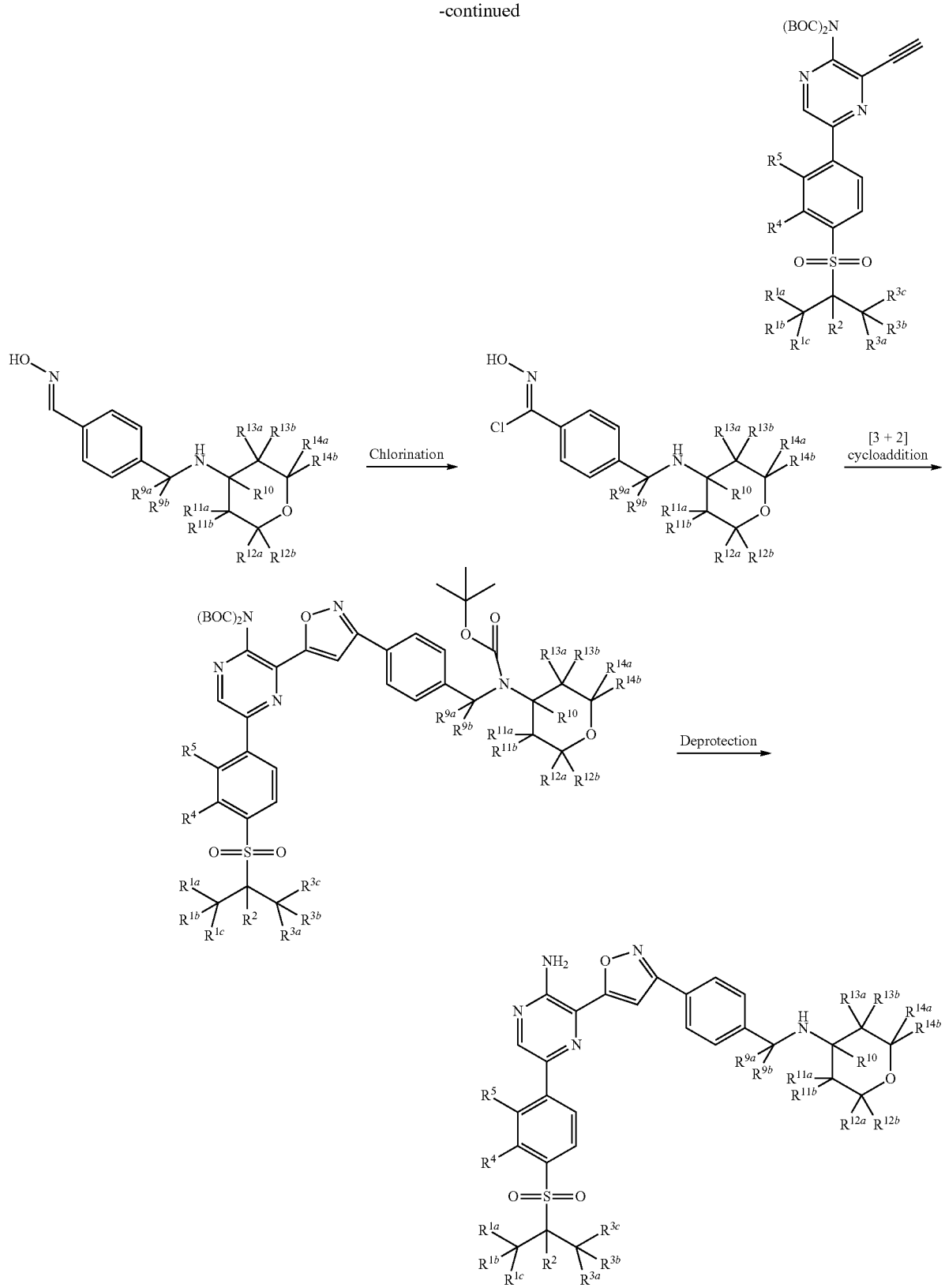
Scheme Q shows a general synthetic method for the preparation of deuterated pyrazine-isoxazole derivatives. 3,5-Dibromopyrazin-2-amine is converted into the corresponding silyl-protected alkyne under standard Sonagashira conditions utilizing, for example, Pd(PPh$_3$)$_4$ and CuI as catalysts. The pyrazine NH$_2$ can then be protected as, for example the di-BOC derivative. Coupling of the pyrazine bromide with a boronate, for instance those outlined in Schemes 1 to 6 above, under standard Suzuki cross-coupling conditions followed by removal of the silyl protecting group give the desired alkyne intermediate. Oximes, such as those outlined in Schemes 7 to 14 above, can be converted into the corresponding chlorooximes using, for instance, NCS. The alkyne and chlorooxime intermediates can undergo a [3+2] cycloaaditon to give corresponding isoxazole under standard conditions, for instance by the addition of $Et_3N$. The BOC protecting groups can be removed under acidic conditions such as TFA in DCM or HCl in MeOH/DCM to give the deuterated pyrazine isoxazole derivatives.

Scheme R: Formation of deuterated isoxazole derrivatives

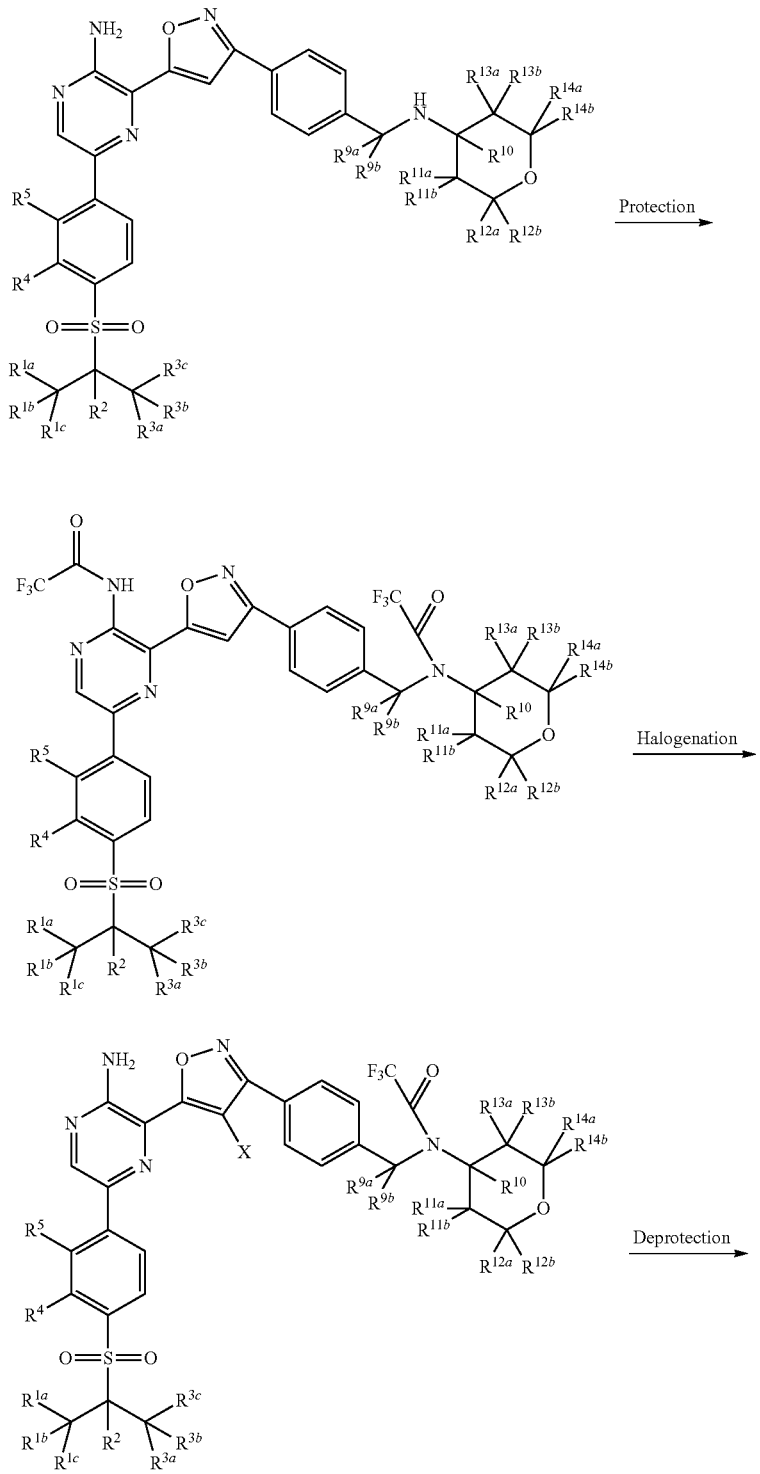

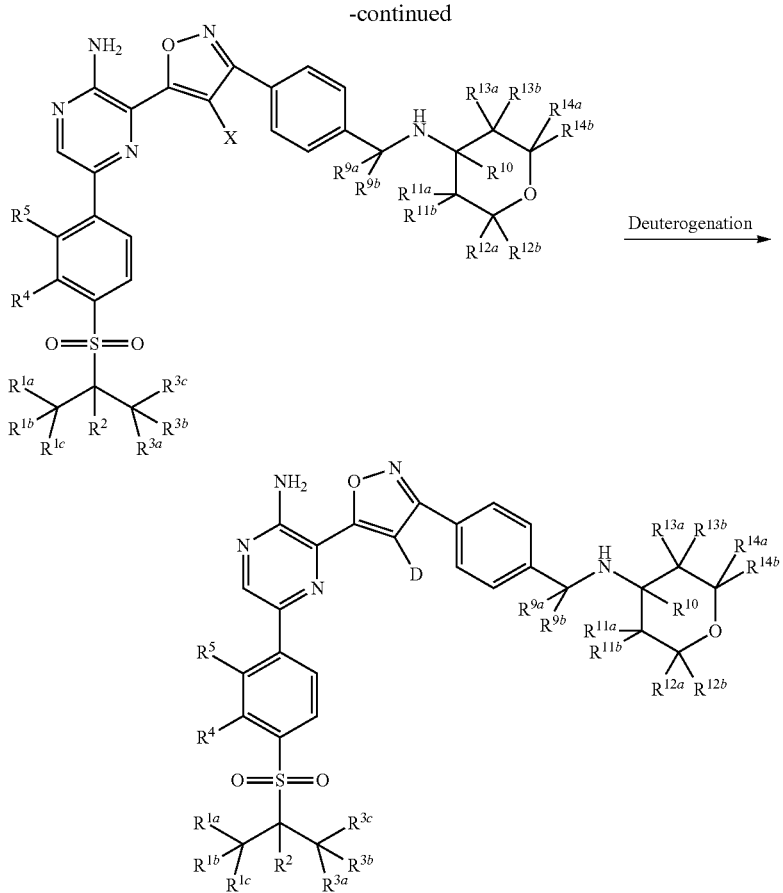

Scheme R shows a general synthetic method for the preparation of deuterated isoxazole derivatives. The pyrazine $NH_2$ and benzylamineamine NH can be protected under standard conditions using trifluoroacetic anhydride. Halogenation of the isoxazole ring with, for example NIS followed by removal of the trifluoroacetate protecting group under basic conditions provides the desired halogenated intermediates. The halogen can then converted into deuterium by, for instance, metal catalyzed halogen-deuterium exchange using a suitable metal catalyst, such as Pd on C under an atmosphere of deuterium gas.

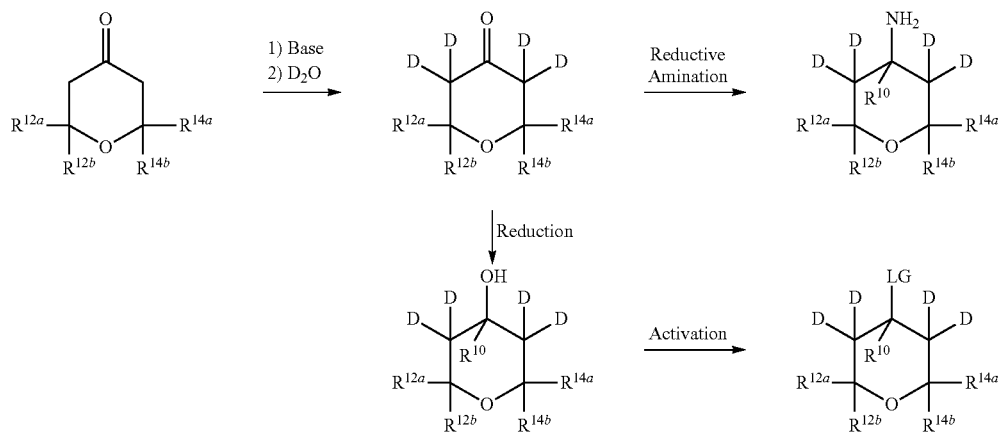

Scheme S: Formation of deuterated pyran derrivatives

Scheme S shows a general synthetic method for the preparation of deuterated pyran derivatives. A suitable pyranone is treated with a base such as, but not limited to NaH, LiHMDS or KHMDS followed by quenching of the anion with deuterium source such as $D_2O$. This reaction is repeated until the desired amount of deuterium has been incorporated into the molecule. This can be reacted under reductive amination conditions using a suitable amine, such as ammonium hydroxide using a reducing agent such as NaBH$_4$ or NaBD$_4$ to give the corresponding amine derivative. Alternatively the ketone can be reduced using reagents such as LiAlH$_4$, NaBH$_4$, NaBD$_4$ or LiAlD$_4$ to give corresponding alcohol. The alcohol can be further transformed into a leaving group such as mesylate or a halide.

Scheme T: Formation of deuterated pyran derrivatives

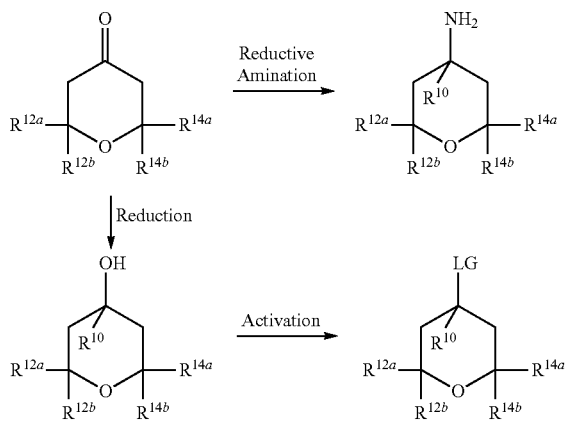

Scheme T shows another general synthetic method for the preparation of deuterated pyran derivatives. A suitable pyranone can be reacted under reductive amination conditions using a suitable amine, such as ammonium hydroxide using a reducing agent such as NaBH$_4$ or NaBD$_4$ to give the corresponding amine derivative. Alternatively the ketone can be reduced using reagents such as LiAlH$_4$, NaBH$_4$, NaBD$_4$ or LiAlD$_4$ to give corresponding alcohol. The alcohol can be further transformed into a leaving group such as mesylate or a halide.

Scheme U: Formation of deuterated pyran derrivatives

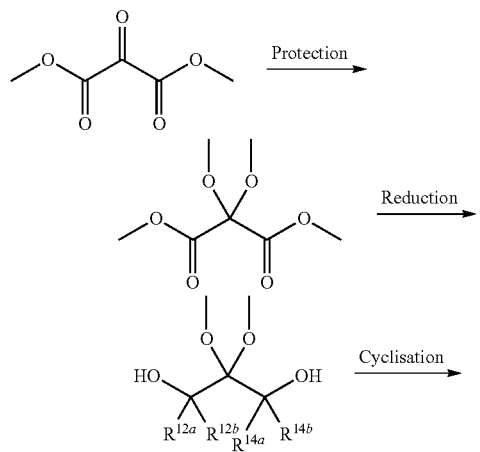

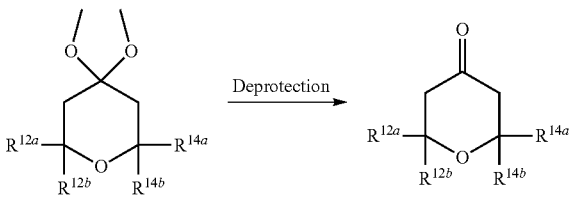

Scheme U shows another general synthetic method for the preparation of deuterated pyran derivatives. Ketoester such as dimethyl 2-oxomalonate can be protected as, for instance, a ketal. The ester functionality can be reduced using reagents such as LiAlH$_4$, NaBH$_4$, NaBD$_4$ or LiAlD$_4$ to give corresponding diol. This can be cyclized to the protected pyran derivative using, for example, Mitsunobu conditions. Ketal deprotection allows formation of the desired pyranone derivatives.

Example 3

Synthesis of 5-[4-[1,2,2,2-tetradeuterio-1-(trideuteriomethyl)ethyl]sulfonylphenyl]-3-[3-[4-[(tetrahydropyran-4-ylamino)methyl]phenyl]isoxazol-5-yl]pyrazin-2-amine (compound II-2)

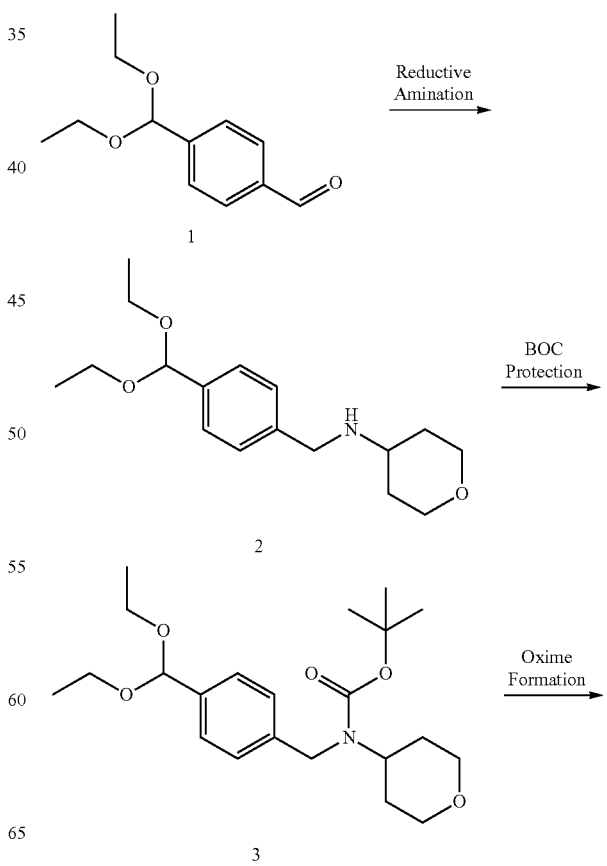

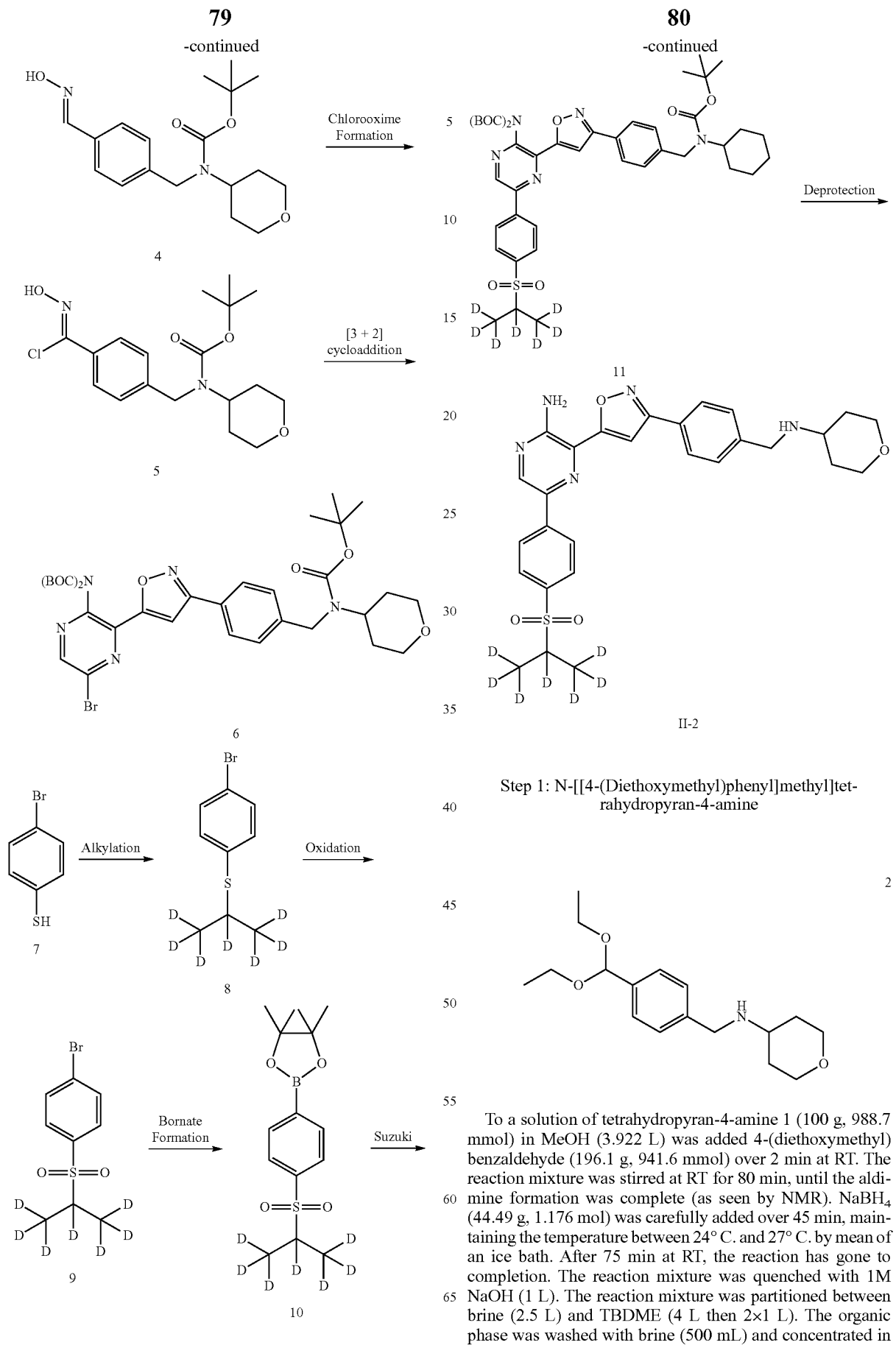

Step 1: N-[[4-(Diethoxymethyl)phenyl]methyl]tetrahydropyran-4-amine

To a solution of tetrahydropyran-4-amine 1 (100 g, 988.7 mmol) in MeOH (3.922 L) was added 4-(diethoxymethyl)benzaldehyde (196.1 g, 941.6 mmol) over 2 min at RT. The reaction mixture was stirred at RT for 80 min, until the aldimine formation was complete (as seen by NMR). NaBH$_4$ (44.49 g, 1.176 mol) was carefully added over 45 min, maintaining the temperature between 24° C. and 27° C. by mean of an ice bath. After 75 min at RT, the reaction has gone to completion. The reaction mixture was quenched with 1M NaOH (1 L). The reaction mixture was partitioned between brine (2.5 L) and TBDME (4 L then 2×1 L). The organic phase was washed with brine (500 mL) and concentrated in vacuo. The crude mixture was redissolved in DCM (2 L). The aqueous phase was separated, the organic phase was dried over MgSO₄, filtered and concentrated in vacuo to give the title compound as a yellow oil (252.99 g, 91% Yield); $^1$H NMR (400 MHz, CDCl₃) δ 1.26 (t, 6H), 1.43-1.52 (m, 2H), 1.85-1.89 (m, 2H), 3.40 (td, 2H), 3.53-3.66 (m, 4H), 3.85 (s, 2H), 4.00 (dt, 2H), 5.51 (s, 1H), 7.33 (d, 2H) and 7.45 d, 2H) ppm; MS (ES+) 293.9.

Step 2: tert-Butyl N-[[4-(diethoxymethyl)phenyl]methyl]-N-tetrahydropyran-4-yl-carbamate

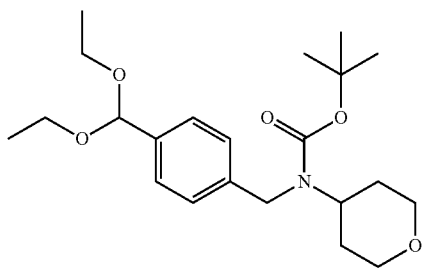

3

A solution of N-[[4-(diethoxymethyl)phenyl]methyl]tetrahydropyran-4-amine (252.99 g, 862.3 mmol) and BOC anhydride (191.9 g, 202.0 mL, 879.5 mmol) in DCM (2.530 L) was cooled down to 3.3° C. Et₃N (89.00 g, 122.6 mL, 879.5 mmol) was added over 4 min, keeping the internal temperature below 5° C. The bath was removed 45 min after the end of the addition. And the reaction mixture was stirred at RT overnight. The reaction mixture was sequentially washed with 0.5 M citric acid (1 L), saturated NaHCO₃ solution (1 L) and brine (1 L). The organic phase was dried (MgSO₄), filtered and concentrated in vacuo to give a colourless oil (372.38 g, 110% Yield) that was used without further purification; $^1$H NMR (400.0 MHz, CDCl₃) δ 1.25 (t, 6H), 1.40 (s, 9H), 1.47-1.70 (m, 5H), 3.41 (br s, 2H), 3.53-3.67 (m, 4H), 3.96 (dd, 2H), 4.41 (br s, 2H), 5.51 (s, 1H), 7.23 (d, 2H) and 7.42 (d, 2H) ppm.

Step 3: tert-Butyl N-[[4-hydroxyiminomethyl]phenyl]methyl]-N-tetrahydropyran-4-yl-carbamate

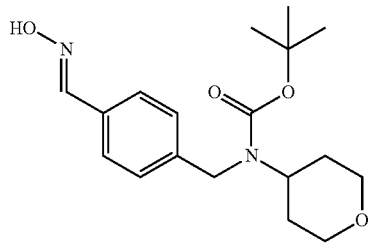

4 tert-Butyl N-[[4-(diethoxymethyl)phenyl]methyl]-N-tetrahydropyran-4-yl-carbamate (372.38 g, 946.3 mmol) was dissolved in THF (5 L) and water (500 mL). Hydroxylamine hydrochloride (72.34 g, 1.041 mol) was added in one portion and the reaction mixture was stirred overnight at RT. The reaction mixture was partitioned between DCM (5 L) and water. The combined organic extract was washed with water (1 L×2). The organic phase was concentrated in vacuo to a volume of about 2 L. The organic layer was dried over MgSO₄, filtered and concentrated in vacuo to give a sticky colourless oil that crystallized on standing under vacuum. (334.42 g, 106%). $^1$H NMR (400.0 MHz, CDCl₃) δ 1.40 (s, 9H), 1.47-1.69 (m, 2H), 1.86-1.89 (m, 1H), 3.43 (br s, 1H), 3.77 (t, 1H), 3.97 (dd, 2H), 4.42 (s, 2H), 5.32 (s, 1H), 7.27 (d, 2H), 7.53 (d, 2H), 7.85 (s, 1H) and 8.14 (s, 1H) ppm; MS (ES+) 325.2 (M-BOC).

Step 4: tert-Butyl N-[[4-[chloro-N-hydroxy-carbonimidoyl]phenyl]methyl]-N-tetrahydropyran-4-yl-carbamate

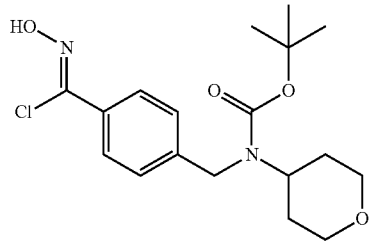

5 tert-Butyl N-[[4-hydroxyiminomethyl]phenyl]methyl]-N-tetrahydropyran-4-yl-carbamate (334.13 g, 999.2 mmol) was dissolved in isopropyl acetate (3.0 L) (the mixture was warmed to 40° C. to allow all the solids to go into solution). N-chlorosuccinimide (140.1 g, 1.049 mol) was added portionwise over 5 min and the reaction mixture was heated to 55° C. (external block temperature). After 45 min at 55° C. The reaction had gone to completion. The reaction mixture was cooled down to RT. The solids were filtered off and rinsed with Isopropyl acetate (1 L). Combined organic extract was sequentially washed with water (1.5 L, 5 times) and brine, dried over MgSO₄, filtered and concentrated in vacuo to give a viscous yellow oil (355.9 g, 96% Yiled). $^1$H NMR (400.0 MHz, CDCl₃) δ 1.40 (s, 9H), 1.47-1.67 (m, 5H), 3.44 (br s, 2H), 3.98 (dd, 2H), 4.43 br s, 2H), 7.26 (d, 2H), 7.88 (d, 2H) and 8.97 (s, 1H) ppm.

Step 5: tert-Butyl N-[[4-[5-[3-[bis(tert-butoxycarbonyl)amino]-6-bromo-pyrazin-2-yl]isoxazol-3-yl]phenyl]methyl]-N-tetrahydropyran-4-yl-carbamate

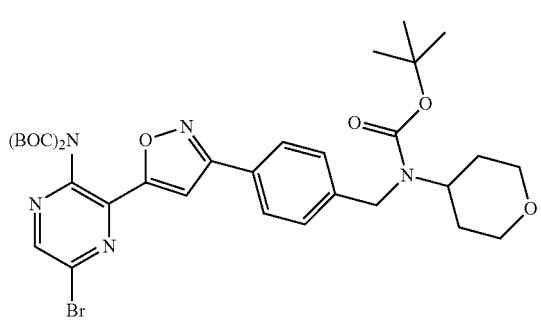

6

Et₃N (76.97 g, 106.0 mL, 760.6 mmol) was added over 20 minutes to a solution of tert-butyl N-(5-bromo-3-ethynylpyrazin-2-yl)-N-tert-butoxycarbonyl-carbamate (233.0 g, 585.1 mmol) and tert-butyl N-[[4-[chloro-N-hydroxy-carbonimidoyl]phenyl]methyl]-N-tetrahydropyran-4-yl-carbamate (269.8 g, 731.4 mmol) in DCM (2.330 L) at RT. During addition of triethylamine, the exotherm was stabilised by cooling the mixture in an ice bath, then the reaction mixture was gradually warmed up to RT and the mixture was stirred at RT overnight. The reaction mixture was sequentially washed with water (1.5 L, 3 times) and brine. The organic extract was dried over MgSO$_4$, filtered and partially concentrated in vacuo. Heptane (1.5 L) was added and the concentration was continued yielding 547.63 g of a yellow-orange solid. 542.12 g was taken up into ~2 vol (1 L) of ethyl acetate. The mixture was heated to 74-75° C. internally and stirred until all the solid went into solution. Heptane (3.2 L) was added slowly via addition funnel to the hot solution keeping the internal temperature between 71° C. and 72° C. At the end of the addition, the dark brown solution was seeded with some recrystallised product, and the reaction mixture was allowed to cool down to RT without any stirring to crystallise O/N. The solid was filtered off and rinsed with heptane (2×250 mL), then dried in vacuo to give the title product (307.38 g 72% Yield). $^1$H NMR (400.0 MHz, DMSO) δ 1.30 (s, 27H), 1.40-1.55 (m, 4H), 1.63-1.75 (m, 2H), 3.26-3.35 (m, 1H), 3.80-3.88 (m, 2H), 4.40-4.50 (m, 2H), 7.40 (d, 2H), 7.85 (s, 1H), 7.98 (d, 2H) and 9.04 (s, 1H).

Step 6: 1-Bromo-4-[1,2,2,2-tetradeuterio-1-(trideuteriomethyl)ethyl]sulfanyl-benzene

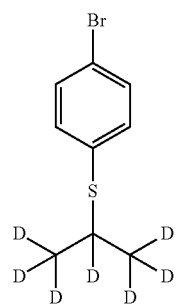

8

Sodium hydride (246.5 mg, 6.163 mmol) was added portionwise to a stirred solution of 4-bromobenzenethiol 7 (970.9 mg, 5.135 mmol) in DMF (10 mL) at 0° C. After stirring at this temperature for 15 minutes 1,1,1,2,3,3,3-heptadeuterio-2-iodo-propane (1 g, 5.649 mmol) was added and the reaction allowed to warm to ambient temperature over 18 hours. The reaction was quenched by the addition of water and the mixture stirred for 10 minutes. The mixture was extracted with diethyl ether (×3) and the combined organic extracts washed with water (×2), brine (×2), dried (MgSO$_4$), filtered and concentrated in vacuo to give the sub-title compound that was used directly without further purification assuming 100% Yield and purity; $^1$H NMR (500 MHz, DMSO) δ 7.48-7.55 (m, 2H) and 7.25-7.37 (m, 2H) ppm.

Step 7: 1-Bromo-4-[1,2,2,2-tetradeuterio-1-(trideuteriomethyl)ethyl]sulfonyl-benzene

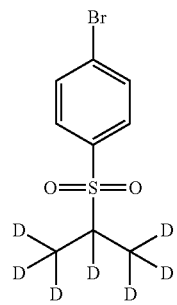

9 mCPBA (2.875 g, 12.83 mmol) was added in portions to a stirred solution of 1-bromo-4-[1,2,2,2-tetradeuterio-1-(trideuteriomethyl)ethyl]sulfanyl-benzene (1.223 g, 5.134 mmol) in DCM (20 mL) at 0° C. and the reaction allowed to warm to ambient temperature over 17 hours. The mixture was washed 1M aqueous NaOH (×2), saturated aqueous Na$_2$S$_2$O$_3$ (×3), brine (×1), dried (MgSO$_4$), filtered and concentrated in vacuo. The residue was purified by column chromatography (ISCO Companion, 80 g column, eluting with 0 to 40% EtOAc/Petroleum Ether, loaded in DCM) to give the sub-title compound as a colourless oil (1.19 g, 86% Yield); $^1$H NMR (500 MHz, DMSO) δ 7.77-7.81 (m, 2H) and 7.88-7.92 (m, 2H) ppm.

Step 8: 4,4,5,5-Tetramethyl-2-[4-[1,2,2,2-tetradeuterio-1-(trideuteriomethyl)ethyl]sulfonylphenyl]-1,3,2-dioxaborolane

10

Pd(dppf)Cl$_2$.DCM (179.8 mg, 0.2202 mmol) was added to a stirred suspension of 1-bromo-4-[1,2,2,2-tetradeuterio-1-(trideuteriomethyl)ethyl]sulfonyl-benzene (1.19 g, 4.404 mmol), bis(dipinacolato)diboron (1.342 g, 5.285 mmol) and KOAc (1.296 g, 13.21 mmol) in dioxane (10 mL). The reaction placed under an atmosphere of nitrogen via 5× nitrogen/vacuum cycles and the mixture was heated at 80° C. for 4.5 hours. The reaction was cooled to ambient temperature and the solvent removed in vacuo. The residue was partitioned between Et$_2$O and water and the layers separated. The organic layer was dried (MgSO$_4$), filtered and concentrated in vacuo. The residue was dissolved in 30% EtOAc/Petroleum ether (35 mL) and 1.2 g of Florosil was added. The mixture was stirred for 30 minutes then filtered, washing the solids with further aliquots of 30% EtOAc/Petrol (×3). The filtrate was concentrated in vacuo and triturated from 10% EtOAc/petroleum ether. The resultant solid was isolated by filtration, washed with petroleum ether and dried in vacuo to give the sub-title compound as an off-white solid (1052.1 mg, 75% Yield); $^1$H NMR (500 MHz, DMSO) δ 1.33 (s, 12H), 7.87 (d, J=8.4 Hz, 2H) and 7.94 (d, J=8.4 Hz, 2H) ppm.

Step 9: tert-Butyl N-[[4-[5-[3-[bis(tert-butoxycarbonyl)amino]-6-[4-[1,2,2,2-tetradeuterio-1-(trideuteriomethyl)ethyl]sulfonylphenyl]pyrazin-2-yl]isoxazol-3-yl]phenyl]methyl]-N-tetrahydropyran-4-yl-carbamate

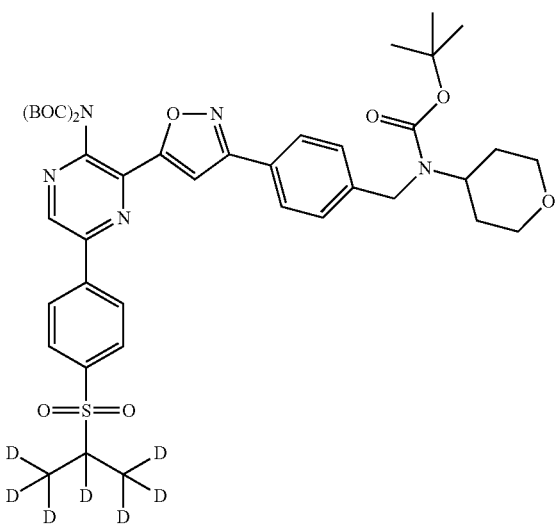

tert-Butyl N-[[4-[5-[3-[bis(tert-butoxycarbonyl)amino]-6-bromo-pyrazin-2-yl]isoxazol-3-yl]phenyl]methyl]-N-tetrahydropyran-4-yl-carbamate (200 mg, 0.2737 mmol) and 4,4,5,5-tetramethyl-2-[4-[1,2,2,2-tetradeuterio-1-(trideuteriomethyl)ethyl]sulfonylphenyl]-1,3,2-dioxaborolane (95.53 mg, 0.3011 mmol) were suspended in MeCN (2.000 mL)/water (2.000 mL) and Na$_2$CO$_3$ (273.7 µL of 2 M, 0.5474 mmol) was added. The reaction was degassed with 3× nitrogen/vacuum cycles. Pd(tBu$_3$P)$_2$ (13.99 mg, 0.02737 mmol) was added and the reaction again degassed 3 times then heated to 65° C. for 18 hours. The reaction was cooled to ambient temperature and diluted with EtOAc/water. The aqueous layer was extracted with EtOAc (×1) and the combined organic extracts dried (MgSO$_4$), filtered and concentrated in vacuo. The residue was purified by column chromatography (ISCO Companion, 40 g column, elueting with 0 to 25% EtOAc/Petroleum Ether, loaded in DCM) to give the sub-title product as an off-white solid (152.3 mg, 66% Yield); $^1$H NMR (500 MHz, DMSO) δ 1.31 (s, 18H) 1.31-1.45 (m, 9H), 1.52 (d, J=13.1 Hz, 2H), 1.70 (ddd, J=11.5, 10.8, 2.8 Hz, 2H), 3.27-3.30 (m, 3H), 3.85 (d, J=13.3 Hz, 2H), 4.47 (s, 2H), 7.44 (d, J=8.3 Hz, 2H), 7.99 (d, J=8.3 Hz, 2H), 8.02 (s, 1H), 8.08 (d, J=8.6 Hz, 2H), 8.65 (d, J=8.6 Hz, 2H) and 9.52 (s, 1H) ppm; MS (ES+) 741.1 (M-BOC).

Step 10: 5-[4-[1,2,2,2-Tetradeuterio-1-(trideuterioethyl)ethyl]sulfonylphenyl]-3-[3-[4-[(tetrahydropyran-4-ylamino)methyl]phenyl]isoxazol-5-yl]pyrazin-2-amine (compound II-2)

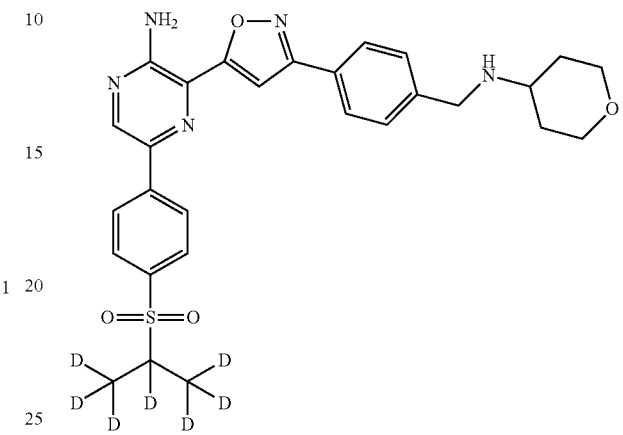

3M HCl in MeOH (1 mL of 3 M, 3.000 mmol) was added to a stirred solution of tert-butyl N—[[4-[5-[3-[bis(tert-butoxycarbonyl)amino]-6-[4-[1,2,2,2-tetradeuterio-1-(trideuteriomethyl)ethyl]sulfonylphenyl]pyrazin-2-yl]isoxazol-3-yl]phenyl]methyl]-N-tetrahydropyran-4-yl-carbamate (152 mg, 0.1807 mmol) in DCM (5 mL) and the reaction heated at reflux for 16 hours. The reaction was cooled to ambient temperature and the resultant precipitate was isolated by filtration to give the di-HCl salt of the title compound as yellow solid (80.5 mg, 73% Yield); $^1$H NMR (500 MHz, DMSO) δ 1.66 (ddd, J=14.0, 10.1, 2.8 Hz, 2H), 2.06 (d, J=11.5 Hz, 2H), 3.34 (t, J=11.9 Hz, 2H), 3.62 (s, 1H), 3.96 (dd, J=10.9, 3.6 Hz, 2H), 4.26-4.33 (m, 2H), 7.23 (s, 2H), 7.75 (d, J=8.2 Hz, 2H), 7.85 (s, 1H), 7.95 (d, J=8.7 Hz, 2H), 8.13 (d, J=8.4 Hz, 2H), 8.39 (d, J=8.7 Hz, 2H), 8.97 (s, 1H) and 9.10 (s, 2H) ppm; MS (ES+) 541.3.

Synthesis of Intermediates

Scheme V: Synthesis of Intermediate A-4-ii

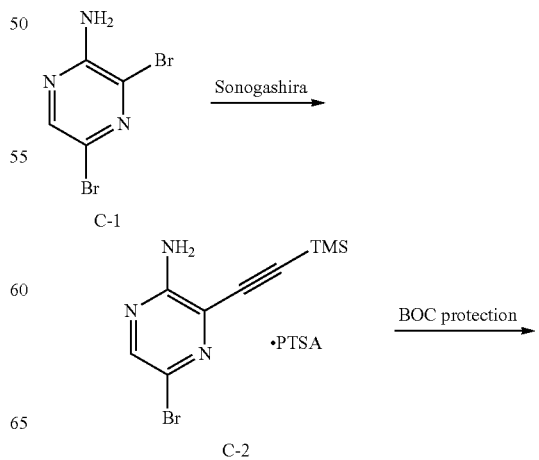

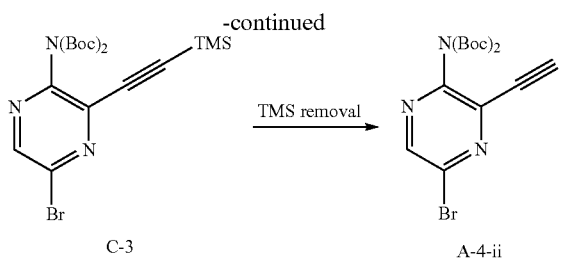

The compound of formula A-4-ii may be made according to the steps outlined in Scheme C. Sonogashira coupling reactions are known in the art (see e.g., Chem. Rev. 2007, 874-922). In some embodiments, suitable Sonogashira coupling conditions comprise adding 1 equivalent of the compound of formula C-1, 1 equivalent of TMS-acetylene, 0.010 equivalents of Pd(PPh$_3$)$_2$Cl$_2$, 0.015 equivalents of CuI and 1.20 equivalents of NMM in isopropanol. The product can be isolated by adding water to the alcoholic reaction mixture.

Amine salts of a product maybe formed by dissolving the amine in a common organic solvent and adding an acid. Examples of suitable solvents include chlorinated solvents (e.g., dichloromethane (DCM), dichloroethane (DCE), CH$_2$Cl$_2$, and chloroform), ethers (e.g., THF, 2-MeTHF and dioxane), esters (e.g., EtOAc, IPAC) and other aprotic solvents. Examples of suitable acids include but are not limited to HCl, H$_3$PO$_4$, H$_2$SO$_4$, MSA, and PTSA. In some embodiments, the solvent is IPAC and the acid is PTSA. In some embodiments, the acid addition salt is converted back to the free amine base in the presence of a suitable solvent and a suitable base. Suitable solvents include, but are not limited to, EtOAc, IPAC, dichloromethane (DCM), dichloroethane (DCE), CH$_2$Cl$_2$, and chloroform, 2-MeTHF] and suitable bases include but are not limited to NaOH, NaHCO$_3$, Na$_2$CO$_3$, KOH, KHCO$_3$, K$_2$CO$_3$, or Cs$_2$CO$_3$. In some embodiments, the suitable solvent is EtOAc and the suitable base is KHCO$_3$ The amine of Compound C-2 may be protected with various amine protecting groups, such as BOC (tert-butoxycarbonyl). Introduction of BOC protecting groups is known in the art (see e.g. Protecting Groups in Organic Synthesis, Greene and Wuts). In some embodiments, suitable conditions involve adding 1.00 equivalents of the amine, 2.10 equivalents of di-tert-butyl dicarbonate, and 0.03 equivalents of DMAP in EtOAc.

Reduction in Pd is achieved by treating with a metal scavenger (silica gel, functionalized resins, charcoal). In some embodiments, suitable conditions involve adding charcoal.

The TMS (trimethylsilyl) protecting group on Compound C-3 may be removed via conditions known to one of skill in the art. In some embodiments, TMS removal conditions comprise reacting the TMS-protected compound with a suitable base in a suitable solvent. Examples of suitable solvents include chlorinated solvents (e.g., dichloromethane (DCM), dichloroethane (DCE), CH$_2$Cl$_2$, and chloroform), ethers (e.g., THF, 2-MeTHF and dioxane), esters (e.g., EtOAc, IPAC), other aprotic solvents and alcohol solvents (e.g., MeOH, EtOH, iPrOH). Examples of suitable bases include but are not limited to (e.g., NaOH, KOH, K$_2$CO$_3$, Na$_2$CO$_3$). In certain embodiments, suitable conditions comprise adding 1.00 equivalents of the TMS-protected acetylene, 1.10 equivalents of K$_2$CO$_3$, EtOAc and EtOH. In some embodiments, the alcoholic solvent, such as EtOH, is added last in the reaction. In some embodiments the product acetylene is isolated by adding water.

Scheme VV: Example Synthesis of Compound A-4-ii

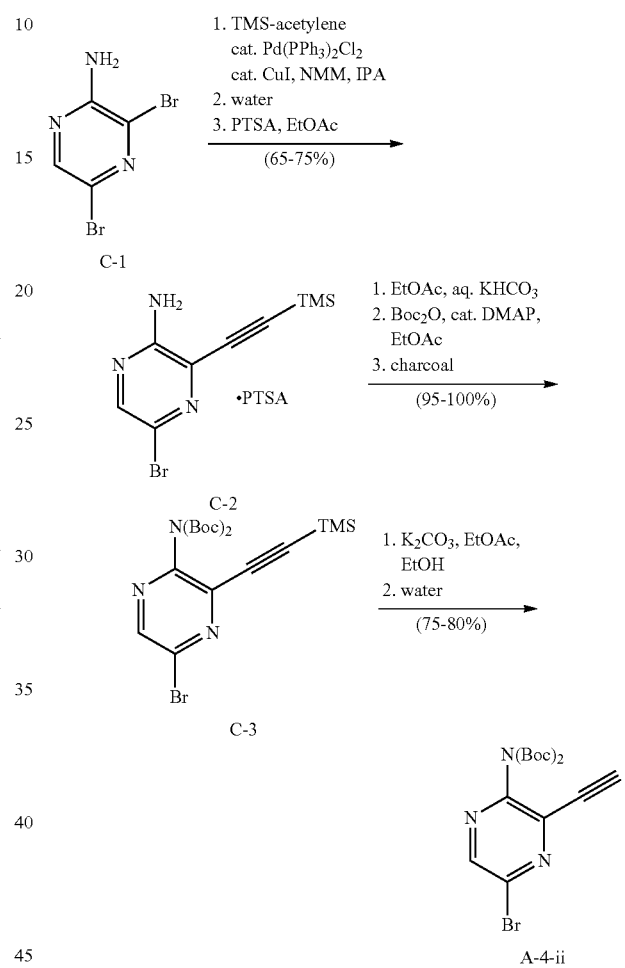

Example 4

Synthesis of Compound A-4-ii

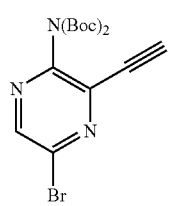

Step 1: Preparation of 5-bromo-3-((trimethylsilyl)ethynyl)pyrazin-2-amine (Compound C-2)

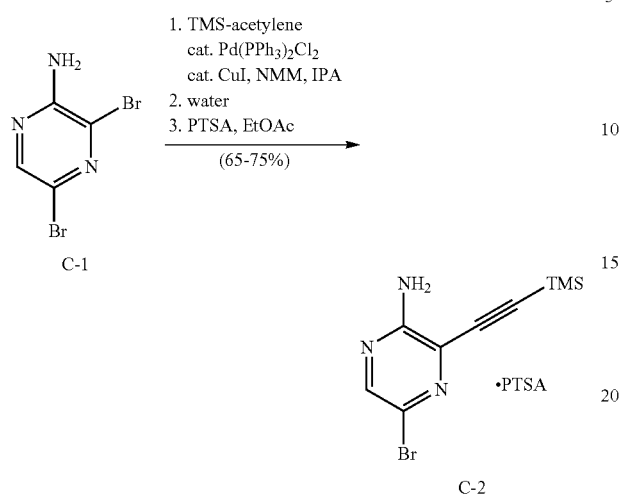

Charge isopropanol (8.0 L) to a reactor the stir and sparge with a stream of $N_2$. Add 3,5-dibromopyrazin-2-amine (Compound C-1) (2000 g, 7.91 moles), $Pd(PPh_3)_2Cl_2$ (56 g, 0.079 moles), CuI (23 g, 0.119 moles), and NMM (1043 mL, 9.49 moles) to the reactor under a $N_2$ atmosphere. Adjust the reaction temperature to 25° C. Purge the reactor with $N_2$ by doing at least three vacuum/$N_2$ purge cycles. Charge TMS-acetylene (1.12 L, 7.91 moles) to the reaction mixture and maintain the reaction temperature below 30° C. When the reaction is complete lower the temperature of the reaction mixture to 15° C. then add water (10 L) and stir for at least 2 h. The solid is collected by filtration washing the solid with 1:1 IPA/water (2×6 L). The filter cake is dried under vacuum then charged to a reactor and dissolved in EtOAc (12.5 L). PTSA hydrate (1.28 kg, 6.72 mol) is charged as a solid to the reactor. The mixture is stirred at ambient temperature for at least 5 h then the solid is collected by filtration, washed with 1:1 heptane/EtOAc (3.5 L) followed by heptane (3.5 L). The filter cake is dried to afford 5-bromo-3-((trimethylsilyl)ethynyl)pyrazin-2-amine (Compound C-2) as a PTSA salt (2356 g, 67% yield, 98.9 area % purity by HPLC). $^1$H NMR (400 MHz, DMSO) δ 8.12 (s, 1H), 7.48 (d, J=8.1 Hz, 2H), 7.12 (d, J=8.0 Hz, 2H), 2.29 (s, 3H), 0.26 (s, 9H).

Steps 2 and 3

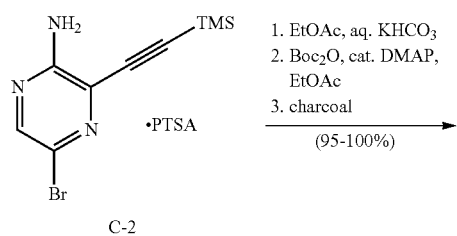

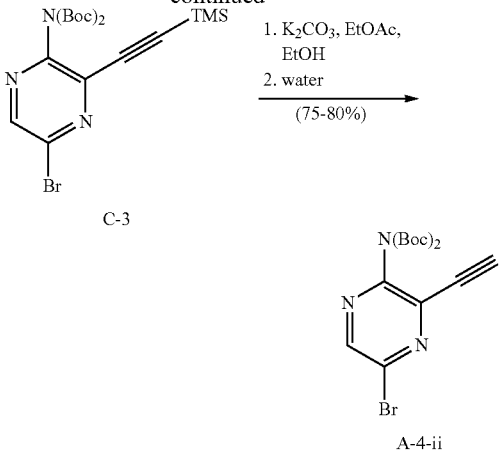

Step 2: Preparation of tert-butyl N-tert-butoxycarbonyl-N-[5-bromo-3-((trimethylsilybethynyl)pyrazin-2-yl]carbamate (Compound C-3)

A solution of 5-bromo-3-((trimethylsilyl)ethynyl)pyrazin-2-amine (Compound C-2) PTSA salt 3 (2350 g, 5.31 mol) in EtOAc (11.5 L) is stirred with a 20% w/w aq. solution of $KHCO_3$ (4.5 kg, 1.5 eq.) for at least 30 min. The layers are separated and the organic layer is concentrated then dissolved in EtOAc (7 L) and added to a reactor. DMAP (19.5 g, 0.16 mol) is added followed a solution of $Boc_2O$ (2436 g, 11.16 mol) in EtOAc (3 L) is added lowly. The reaction is stirred for at least 30 min to ensure complete reaction then activated charcoal (Darco G-60, 720 g) and Celite (720 g) are added and stirred for at least 2 h. The mixture is filtered washing the solid pad with EtOAc (2×1.8 L). The filtrate is concentrated to afford tert-butyl N-tert-butoxycarbonyl-N-[5-bromo-3-((trimethylsilyl)ethynyl)pyrazin-2-yl]carbamate (Compound C-3) that is used directly in the next step.

Step 3: Preparation of tert-butyl N-(5-bromo-3-ethynylpyrazin-2-yl)-N-tert-butoxycarbonylcarbamate (Compound A-4-ii)

$K_2CO_3$ (811 g, 5.87 mol) is charged to a reactor followed by a solution of Compound C-3 (2300 g, 4.89 mol) dissolved in EtOAc (4.6 L) agitation started. EtOH (9.2 L) is added slowly and the mixture stirred for at least 1 h to ensure that the reaction is complete then water (4.6 L) is added and stirred for at least 2 h. The solid is collected by filtration and washed with 1:1 EtOH/water (4.6 L followed by 2.3 L) followed by EtOH (2.3 L). The filter cake is dried to afford tert-butyl N-(5-bromo-3-ethynylpyrazin-2-yl)-N-tert-butoxycarbonylcarbamate (Compound A-4-ii) (1568 g, 78% yield, 97.5 area % by HPLC). $^1$H NMR (400 MHz, $CDCl_3$) δ 8.54 (s, 1H), 3.52 (s, 1H), 1.42 (s, 18H).

Solid Forms of Compound I-1

Compound I-1 has been prepared in various solid forms, including salts and hydrates. Applicants describe herein five novel solid forms of Compound I-1, provided in Table S-1 below:

TABLE S-1

| Example | Forms | Stoichiometry |
|---|---|---|
| Example 4 | Compound I-1 free base | N/A |
| Example 5 | Compound I-1•hydrochloric acid | 1:1 |
| Example 6 | Compound I-1 free base hydrate | — |
| Example 7 | Compound I-1•2-hydrochloric acid•1.5 H$_2$O | 1:2:1.5 |
| Example 8 | Compound I-1•hydrochloric acid hydrate | — |

Example 4

Compound I-1 (Free Base)

Compound I-1 free base can be formed according to the methods described in Example 1, Step 7 and Example 2, step 9.

XRPD of Compound I-1 (Free Base)

The XRPD pattern of Compound I-1 was recorded at room temperature in reflection mode using a Bruker D8 Advance diffractometer equipped with a sealed tube Cu source and a Vantec PSD detector (Bruker AXS, Madison, Wis., Asset V014333). The X-ray generator was operating at a voltage of 40 kV and a current of 40 mA. The powder sample was placed in a silicon holder. The data were recorded in a QL scanning mode over the range of 4°-45° 2 theta with a step size of 0.0140° and a dwell time of is per step. Fixed divergence slits of 0.2 mm were used. FIG. 1A shows the X-ray powder diffractogram of the sample which is characteristic of crystalline drug substance.

Representative XRPD peaks from Compound I-1:

| XRPD Peaks | Angle (2-Theta ± 0.2) | Intensity % |
|---|---|---|
| 1 | 5.4 | 56.2 |
| 2* | 11.6 | 27.2 |
| 3 | 13.4 | 19.8 |
| 4* | 14.3 | 83.9 |
| 5 | 14.9 | 41.1 |
| 6 | 15.9 | 54.2 |
| 7 | 16.3 | 21.4 |
| 8 | 16.9 | 28.1 |
| 9 | 17.7 | 17.2 |
| 10* | 18.4 | 20.9 |
| 11 | 20.4 | 14.4 |
| 12 | 20.9 | 100.0 |
| 13 | 21.3 | 38.8 |
| 14* | 22.4 | 52.7 |
| 15 | 23.0 | 27.6 |
| 16 | 24.0 | 21.2 |
| 17 | 24.6 | 25.4 |
| 18 | 25.3 | 29.0 |
| 19 | 25.8 | 11.1 |
| 20 | 26.6 | 48.9 |
| 21 | 27.4 | 65.2 |
| 22* | 27.9 | 34.6 |
| 23 | 29.0 | 19.9 |
| 24 | 31.7 | 11.8 |
| 25 | 34.2 | 12.4 |
| 26 | 36.3 | 10.3 |
| 27 | 37.1 | 16.3 |
| 28 | 38.7 | 12.0 |

Thermo Analysis of Compound I-1 Free Base

A thermal gravimetric analysis of Compound I-1 free base can be performed to determine the percent weight loss as a function of time using the TA Instrument TGA Q5000 (Asset V014258). A sample (8.040 mg) is added to a pre-tared aluminum pan and heated from ambient temperature to 350° C. at 10° C./min. The TGA result seen in FIG. 2A shows very little observed weight loss prior to melting or thermal degradation. From ambient temperature to 250° C., the weight loss is 0.4368%.

Differential Scanning Calorimetry of Compound I-1 Free Base

Differential scanning calorimetry of Compound I-1 free base can be measured using the TA Instrument DSC Q200 (Asset V005642). A sample (4.000 mg) is weighed in a pre-punched pinhole aluminum hermetic pan and heated from ambient temperature to 350° C. at 10° C./min. The DSC result seen in FIG. 3A shows there are two endothermic peaks observed, one at 184° C. (onset temperature of 180° C., enthalpy 28 J/g) and another at 219° C. (onset temperature of 218° C., enthalpy 82 J/g).

Crystal Structure of Compound I-1 Free Base

Compound I-1 free base (40 mg) is weighed into a scintillation vial. DCM (2.5 mL) is added and the system was vortexed for 30 seconds. The resulting solution is filtered with a 0.45 um PTFE syringe-tip filter. n-Heptane (100 uL) is then added to the solution. The solution is left to evaporate in a solvent cabinet for eight days.

A blade-shaped crystal was mounted on a MicroMount and centered on a Bruker APEX II CCD diffractometer with Cu Kα radiation at room temperature.

The crystal shows triclinic cell with P-1 space group. The lattice parameters are a=6.7319(2) Å, b=12.3762(3) Å, c=17.2422(4) Å, α=77.438(1)°, β=88.865(1)°, γ=81.271(1)° cell volume=1385.78(6) Å$^3$. There is one fully ordered molecule in the asymmetric unit. Two neighboring molecules are paired by H-bonds to give a R 2,2 (8) graph set. Such pairs stack with a distance of 3.4 Å.

Example 5

Compound I-1•Hydrochloric Acid

The mono-HCl salt of Compound I-1 can be formed by suspending Compound I-1 free base (Water (0.5)) (20.0 g, 36.86 mmol) in acetone (160.0 mL) and water (20.0 mL). HCl (20.28 mL of 2.0 M, 40.55 mmol) is added and the reaction is allowed to stir at 30° C. overnight. The solid is collected by filtration and the filter-cake washed with acetone/water (4/1, 50 mL) (2×) and then acetone (50 mL). The solid is then air-dried and vacuum-dried (20 torr/N$_2$ bleed/55° C.) to afford 19.13 g (91%) of Compound I-1•hydrochloric acid as a fine, yellow powder.

XRPD of Compound I-1•Hydrochloric Acid

The XRPD pattern of Compound I-1•hydrochloric acid was recorded at room temperature in reflection mode using a Bruker D8 Advance diffractometer equipped with a sealed tube Cu source and a Vantec PSD detector (Bruker AXS, Madison, Wis., Asset V014333). The X-ray generator was operating at a voltage of 40 kV and a current of 40 mA. The powder sample was placed in a silicon holder. The data were recorded in a QL scanning mode over the range of 4°-45° 2 theta with a step size of 0.0140° and a dwell time of is per step. Fixed divergence slits of 0.2 mm were used. FIG. 1B shows the X-ray powder diffractogram of the sample which is characteristic of crystalline drug substance. Representative XRPD peaks from Compound I-1•hydrochloric acid:

| XRPD Peaks | Angle (2-Theta ± 0.2) | Intensity % |
| --- | --- | --- |
| 1 | 4.3 | 13.5 |
| 2 | 10.7 | 13.1 |
| 3* | 12.9 | 19.0 |
| 4 | 14.8 | 12.3 |
| 5* | 15.3 | 36.1 |
| 6* | 15.6 | 34.2 |
| 7 | 17.2 | 26.9 |
| 8 | 17.5 | 45.0 |
| 9* | 18.2 | 32.3 |
| 10 | 18.9 | 34.7 |
| 11 | 20.1 | 10.6 |
| 12 | 20.5 | 28.4 |
| 13 | 20.9 | 55.9 |
| 14 | 21.3 | 22.8 |
| 15 | 21.9 | 12.3 |
| 16 | 22.6 | 15.8 |
| 17* | 23.3 | 23.7 |
| 18 | 24.0 | 17.7 |
| 19 | 24.5 | 29.7 |
| 20 | 25.4 | 21.2 |
| 21 | 26.0 | 40.0 |
| 22 | 26.6 | 14.5 |
| 23 | 27.0 | 29.2 |
| 24 | 27.5 | 100.0 |
| 25 | 29.9 | 20.0 |
| 26 | 30.3 | 13.1 |
| 27 | 32.2 | 11.8 |
| 28 | 33.6 | 14.7 |
| 29 | 35.2 | 18.2 |
| 30 | 36.2 | 12.4 |
| 31 | 37.3 | 14.1 |
| 32 | 39.0 | 10.9 |
| 33 | 39.5 | 11.7 |

Thermo Analysis of Compound I-1•Hydrochloric Acid

A thermal gravimetric analysis of Compound I-1•hydrochloric acid is performed to determine the percent weight loss as a function of time using the TA Instrument TGA Q5000 (Asset V014258). A sample (9.517 mg) is added to a pre-tared aluminum pan and heated from ambient temperature to 350° C. at 10° C./min. The TGA result seen in FIG. 2B shows very little observed weight loss prior to melting or thermal degradation. From ambient temperature to 250° C., the weight loss was 0.7311%.

Differential Scanning Calorimetry of Compound I-1•Hydrochloric Acid

Differential scanning calorimetry of Compound I-1•hydrochloric acid was measured using the TA Instrument DSC Q200 (Asset V005642). A sample (3.920 mg) was weighed in a pre-punched pinhole aluminum hermetic pan and heated from ambient temperature to 350° C. at 10° C./min. The DSC result seen in FIG. 3B shows a single endothermic peak at 313° C. (onset temperature of 302° C.) immediately prior to degradation.

Example 6

Compound I-1 Free Base Hydrate

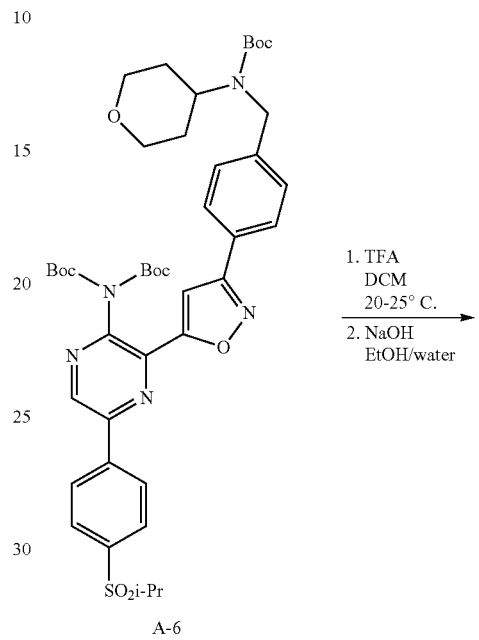

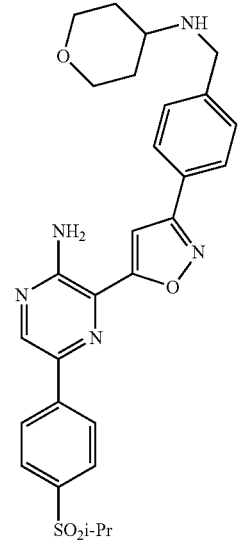

A suspension of Compound A-6 (10.0 g, 11.99 mmol) is stirred at ambient temperature (20° C. in DCM (10.0 mL) is). TFA (27.34 g, 18.47 mL, 239.8 mmol) is added over 2 minutes and the suspension becomes a solution. Heated the solution at 80° C. with a slow $N_2$ stream to remove remaining DCM. The reaction mixture is diluted with water (100.0 mL) over 2 minutes and becomes a suspension after a few minutes. NaOH (149.9 mL of 2.0 M, 299.8 mmol) is added dropwise over 1 hour and the reaction is allowed to cool to ambient temperature and stirred overnight. The solids are collected by filtration, and the filter-cake is washed with water (20.00 mL)

(2×) then with EtOH (20.00 mL) (2×), then air-dried and vacuum-dried (50° C./20 torr) to afford 6.03 g (94%) of Compound I-1 hydrate a fine, yellow powder.

XRPD of Compound I-1 Free Base Hydrate

The XRPD pattern of Compound I-1 hydrate was acquired at room temperature in reflection mode using a Bruker D8 Discover diffractometer equipped with a sealed tube source and a Hi-Star area detector (Bruker AXS, Madison, Wis., Asset V012842). The X-Ray generator was operating at a voltage of 40 kV and a current of 35 mA. The powder sample was placed in a nickel holder. Two frames were registered with an exposure time of 120 s each. The data frames were subsequently integrated over the range of 4.5°-22.4° and 21°-39.0° 2theta with a step size of 0.02° merged into one continuous pattern. FIG. 1C shows the X-ray powder diffractogram of the sample which is characteristic of crystalline drug substance.

Representative XRPD peaks from Compound I-1 free base hydrate

| XRPD Peaks | Angle (2-Theta ± 0.2) | Intensity % |
|---|---|---|
| 1 | 5.6 | 59.9 |
| 2* | 8.1 | 72.6 |
| 3* | 9.4 | 42.4 |
| 4 | 13.8 | 47.3 |
| 5* | 14.6 | 100.0 |
| 6 | 15.8 | 45.2 |
| 7 | 17.3 | 56.4 |
| 8 | 17.9 | 52.2 |
| 9* | 19.2 | 97.8 |
| 10* | 19.7 | 51.6 |
| 11 | 20.0 | 77.3 |
| 12 | 20.8 | 41.8 |
| 13 | 25.0 | 29.1 |
| 14 | 26.9 | 53.0 |
| 15 | 28.0 | 31.8 |
| 16 | 29.9 | 23.1 |

Thermo Gravimetric Analysis of Compound I-1 Free Base Hydrate

A thermal gravimetric analysis of Compound I-1 hydrate is performed to determine the percent weight loss as a function of time using the TA Instrument TGA Q5000 (Asset V014258). A sample (5.667 mg) is added to a pre-tared aluminum pan and heated from ambient temperature to 375° C. at 5° C./min. The TGA result seen in FIG. 2C shows an early weight loss of 0.95%.

Differential Scanning Calorimetry of Compound I-1 Free Base Hydrate

Differential scanning calorimetry of Compound I-1 hydrate is measured using the TA Instrument DSC Q200 (Asset V005642). A sample (2.500 mg) is weighed in a pre-punched pinhole aluminum hermetic pan and heated from 5° C. to 350° C. at 3° C./min, modulated ±1° C. every 60 seconds. The DSC result seen in FIG. 3C shows there are two endothermic peaks observed, one at 203° C. (onset temperature of 198° C., enthalpy 23 J/g) and another at 217° C. (onset temperature of 213° C., enthalpy 82 J/g).

Example 7

Compound I-1•2-hydrochloric acid•1.5H$_2$O

Compound I-1•2-hydrochloric acid•1.5H$_2$O can be made by dissolving Compound I-1 free base (23.58 g, 44.19 mmol) in DCM (825.3 mL) and MeOH (82.53 mL). The mixture is cooled down to 0° C. and HCl in MeOH (58.93 mL of 3 M, 176.8 mmol) is added over 2 minutes. The reaction mixture is warmed up to room temperature overnight. The mixture is filtered and washed with DCM then dried overnight under high vacuum (0.77 mbar; Edward pump) at ~60° C. to give 24.79 g of a yellow solid.

XRPD of Compound I-1•2-hydrochloric acid•1.5H$_2$O

The XRPD pattern of Compound I-1•2-hydrochloric acid was acquired at room temperature in reflection mode using a Bruker D8 Discover diffractometer equipped with a sealed tube source and a Hi-Star area detector (Bruker AXS, Madison, Wis., Asset V012842). The X-Ray generator was operating at a voltage of 40 kV and a current of 35 mA. The powder sample was placed in a nickel holder. Two frames were registered with an exposure time of 120 s each. The data frames were subsequently integrated over the range of 4.5°-22.4° and 21°-39.0° 2theta with a step size of 0.02° merged into one continuous pattern. FIG. 1D shows the X-ray powder diffractogram of the sample which is characteristic of crystalline drug substance.

Representative XRPD Peaks from Compound I-1•2-hydrochloric acid•1.5H$_2$O

| XRPD Peaks | Angle (2-Theta ± 0.2) | Intensity % |
|---|---|---|
| 1 | 5.6 | 100.0 |
| 2* | 7.0 | 37.9 |
| 3* | 12.6 | 31.1 |
| 4 | 13.1 | 27.0 |
| 5* | 14.0 | 40.3 |
| 6 | 15.0 | 45.0 |
| 7* | 16.9 | 43.9 |
| 8 | 17.8 | 37.4 |
| 9 | 18.8 | 27.6 |
| 10 | 22.7 | 34.6 |
| 11 | 25.2 | 35.9 |
| 12* | 26.1 | 25.2 |
| 13 | 26.9 | 33.2 |
| 14 | 31.6 | 20.4 |

Thermo Gravimetric Analysis of Compound I-1•2-hydrochloric acid•1.5H$_2$O

A thermal gravimetric analysis of Compound I-1•2-hydrochloric acid•1.5H$_2$O is performed to determine the percent weight loss as a function of time using the TA Instrument TGA Q500 (Asset SD001280). A sample (4.836 mg) is added to a pre-tared aluminum pan and heated from ambient temperature to 300° C. at 10° C./min. The TGA shows a weight loss of 4.2% up to 100° C. followed by an additional weight loss of 5.1% up to 225° C. The material has a degradation onset temperature of 293° C.

Differential Scanning Calorimetry of Compound I-1•2-hydrochloric acid•1.5H$_2$O

Differential scanning calorimetry of Compound I-1•2-hydrochloric acid•1.5H$_2$O is measured using the TA Instrument DSC Q2000 (Asset SD001279). A sample (4.033 mg) is weighed in a pre-punched pinhole aluminum hermetic pan and heated from 25° C. to 285° C. at 10° C./min. The DSC result shows three broad endothermic melting events at 215° C. (onset temperature of 195° C.), 247° C. (onset temperature of 246° C.), and 273° C. (onset temperature of 267° C.).

CHN Elemental Analysis of Compound I-1•2-hydrochloric acid•1.5H$_2$O

CHN elemental analysis of Compound I-1•2-hydrochloric acid•1.5H$_2$O was done at Medac LTD, UK. CHN results suggest a di-HCl 1.5 hydrate.

|  | Element | | | | |
|---|---|---|---|---|---|
|  | C | H | N | S | Cl |
| % Theory | 53.08 | 5.73 | 11.05 | 5.06 | 11.19 |
| % Found 1 | 53.36 | 5.44 | 11.08 | 4.96 | 10.93 |
| % Found 2 | 53.37 | 5.37 | 11.13 | 5.04 | 10.89 |

Example 8

Compound I-1•Hydrochloric Acid Hydrate

Compound I-1•hydrochloric acid hydrate can be made by Compound I-1 free base (300 mg) in acetonitrile (3.0 mL) for 2 to 5 minutes. 1N aqueous HCl solution (562.2 uL) is then added and the suspension is stirred at room temperature for 72 hours. The suspension is then centrifuged and the residual solids isolated and dried overnight in a room temperature vacuum oven.

XRPD of Compound I-1•Hydrochloric Acid Hydrate

The XRPD pattern of Compound I-1•hydrochloric acid hydrate was acquired at room temperature in reflection mode using a Bruker D8 Discover diffractometer equipped with a sealed tube source and a Hi-Star area detector (Bruker AXS, Madison, Wis., Asset V012842). The X-Ray generator was operating at a voltage of 40 kV and a current of 35 mA. The powder sample was placed in a nickel holder. Two frames were registered with an exposure time of 120 s each. The data frames were subsequently integrated over the range of 4.5°-22.4° and 21°-39.0° 2theta with a step size of 0.02° merged into one continuous pattern. FIG. 1E shows the X-ray powder diffractogram of the sample which is characteristic of crystalline drug substance.

Representative XRPD Peaks from Compound I-1•Hydrochloric Acid•Hydrate

| XRPD Peaks | Angle (2-Theta ± 0.2) | Intensity % |
|---|---|---|
| 1 | 4.7 | 34.4 |
| 2* | 7.7 | 79.8 |
| 3 | 11.8 | 26.2 |
| 4 | 14.0 | 100.0 |
| 5 | 14.8 | 59.9 |
| 6 | 15.2 | 32.2 |
| 7* | 16.2 | 49.1 |
| 8 | 16.6 | 26.1 |
| 9 | 17.2 | 29.8 |
| 10 | 17.9 | 39.9 |
| 11 | 18.7 | 50.3 |
| 12* | 19.0 | 28.9 |
| 13* | 19.8 | 61.3 |
| 14 | 20.5 | 25.3 |
| 15 | 21.8 | 19.7 |
| 16 | 22.7 | 35.1 |
| 17* | 23.4 | 39.4 |
| 18 | 23.7 | 28.9 |
| 19 | 24.5 | 26.5 |
| 20 | 25.7 | 23.2 |
| 21 | 26.8 | 50.8 |
| 22 | 27.6 | 31.5 |
| 23 | 29.0 | 22.0 |
| 24 | 29.9 | 24.0 |
| 25 | 30.4 | 20.1 |
| 26 | 32.0 | 17.0 |
| 27 | 32.6 | 22.4 |
| 28 | 33.3 | 16.0 |
| 29 | 33.8 | 14.7 |
| 30 | 36.1 | 16.0 |

Thermo Gravimetric Analysis of Compound I-1•Hydrochloric Acid Hydrate

A thermal gravimetric analysis of Compound I-1•hydrochloric acid hydrate is performed to determine the percent weight loss as a function of time using the TA Instrument TGA Q500 (Asset V014840). A sample (3.648 mg) is added to a pre-tared aluminum pan and heated from ambient temperature to 300° C. at 10° C./min. FIG. 2E shows the TGA result with a weight loss of 7.5% occurring upon heating to 100° C., which corresponds to ~2.3 molar equivalents of water.

Differential scanning calorimetry of Compound I-1•hydrochloric acid hydrate is measured using the TA Instrument DSC Q200 (Asset V005642). A sample (3.340 mg) is weighed in a pre-punched pinhole aluminum hermetic pan and heated from 20° C. to 250° C. at 2° C./min, modulated ±1° C. every 60 seconds. FIG. 3E shows the DSC result with a broad endothermic peak at 58° C. that corresponds to the water weight loss observed in the TGA. There is also an exothermic peak at 192-196° C.

Example 9

Cellular ATR Inhibition Assay

Compounds can be screened for their ability to inhibit intracellular ATR using an immunofluorescence microscopy assay to detect phosphorylation of the ATR substrate histone H2AX in hydroxyurea treated cells. HT29 cells are plated at 14,000 cells per well in 96-well black imaging plates (BD 353219) in McCoy's 5A media (Sigma M8403) supplemented with 10% foetal bovine serum (JRH Biosciences 12003), Penicillin/Streptomycin solution diluted 1:100 (Sigma P7539), and 2 mM L-glumtamine (Sigma G7513), and allowed to adhere overnight at 37° C. in 5% $CO_2$. Compounds are then added to the cell media from a final concentration of 25 µM in 3-fold serial dilutions and the cells are incubated at 37° C. in 5% $CO_2$. After 15 min, hydroxyurea (Sigma H8627) is added to a final concentration of 2 mM.

After 45 min of treatment with hydroxyurea, the cells are washed in PBS, fixed for 10 min in 4% formaldehyde diluted in PBS (Polysciences Inc 18814), washed in 0.2% Tween-20 in PBS (wash buffer), and permeabilised for 10 min in 0.5% Triton X-100 in PBS, all at room temperature. The cells are then washed once in wash buffer and blocked for 30 min at room temperature in 10% goat serum (Sigma G9023) diluted in wash buffer (block buffer). To detect H2AX phosphorylation levels, the cells are then incubated for 1 h at room temperature in primary antibody (mouse monoclonal anti-phosphorylated histone H2AX Ser139 antibody; Upstate 05-636) diluted 1:250 in block buffer. The cells are then washed five times in wash buffer before incubation for 1 h at room temperature in the dark in a mixture of secondary antibody (goat anti-mouse Alexa Fluor 488 conjugated antibody; Invitrogen A11029) and Hoechst stain (Invitrogen H3570); diluted 1:500 and 1:5000, respectively, in wash buffer. The cells are then washed five times in wash buffer and finally 100 ul PBS is added to each well before imaging.

Cells are imaged for Alexa Fluor 488 and Hoechst intensity using the BD Pathway 855 Bioimager and Attovision software (BD Biosciences, Version 1.6/855) to quantify phosphorylated H2AX Ser139 and DNA staining, respectively. The percentage of phosphorylated H2AX-positive nuclei in a montage of 9 images at 20× magnification is then calculated for each well using BD Image Data Explorer software (BD Biosciences Version 2.2.15). Phosphorylated H2AX-positive nuclei are defined as Hoechst-positive regions of interest containing Alexa Fluor 488 intensity at 1.75-fold the average Alexa Fluor 488 intensity in cells not treated with hydroxyurea. The percentage of H2AX positive nuclei is finally plotted against concentration for each compound and IC50s for intracellular ATR inhibition are determined using Prism software (GraphPad Prism version 3.0cx for Macintosh, GraphPad Software, San Diego Calif., USA).

The compounds described herein can also be tested according to other methods known in the art (see Sarkaria et al, "Inhibition of ATM and ATR Kinase Activities by the Radiosensitizing Agent, Caffeine: *Cancer Research* 59: 4375-5382 (1999); Hickson et al, "Identification and Characterization of a Novel and Specific Inhibitor of the Ataxia-Telangiectasia Mutated Kinase ATM" *Cancer Research* 64: 9152-9159 (2004); Kim et al, "Substrate Specificities and Identification of Putative Substrates of ATM Kinase Family Members" *The Journal of Biological Chemistry*, 274(53): 37538-37543 (1999); and Chiang et al, "Determination of the catalytic activities of mTOR and other members of the phosphoinositide-3-kinase-related kinase family" *Methods Mol. Biol.* 281:125-41 (2004)).

Example 10

ATR Inhibition Assay

Compounds can be screened for their ability to inhibit ATR kinase using a radioactive-phosphate incorporation assay. Assays are carried out in a mixture of 50 mM Tris/HCl (pH 7.5), 10 mM $MgCl_2$ and 1 mM DTT. Final substrate concentrations are 10 µM [γ-33P]ATP (3 mCi $^{33}$P ATP/mmol ATP, Perkin Elmer) and 800 µM target peptide (ASELPASQPQPFSAKKK (SEQUENCE ID NO: 1)).

Assays are carried out at 25° C. in the presence of 5 nM full-length ATR. An assay stock buffer solution is prepared containing all of the reagents listed above, with the exception of ATP and the test compound of interest. 13.5 µL of the stock solution is placed in a 96 well plate followed by addition of 2 µL of DMSO stock containing serial dilutions of the test compound (typically starting from a final concentration of 15 µM with 3-fold serial dilutions) in duplicate (final DMSO concentration 7%). The plate is pre-incubated for 10 minutes at 25° C. and the reaction initiated by addition of 15 µL [γ-33P]ATP (final concentration 10 µM).

The reaction is stopped after 24 hours by the addition of 30 µL 0.1M phosphoric acid containing 2 mM ATP. A multiscreen phosphocellulose filter 96-well plate (Millipore, Cat no. MAPHN0B50) is pretreated with 100 µL 0.2M phosphoric acid prior to the addition of 45 µL of the stopped assay mixture. The plate is washed with 5×200 µL 0.2M phosphoric acid. After drying, 100 µL Optiphase 'SuperMix' liquid scintillation cocktail (Perkin Elmer) is added to the well prior to scintillation counting (1450 Microbeta Liquid Scintillation Counter, Wallac).

After removing mean background values for all of the data points, Ki(app) data are calculated from non-linear regression analysis of the initial rate data using the Prism software package (GraphPad Prism version 3.0cx for Macintosh, GraphPad Software, San Diego Calif., USA).

Example 11

Cisplatin Sensitization Assay

Compounds can be screened for their ability to sensitize HCT116 colorectal cancer cells to Cisplatin using a 96 h cell viability (MTS) assay. HCT116 cells, which possess a defect in ATM signaling to Cisplatin (see, Kim et al.; *Oncogene* 21:3864 (2002); see also, Takemura et al.; *JBC* 281:30814 (2006)) are plated at 470 cells per well in 96-well polystyrene plates (Costar 3596) in 150 µl of McCoy's 5A media (Sigma M8403) supplemented with 10% foetal bovine serum (JRH Biosciences 12003), Penicillin/Streptomycin solution diluted 1:100 (Sigma P7539), and 2 mM L-glumtamine (Sigma G7513), and allowed to adhere overnight at 37° C. in 5% $CO_2$. Compounds and Cisplatin are then both added simultaneously to the cell media in 2-fold serial dilutions from a top final concentration of 10 µM as a full matrix of concentrations in a final cell volume of 200 µl, and the cells are then incubated at 37° C. in 5% $CO_2$. After 96 h, 40 µl of MTS reagent (Promega G358a) is added to each well and the cells are incubated for 1 h at 37° C. in 5% $CO_2$. Finally, absorbance is measured at 490 nm using a SpectraMax Plus 384 reader (Molecular Devices) and the concentration of compound required to reduce the IC50 of Cisplatin alone by at least 3-fold (to 1 decimal place) can be reported.

Example 12

Single Agent HCT116 Activity

Compounds can be screened for single agent activity against HCT116 colorectal cancer cells using a 96 h cell viability (MTS) assay. HCT116 are plated at 470 cells per well in 96-well polystyrene plates (Costar 3596) in 150 µl of McCoy's 5A media (Sigma M8403) supplemented with 10% foetal bovine serum (JRH Biosciences 12003), Penicillin/Streptomycin solution diluted 1:100 (Sigma P7539), and 2 mM L-glumtamine (Sigma G7513), and allowed to adhere overnight at 37° C. in 5% $CO_2$. Compounds are then added to the cell media in 2-fold serial dilutions from a top final concentration of 10 µM as a full matrix of concentrations in a final cell volume of 200 µl, and the cells are then incubated at 37° C. in 5% $CO_2$. After 96 h, 40 µl of MTS reagent (Promega G358a) is added to each well and the cells are incubated for 1 h at 37° C. in 5% $CO_2$. Finally, absorbance is measured at 490 nm using a SpectraMax Plus 384 reader (Molecular Devices) and $IC_{50}$ values can be calculated.

Example 13

Pharmacokinetics

Noncompartmental pharmacokinetic parameters can be analyzed using Watson Bioanalytical LIMS (Version 7.4; Thermo Fisher Scientific) from either the blood or plasma samples. The following parameters are estimated following intravenous (IV) dosing; terminal elimination half-life ($T_{1/2}$=ln(2)/λz, where λz is the first order rate constant associated with the terminal (log-linear) portion of the curve. The area under the curve ($AUC_{last}$=area under the curve from the time of dosing to the last measurable concentration). The area under the curve extrapolated to infinity ($AUC_{0-\infty}$=$AUC_{last}$+$C_{last}$/λz). The clearance (Cl; Cl=$Dose_{IV}$/$AUC_{0-\infty}$).

The area under the first moment curve ($AUMC_{last}$=area under the concentration times time versus time curve from the time of dosing to the last measurable concentration). The area under the first moment curve extrapolated to infinity ($AUMC_{0-\infty}$=$AUMC_{last}$+$C_{last}$×t/λz+$C_{last}$/λz$^2$). The mean residence time (MRT=$AUMC_{0-\infty}$/$AUC_{0-\infty}$) and the steady state volume of distribution (Vdss=MRT×Cl).

Clearance and volume of distribution can also be obtained using methods known to one of skill in the art (see e.g., Handbook of Essential Pharmacokinetics, Pharmacodynamics and Drug Metabolism for Industrial Scientists, Younggil Kwon, pp 18-28 (Non-compartmental Approach)).

Compound Analytical Data

| Cmpd No. | LCMS ES+ | LCMS (Rt min) | HNMR |
|---|---|---|---|
| I-1 | 534 | 2.31 | H NMR (400.0 MHz, DMSO) d 8.99 (bs, 2H), 8.98 (s, 1H), 8.37 (d, J = 8.3 Hz, 2H), 8.13 (d, J = 8.3 Hz, 2H), 7.95 (d, J = 8.6 Hz, 2H), 7.86 (s, 1H), 7.72 (d, J = 8.3 Hz, 2H), 7.24 (bs, 2H), 4.30 (t, J = 5.9 Hz, 2H), 3.98-3.94 (m, 2H), 3.48 (m, 1H), 3.37-3.31 (m, 3H), 2.05 (m, 2H), 1.62 (m, 2H) and 1.19 (d, J = 6.8 Hz, 6H) ppm |
| II-2 | 541.3 | 0.82 | 1H NMR (500 MHz, DMSO) 9.10 (s, 2H), 8.97 (s, 1H), 8.39 (d, J = 8.7 Hz, 2H), 8.13 (d, J = 8.4 Hz, 2H), 7.95 (d, J = 8.7 Hz, 2H), 7.85 (s, 1H), 7.75 (d, J = 8.2 Hz, 2H), 7.23 (s, 2H), 4.33-4.26 (m, 2H), 3.96 (dd, J = 10.9, 3.6 Hz, 2H), 3.62 (s, 1H), 3.34 (t, J = 11.9 Hz, 2H), 2.06 (d, J = 11.5 Hz, 2H), 1.66 (ddd, J = 14.0, 10.1, 2.8 Hz, 2H). |

Comparison Data

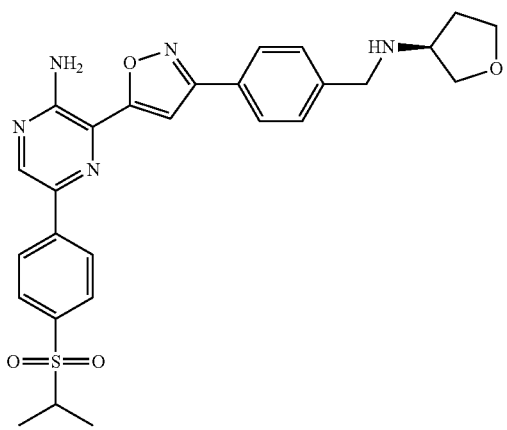 [SMILES: CC(C)S(=O)(=O)c1ccc(-c2cnc(N)c(-c3cc(-c4ccc(CN[C@H]5CCOC5)cc4)no3)n2)cc1]

Compound P110 from WO2020/071837

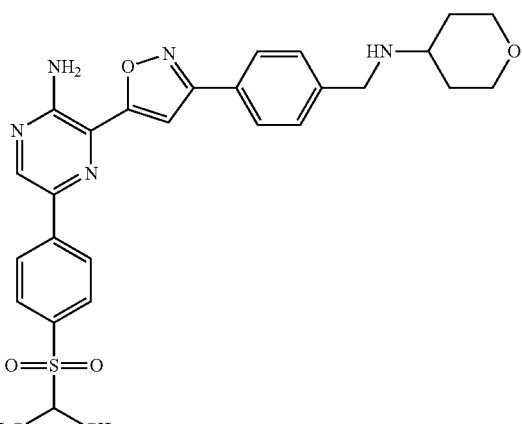

Compound I-1

Biology Comparison Data

| Cmpd No. | Single agent HT116 IC50 (nM) | ATR inhibition Ki (nM) | ATR cellular IC50 (nM) | Cisplatin sensitization (nM) |
|---|---|---|---|---|
| I-1 | 83 | 0.14 | 13 | 39 |
| II-2 | 59 | 0.105 | — | 39 |
| P-110 (S) | 280 | 0.26 | 46 | 156 |
| P-110 (R) | 205 | 0.29 | 54 | 78 |

Compound Pharmacokinetic Comparison Data

| Cmpd No. | Clearance (mL/min/Kg) | $V_{ss}$ (liters/kg) | $T_{1/2}$ (hours) |
|---|---|---|---|
| I-1 | 7.1 | 2.8 | 4.7 |
| II-2 | — | — | — |
| P-110 (S) | — | — | — |
| P-110 (R) | 12.7 | — | 2.7 |

Compounds I-1 and II-2 demonstrate surprisingly good properties compared to compounds in the prior art. Above, compounds I-1 and II-2 are compared with compound P-110, disclosed in WO 2010/071837, and its isomer. Compound I-1 has a surprisingly better ability to kill cancer cells as a single agent (see single agent HT116 IC50), better inhibitory activity against the full length recombination ATR protein (see ATR inhibition Ki), better ATR cellular inhibition (see ATR cellular IC50), and better synergy with cisplatin (see cisplatin sensitization). Compound I-1 also demonstrates lower clearance as well as a longer half-life. Compound II-2 similarly shows better a surprisingly better ability to kill cancer cells as a single agent (see single agent HT116 IC50), better inhibitory activity against the full length recombination ATR protein (see ATR inhibition Ki), and better synergy with cisplatin (see cisplatin sensitization).

In mouse grafted with tumors, Compound I-1 has created oral exposure in tumors compared with Compound P-110 (see FIG. 6).

Example 14

COLO205 Model

In a Colo205 model using irinotecan (20 mg/kg) as the DNA damaging agent, Compound I-1 dosed orally as a solution at 40 mg/kg, for three consecutive days of a four-day cycle, for five cycles (PO, qd3) led to marked regression of tumors.

Compound I-1: % T/C=10.9 at day 13
Compound P-110 dosed in the same model at 45 mg/kg twice a day (bid) showed no sensitization.
T/C=tumour size of treatment group compared with control group

Example 15

Primary Non-Small Cell Lung Cancer (NSCLC) Model

In a primary NSCLC model using cisplatin (3 mg/kg) as the DNA damaging agent, Compound I-1 administered at 30 mg/kg uid q2d led to marked regression of tumors;
Compound I-1: % T/C=1.7 at day 20
Compound P-110 dosed in the same model at 30 mpk bid (on/1 day off) showed no sensitisation T/C=tumour size of treatment group compared with control group While we have described a number of embodiments of this invention, it is apparent that our basic examples may be altered to provide other embodiments that utilize the compounds, methods, and processes of this invention. Therefore, it will be appreciated that the scope of this invention is to be defined by the appended claims rather than by the specific embodiments that have been represented by way of example herein.

The invention claimed is:

1. A compound of formula I-1:

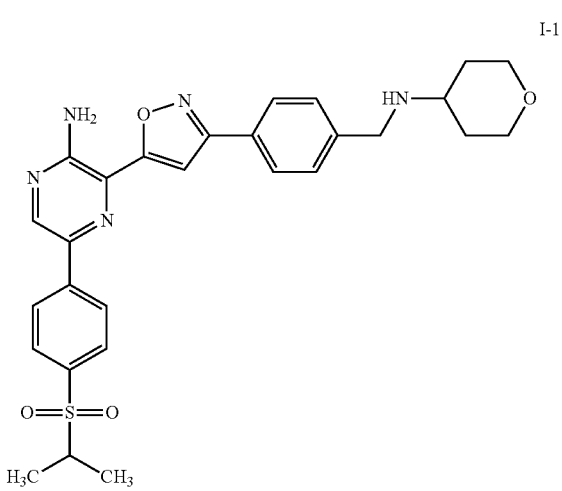 [SMILES: CC(C)S(=O)(=O)c1ccc(-c2cnc(N)c(-c3cc(-c4ccc(CNC5CCOCC5)cc4)no3)n2)cc1]

I-1 or a pharmaceutically acceptable salt thereof.

2. A pharmaceutical composition comprising a compound of claim 1 and a pharmaceutically acceptable carrier.

3. A method for treating cancer in a patient in need thereof comprising administering a compound of claim 1 or a pharmaceutically acceptable derivative thereof.

4. The method of claim 3, further comprising administering to said patient an additional therapeutic agent selected from a DNA-damaging agent; wherein said additional therapeutic agent is appropriate for the disease being treated; and said additional therapeutic agent is administered together with said compound as a single dosage form or separately from said compound as part of a multiple dosage form.

5. The method of claim 4, wherein said DNA-damaging agent is selected chemotherapy or radiation treatment.

6. The method of claim 4, wherein said DNA-damaging agent is selected from ionizing radiation, a platinating agent, a Topo I inhibitor, a Topo II inhibitor, an antimetabolite, an alkylating agent, or an alkyl sulphonates.

7. The method of claim 6, wherein said platinating agent is selected from Cisplatin, Oxaliplatin, Carboplatin, Nedaplatin, Lobaplatin, Triplatin Tetranitrate, Picoplatin, Satraplatin, ProLindac and Aroplatin; said Topo I inhibitor is selected from Camptothecin, Topotecan, Irinotecan/SN38, Rubitecan and Belotecan; said Topo II inhibitor is selected from Etoposide, Daunorubicin, Doxorubicin, Aclarubicin, Epirubicin, Idarubicin, Amrubicin, Pirarubicin, Valrubicin, Zorubicin and Teniposide; said antimetabolite is selected from Aminopterin, Methotrexate, Pemetrexed, Raltitrexed, Pentostatin, Cladribine, Clofarabine, Fludarabine, Thioguanine, Mercaptopurine, Fluorouracil, Capecitabine, Tegafur, Carmofur, Floxuridine, Cytarabine, Gemcitabine, Azacitidine and Hydroxyurea; said alkylating agent is selected from Mechlorethamine, Cyclophosphamide, Ifosfamide, Trofosfamide, Chlorambucil, Melphalan, Prednimustine, Bendamustine, Uramustine, Estramustine, Carmustine, Lomustine, Semustine, Fotemustine, Nimustine, Ranimustine, Streptozocin, Busulfan, Mannosulfan, Treosulfan, Carboquone, ThioTEPA, Triaziquone, Triethylenemelamine, Procarbazine, Dacarbazine, Temozolomide, Altretamine, Mitobronitol, Actinomycin, Bleomycin, Mitomycin and Plicamycin.

8. The method of claim 4, wherein said platinating agent is selected from Cisplatin, Oxaliplatin, Carboplatin, Nedaplatin, or Satraplatin; said Topo I inhibitor is selected from Camptothecin, Topotecan, irinotecan/SN38, rubitecan; said Topo II inhibitor is selected from Etoposide; said antimetabolite is selected from methotrexate, pemetrexed, Thioguanine, Fludarabine, Cladribine, Cytarabine, gemcitabine, 6 Mercaptopurine, or 5 Fluorouracil; said alkylating agent is selected from nitrogen mustards, nitrosoureas, triazenes, alkyl sulfonates, Procarbazine, or aziridines; and said antibiotic is selected from Hydroxyurea, Anthracyclines, Anthracenediones, or Streptomyces family.

9. The method of claim 4 wherein said DNA-damaging agent is a platinating agent or ionizing radiation.

10. The method of claim 4, wherein the antimetabolite is gemcitabine.

11. The method of claim 4, wherein the DNA-damaging agent is selected from one or more of the following: Cisplatin, Carboplatin, gemcitabine, Etoposide, Temozolomide, or ionizing radiation.

12. The method of claim 3, wherein said cancer is a solid tumor selected from the following cancers: Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, multiple endocrine neoplasia type 2A, multiple endocrine neoplasia type 2B, familial medullary thyroid cancer, pheochromocytoma, paraganglioma; and Adrenal glands: neuroblastoma.

13. The method of claim 12, wherein said cancer is selected from a cancer of the lung or the pancreas.

14. The method of claim 3, wherein said cancer is selected from lung cancer, head and neck cancer, pancreatic cancer, gastric cancer, or brain cancer.

15. The method of claim 3, wherein said cancer is selected from non-small cell lung cancer, small cell lung cancer, pancreatic cancer, biliary tract cancer, head and neck cancer, bladder cancer, colorectal cancer, glioblastoma, esophageal cancer, breast cancer, hepatocellular carcinoma, or ovarian cancer.

16. A method of treating pancreatic cancer comprising administering to a patient in need thereof a compound of a compound of claim 1 in combination with an additional therapeutic agent selected from Gemcitabine, radiation therapy, or both Gemcitabine and radiation therapy together.

17. A method of increasing the sensitivity of pancreatic cancer cells to a cancer therapy selected from chemotherapy or radiation therapy by administering to a patient having pancreatic cancer a compound of claim 1.

18. A method of treating non-small cell lung cancer comprising administering to a patient in need thereof a compound of claim 1 in combination with one or more of the following additional therapeutic agents: Cisplatin or Carboplatin, Etoposide, and ionizing radiation.

19. A compound of Formula II:

II or a pharmaceutically acceptable salt thereof,
wherein each $R^{1a}$, $R^{1b}$, $R^{1c}$, $R^2$, $R^{3a}$, $R^{3b}$, $R^{3c}$, $R^4$, $R^5$, $R^6$, $R^7$, $R^8$, $R^{9a}$, $R^{9b}$, $R^{10}$, $R^{11a}$, $R^{11b}$, $R^{12a}$, $R^{12b}$, $R^{13a}$, $R^{13b}$, $R^{14a}$, and $R^{14b}$ is independently hydrogen or deuterium, and at least one of $R^{1a}$, $R^{1b}$, $R^{1c}$, $R^2$, $R^{3a}$, $R^{3b}$, $R^{3c}$, $R^4$, $R^5$, $R^6$, $R^7$, $R^8$, $R^{9a}$, $R^{9b}$, $R^{10}$, $R^{11a}$, $R^{11b}$, $R^{12a}$, $R^{12b}$, $R^{13a}$, $R^{13b}$, $R^{14a}$, or $R^{14b}$ is deuterium.

20. A solid form of a compound of formula I-1:

I-1 wherein the form is selected from the group consisting of Compound I-1 freebase, Compound I-1•hydrochloric acid, Compound I-1 freebase hydrate, Compound I-1•2-hydrochloric acid•1.5H$_2$O, and Compound I-1•hydrochloric acid hydrate.

21. A process for preparing crystalline Compound I-1•hydrochloric acid comprising adding about 1.1 equivalents of HCl (aq) to a solution of Compound I-1 free base in ethanol at a temperature in a range of 20-55° C. to form crystalline Compound I-1•hydrochloric acid.

22. A process for preparing crystalline Compound I-1 free base comprising adding an aqueous solution of NaOH to a solution of Compound I-1•acid salt in ethanol at a temperature in a range of 14-42° C. to form crystalline Compound I-1 free base.

23. The solid form of claim 20, wherein the form is Compound I-1 free base.

24. The solid form of claim 20, wherein the form is crystalline Compound I-1 free base.

25. The solid form of claim 24, having a triclinic crystal system, having a P-1 space group, and having the following unit cell dimensions in Å when measured at 120K:
a=6.7319(2) Å
b=12.3762(3) Å
c=17.2422(4) Å.

26. The solid form of claim 24, characterized by a weight loss of from about 0.4% in a temperature range of from about 25° C. to about 350° C.

27. The solid form of claim 24, characterized by one or more peaks expressed in 2-theta±0.2 at about 11.6, 14.3, 18.4, 22.4, and 27.9 degrees in a X-ray powder diffraction pattern obtained using Cu K alpha radiation.

28. The solid form of claim 24, characterized as having an X-ray powder diffraction pattern substantially the same as that shown in FIG. 1A.

29. The solid form of claim 20, wherein the form is Compound I-1•hydrochloric acid.

30. The solid form of claim 29, wherein the form is crystalline Compound I-1•hydrochloric acid.

31. The solid form of claim 30, characterized by a weight loss of from about 0.7% in a temperature range of from about 25° C. to about 250° C.

32. The solid form of claim 30, characterized by one or more peaks expressed in 2-theta±0.2 at about 12.9, 15.3, 15.6, 18.2, and 23.3 degrees in a X-ray powder diffraction pattern obtained using Cu K alpha radiation.

33. The solid form of claim 30, characterized as having an X-ray powder diffraction pattern substantially the same as that shown in FIG. 1B.

34. The solid form of claim 20, wherein the form is Compound I-1 free base hydrate.

35. The solid form of claim 34, wherein the form is crystalline Compound I-1 free base hydrate.

36. The solid form of claim 35, characterized by a weight loss of from about 0.95% in a temperature range of from about 25° C. to about 375° C.

37. The solid form of claim 35, characterized by one or more peaks expressed in 2-theta±0.2 at about 8.1, 9.4, 14.6, 19.2, and 19.7 degrees in a X-ray powder diffraction pattern obtained using Cu K alpha radiation.

38. The solid form of claim 35, characterized as having an X-ray powder diffraction pattern substantially the same as that shown in FIG. 1C.

39. The solid form of claim 20, wherein the form is Compound I-1•2-hydrochloric acid•1.5H$_2$O.

40. The solid form of claim 39, wherein the form is crystalline Compound I-1•2-hydrochloric acid•1.5H$_2$O.

41. The solid form of claim 40 characterized by one or more peaks expressed in 2-theta±0.2 at about 7.0, 12.6, 14.0, 16.9, and 26.1 degrees in a X-ray powder diffraction pattern obtained using Cu K alpha radiation.

42. The solid form of claim 40, characterized as having an X-ray powder diffraction pattern substantially the same as that shown in FIG. 1D.

43. The solid form of claim 20, wherein the form is Compound I-1•hydrochloric acid hydrate.

44. The solid form of claim 43, wherein the form is crystalline Compound I-1•hydrochloric acid hydrate.

45. The solid form of claim 44 characterized by a weight loss of from about 7.5% in a temperature range of from about 25° C. to about 100° C.

46. The solid form of claim 44 characterized by one or more peaks expressed in 2-theta±0.2 at about 7.7, 16.2, 19.0, 19.8, and 23.4 degrees in a X-ray powder diffraction pattern obtained using Cu K alpha radiation.

47. The solid form of claim 44 characterized as having an X-ray powder diffraction pattern substantially the same as that shown in FIG. 1E.

* * * * *